United States Patent [19]

Segev

[11] Patent Number: 5,843,650
[45] Date of Patent: Dec. 1, 1998

[54] NUCLEIC ACID DETECTION AND AMPLIFICATION BY CHEMICAL LINKAGE OF OLIGONUCLEOTIDES

[76] Inventor: David Segev, 9A Dov Shamir, 76804 Mazkeret Batya, Israel

[21] Appl. No.: 431,527

[22] Filed: May 1, 1995

[51] Int. Cl.$^6$ .............................. C12Q 1/68; C12P 19/34; C07H 21/02; C07H 21/04
[52] U.S. Cl. .................. 435/6; 435/4; 435/5; 435/91.1; 435/91.2; 435/91.3; 536/23.1; 536/24.3; 536/24.31; 536/24.32; 536/24.33
[58] Field of Search ........................ 435/4, 5, 6, 91.2, 435/91.3, 91.1; 536/24.1, 24.3, 24.31, 24.32, 24.33

[56] References Cited

U.S. PATENT DOCUMENTS

| | | | |
|---|---|---|---|
| 5,185,243 | 2/1993 | Ullman et al. | 435/6 |
| 5,359,100 | 10/1994 | Urdea et al. | 552/105 |
| 5,424,413 | 6/1995 | Hogan et al. | 536/24.31 |
| 5,427,929 | 6/1995 | Richards et al. | 435/91.2 |
| 5,437,977 | 8/1995 | Segev | 435/6 |
| 5,451,503 | 9/1995 | Hogan et al. | 435/6 |

FOREIGN PATENT DOCUMENTS

| | | |
|---|---|---|
| 450 594 A2 | 10/1991 | European Pat. Off. . |
| 552 931 A1 | 7/1993 | European Pat. Off. . |
| WO 94/29485 | 12/1994 | WIPO . |

OTHER PUBLICATIONS

Wu et al, "The ligation amplification reaction (LAR)–Amplification of specific DNA sequences using sequential rounds of template directed ligation", Genomics 4:560–569, May, 1989.

Stratagene Catalog (1994) p. 113, Jan. 1994.

Matthews et al, "Analytical strategies for the use of DNA probes", Anal. Biochem. 169:1–25, Feb. 1988.

*Primary Examiner*—Stephanie W. Zitomer
*Assistant Examiner*—Jeffrey Fredman

[57] ABSTRACT

The present invention and kits are directed to a method of amplifying and detecting single or double-stranded target nucleic acid molecules in a test sample. Amplification is accomplished through the use of a minimum of two oligonucleotide probe complement pairs, wherein members oligonucleotide probes from both pair of oligonucleotide probe complement pairs form a minimum of two oligonucleotide probe pairs, at least one of which is complementary to a given portion of a target nucleic acid sequence which act as template. One of the oligonucleotide probes of each oligonucleotide probe pair have an additional protecting sequence which is not complementary to the target sequence. These additional protecting sequences are preferably complementary to each other. Chemical functionality groups attached to the oligonucleotide probes covalently combine the probes to form a joined oligonucleotide product. The joined oligonucleotide product is formed without the use of enzymes. The reactivity of the chemical functionality groups on each probe is target dependent. The chemical functionality group on each probe is prevented from reacting with other chemical functionality groups on other probes unless the probes are properly hybridized to the target molecule. The chemical functionality groups are covalently attached to the oligonucleotide probes in such a way that they are sheltered or protected from the chemical functionality groups of other probes while the probes are in solution. Only when the oligonucleotide probes of an oligonucleotide probe pair are hybridized to the target sequence are the chemical functionality groups on the probes brought into close enough proximity to form a covalent bond and join the probes to form a joined oligonucleotide product. Once formed, the joined oligonucleotide product is denatured from the target nucleic acid molecule thereby doubling the amount of target sequences originally present in the sample. The process is repeated a desired number of times to produce detectable amounts of joined oligonucleotide products.

65 Claims, 22 Drawing Sheets

VERSION 1
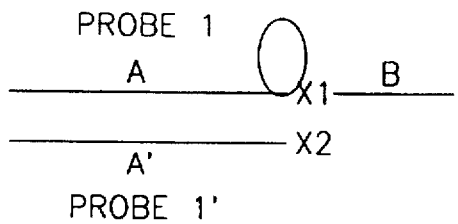
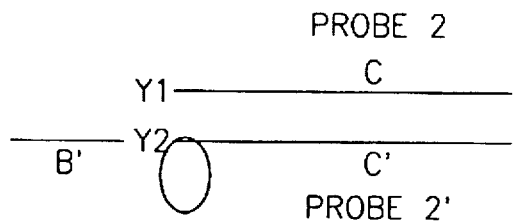
VERSION 2
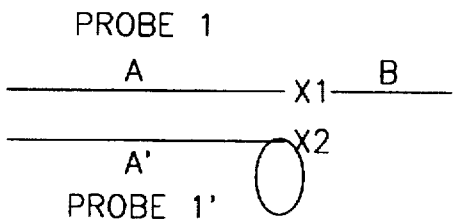
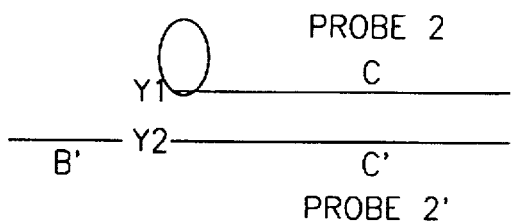
VERSION 3
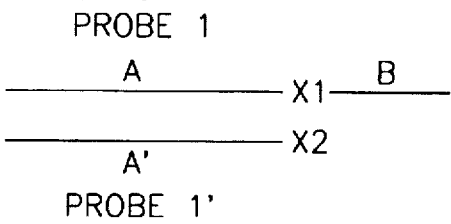
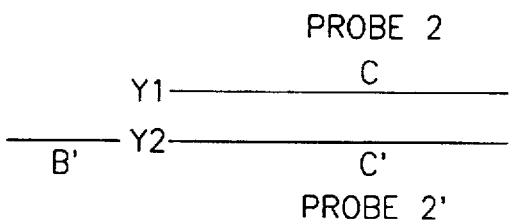
VERSION 4
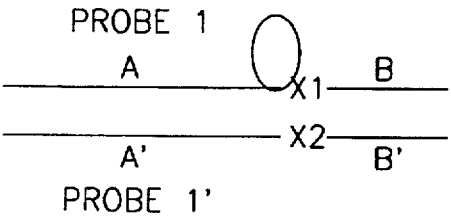
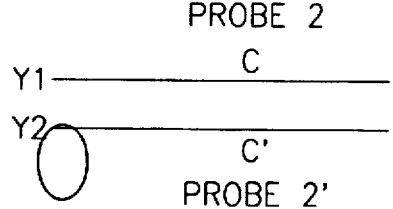
VERSION 5
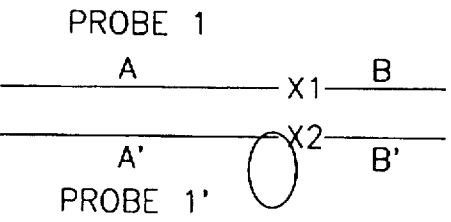
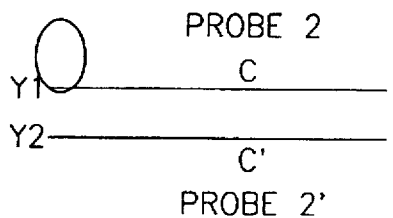
FIG.5-1

VERSION 6
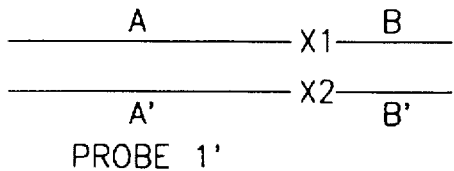
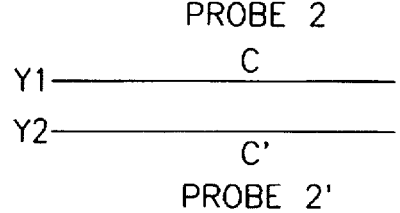
VERSION 7
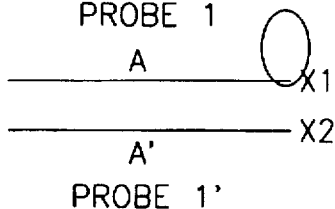
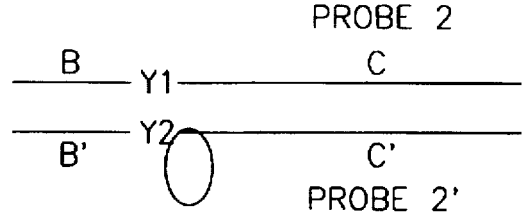
VERSION 8
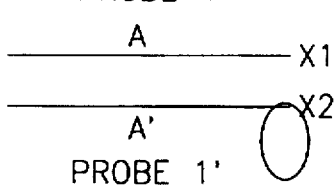
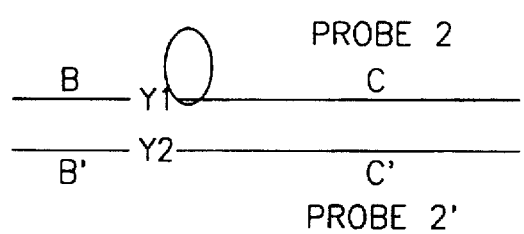
VERSION 9
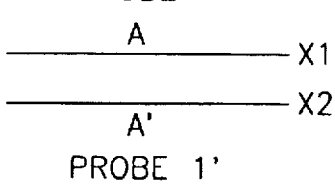
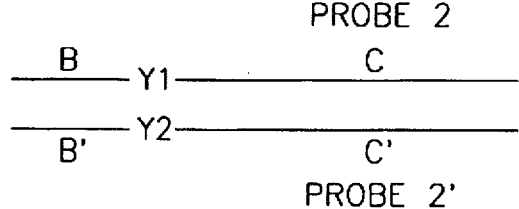
FIG.5-2

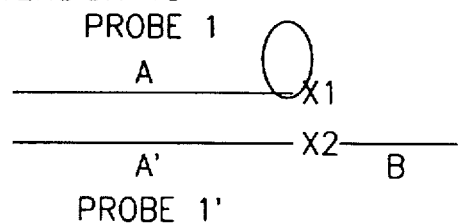
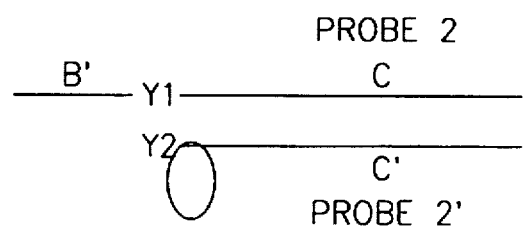
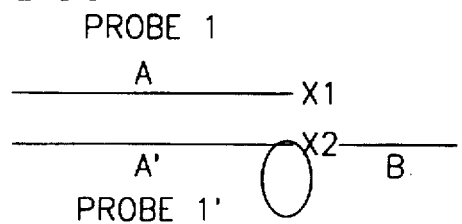
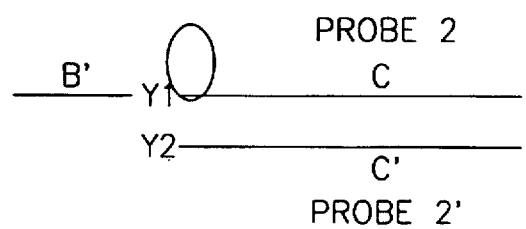
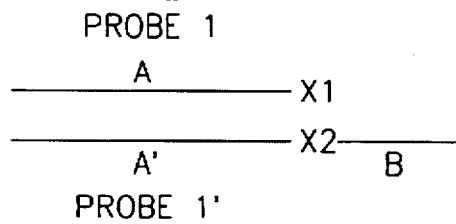
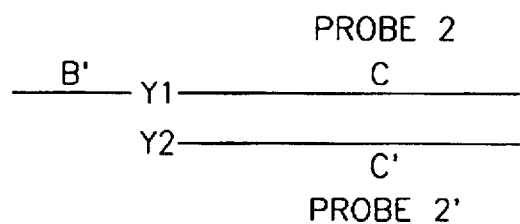
FIG. 5-3

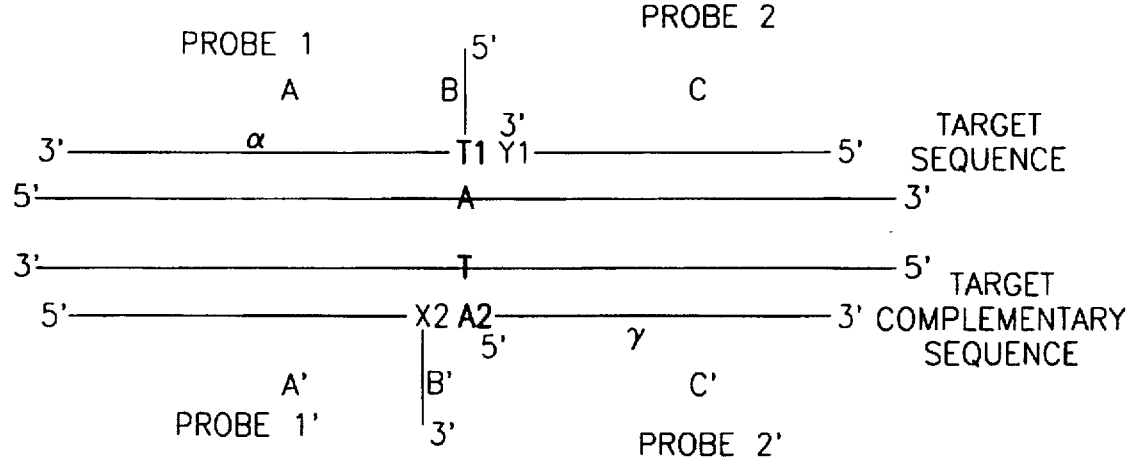
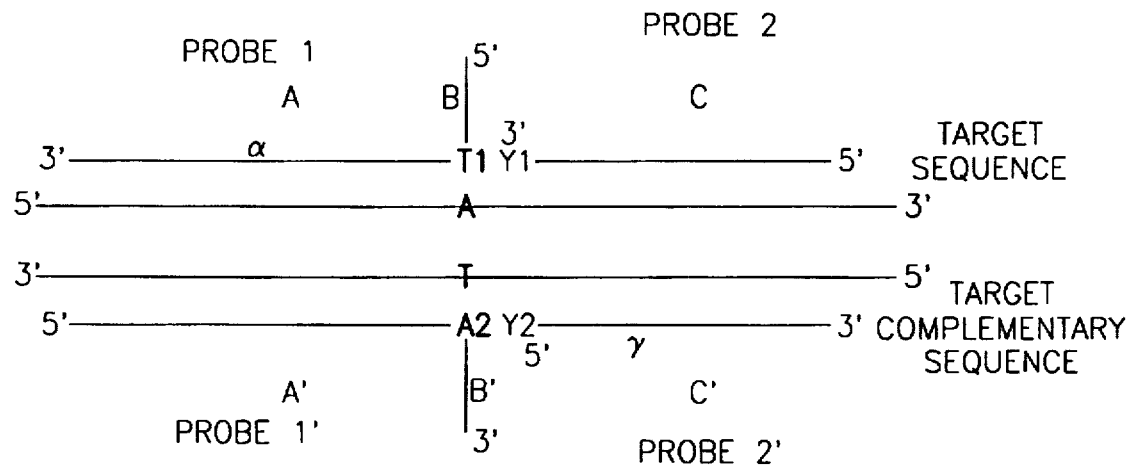
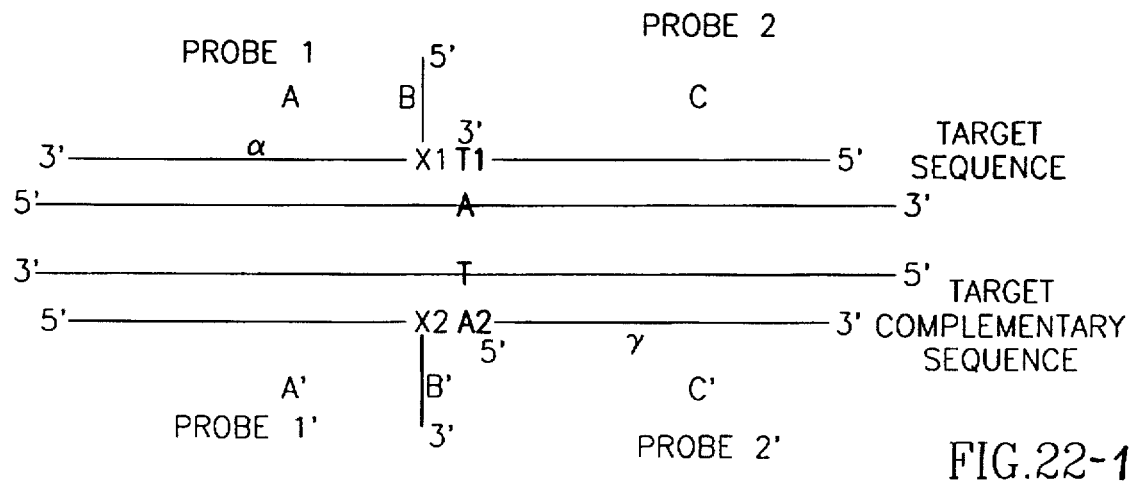
FIG.22-1

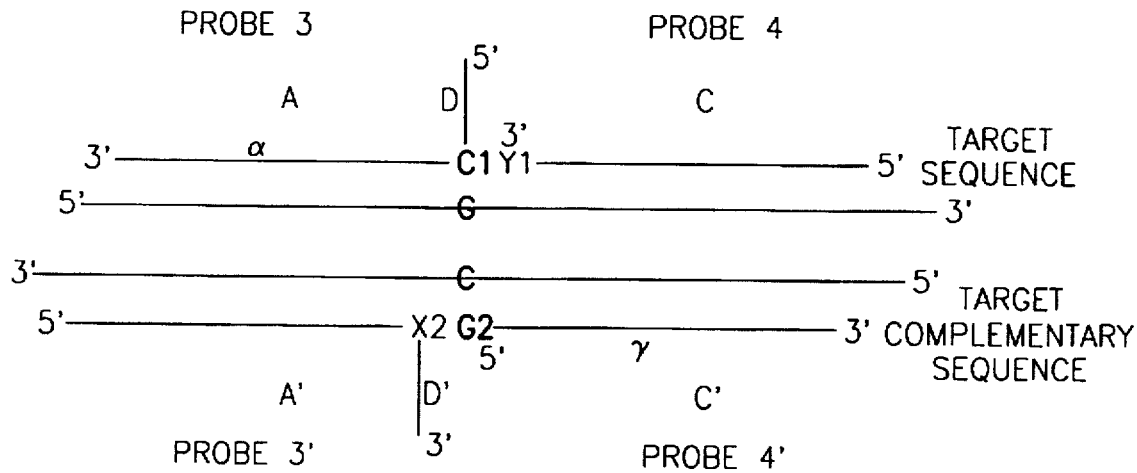
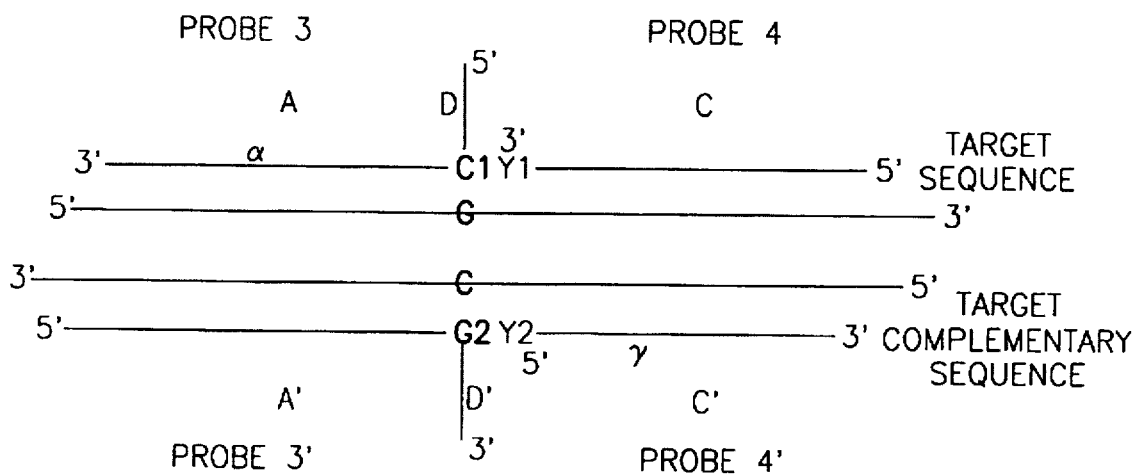
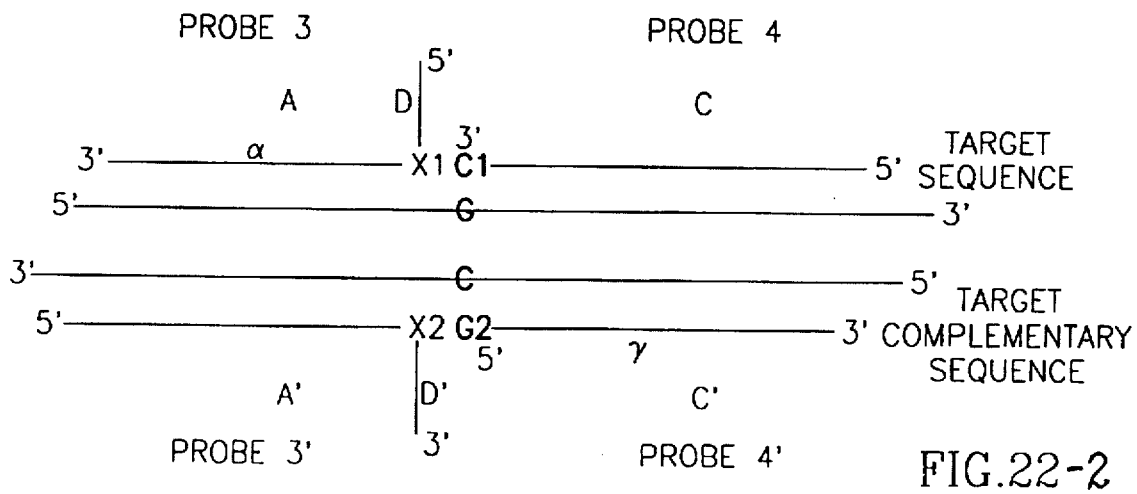
FIG.22-2

AMPLIFICATION PRODUCT

AMPLIFICATION PRODUCT

AMPLIFICATION PRODUCT AGREGATE

NUCLEIC ACID DETECTION AND AMPLIFICATION BY CHEMICAL LINKAGE OF OLIGONUCLEOTIDES

FIELD AND BACKGROUND OF THE INVENTION

The present invention relates to a non-enzymatic method and kit for amplifying and detecting existing target nucleic acid sequences in a test sample.

More particularly, the present invention concerns a method and kit for the detection of the presence of a certain sequence in a sample of genetic material. The method and kit of the present invention are highly sensitive to small alterations in an examined sequence, and thus are useful for detection of minute sequence alterations, such as, for example, point mutations, i.e., single base-pair alterations in a DNA sequence.

The present method and kit are also useful for identifying the presence of a foreign genetic sequence in a sample of genetic material, for example, for detecting the presence of specific bacterial or viral nucleotide sequences in plant and animal DNA. The method is entitled Chemical Amplification of Nucleic Acids and is abbreviated as ChANA.

In the last two decades an extremely large number of human genes have been isolated, fully sequenced and the genetic basis of many diseases such as, for example, Cystic Fibrosis, Hemophilia, Lesch-Nyhan syndrome, β-thalassemia, Sickle Cell Anemia, Phenylketonuria, Tay-Sachs, Gaucher, Duchen/Becker muscular dystrophy and many others have been elucidated. A large number of genetic diseases have been shown to be caused by multiple alternative sequence alterations such as a replacement (e.g., point mutation), or a deletion or insertion of known number of nucleotides, in the genes of different individuals. For example, 177 different point mutations and 66 different insertions and deletions in the CFTR gene have been identified as alternative genetic origins for this gene associated disease, Cystic Fibrosis (Darvasi, A. and Kerem, B. (1994) Short tandem repeats and mutations in the coding region of human genes in press). As a consequence of such point mutations or small sequence alterations, the protein encoded by such genes is not produced, prematurely truncated or is produced in a modified form which affects its functions. Much evidence supports the idea that at least part of the variable penetrance, i.e., age of onset and severeness, characterizing some of the genetic diseases is due to the variability of sequence alterations in their associated genes. Furthermore, many cancers have been shown to be associated with somatic point mutations in certain genes.

It is now possible to obtain genetic material from an individual, amplify a certain gene region using the polymerase chain reaction (PCR) technology, and then identify, by DNA sequencing or by other mutation detection approaches, whether the individual has a mutation at any particular site in this region. Furthermore, it is also possible to determine the genotype of such individual, i.e., whether the individual is healthy, has a certain disease or whether the individual is a "carrier" i.e., is heterozygous for the mutation of the site tested. When such analyses are performed on fetal cells, it becomes possible to determine the probabilities that the fetus will bear a certain inherited disease. This may allow the treatment of the disease shortly after birth using special diets or medicines, or using genetic therapy, or, if treatment is not feasible, offers the option of terminating the pregnancy.

Such techniques have also become important in a number of other applications including in forensic medicine where typically only minute samples are available, in questions of paternity, and in the analysis of a sample for the presence of a nucleic acid of a specific pathogen, for example, nucleic acid of viral origin such as HIV.

As mentioned, many genetic diseases have multiple alternative genetic origins. Some of these diseases are fairly common in certain populations. For example: β-globin defective alleles, causing β-thalassemia, are widely spread in some Middle East populations; various defective CFTR alleles are carried in a heterozygous form by one of twenty individuals (5%) and the disease affects about 1/1600 individuals of Caucasian descent in the world (Harrison's Principles of Internal Medicine 9th Ed. Isselbacher, Adams, Braunwald, Petersdorf and Wilson Eds. McGraw-Hill Book company, N.Y., pp. 1233). Because of the high frequency of Cystic Fibrosis and other genetically inherited disorders there is a widely recognized need for, and it would be highly advantageous to have, a low cost method, demanding merely non skilled personnel for its execution, that enables the efficient and accurate detection of DNA sequence alterations.

The most basic method for detection of point mutations is DNA sequencing, the most widely used sequencing method being based on the dideoxynucleotide chain termination procedure (See, Sanger F. (1981), Science 214, 1205–1210). The development of DNA and dideoxynucleotide conjugated fluorescent dyes, and suitable detection systems, enabled the improvement and the automatization of the basic dideoxy chain termination technique.

Other methods which have been used to determine the presence of alterations in known DNA sequences include allele specific oligonucleotide (ASO) hybridization; reverse-ASO; restriction site generating PCR (RG-PCR); denaturing/temperature gradient gel electrophoresis (D/TGGE); single-strand conformation polymorphism (SSCP); heteroduplex analysis; restriction fragment length polymorphism (RFLP); PCR restriction fragment length polymorphism (PCR-RFLP); nuclease protection assays; chemical cleavage and other, less frequently used, methods.

These methods, although of great scientific importance, suffer from drawbacks limiting their routine use since they lack one or more of the following aspects rendering a method applicable for wide screening of various DNA alterations in many individuals. These aspects include: (1) Highly skilled personnel are needed for (a) accurate execution of the procedures, many of which include several complicated steps, specially gel electrophoresis and/or complicated blotting and hybridization procedures, and (b) for interpreting the results; (2) Strict calibration steps are needed before the examination of any new DNA alteration; (3) Theoretically, some of the above mentioned procedures, are not suitable for the detection of all alterations; (4) Some are time and effort consuming regarding the procedures themselves and/or the interpretation of their results; (5) Some of the procedures, specially those involving gel electrophoresis, are not easy to automate; and above all, (6) these methods are all based upon the use of enzymes such as DNA and RNA polymerases, restriction endonucleases single-strand-specific endo- and exonucleases and the like, which in addition to being expensive, exhibit lot-to-lot variations in activity and in the concentration of undesired nuclease contaminants. Such variations detract further from the reliability of these methods.

As mentioned, advances in the field of molecular biology over the last two decades have enabled the detection of specific nucleic acid sequences in test samples taken from a patient or other subject. Such test samples include serum, urine, feces, saliva, amniotic fluid, and other bodily fluids. Detection of specific nucleic acid sequences can be used to identify genetic disorders or diseases, as well as the presence of pathogenic bacterial and viral disease agents in humans and other species.

In many cases of interest, a desired nucleic acid sequence is present at a very low concentration in an examined sample. In such cases, unless assay sensitivity can be increased, the presence if the desired molecule may escape detection.

The standard method for amplifying and detecting target nucleic acid sequences is the polymerase chain reaction (PCR), (see Saiki et al. Science 239, 487 (1988) and Mullis et al in U.S. Pat. No. 4,683,195). A problem with PCR is non-specific polymerization leading to spurious background signals.

The PCR method is aimed at the amplification of a specific nucleic acid sequence. It enables a repeated replication of a desired specific nucleic acid sequence using two oligonucleotide primers complementary each to either strand of the sequence to be amplified. Extension products, to which these primers are incorporated, then become templates for subsequent replication steps. The method selectively increases the concentration of a desired nucleic acid sequence in a geometric rate even when that sequence is not purified prior to amplification, and is present only in a single copy in a particular sample. The PCR method may be used to amplify either single or double-stranded DNA or complementary DNA (cDNA).

PCR technology is useful in that it achieves a rapid and extensive amplification of a polynucleotide molecule. Nevertheless, two practical problems exist when the PCR method is applied for amplification of target nucleic acid sequences: (1) non-specific hybridization between extraneous sequences, in an examined nucleic acid, with the amplification primers may results in a co-amplification of irrelevant sequences. Furthermore, as the level of amplification increases, the quantity of such co-amplification products also increase; (2) because of the ability of PCR to readily generate millions of copies for each initial template, accidental introduction of the end product of a previous reaction into other samples easily leads to false-positive results.

The advent of PCR led to the development of additional amplification methods. One such alternative method is disclosed by Backman et al., EP 320 308, known as the ligase chain reaction (LCR), for amplifying a target nucleic acid sequence. In LCR, four oligonucleotide probes are employed in excess. The first and third probes form a complementary oligonucleotide probe pair. The second and fourth probes form another complementary oligonucleotide probe pair. The first and second probes hybridize to sequences that are contiguous in the first strand of the target nucleic acid sequence. When hybridized, the first and second probes abut one another in a 5' phosphate-3' hydroxyl relationship, so that a ligase can join the two probes into a fused product. Also, the third and fourth probes hybridize to sequences that are contiguous in the second strand of the target nucleic acid sequence. When hybridized, the third and fourth probes abut one another in a 5' phosphate-3' hydroxyl relationship, so that a ligase can join the two probes into a second fused product.

The first and second fused products are separated from the target strands, in effect doubling the target population in the sample. The fused products then serve as templates for further LCR reactions by hybridizing to the complementary probes. As the cycle of hybridization, ligation and denaturation is repeated, the population of fused probes increases at a geometric rate. The fused probes are detected by standard methods.

These amplification reactions permit rapid analysis or characterization of sequences of interest, even where the starting amount of material is extremely small. However, it is important that the amplification process be highly specific, since the amplification of untargeted sequences along with the target signal impairs the reliability of the amplification process.

One problem associated with LCR is that, by definition, the procedure requires four oligonucleotide probes and a ligase, and may result in the non-specific "blunt-end ligation" of the oligonucleotide probes. Such non-specific "blunt-end ligation", should it occur, cause a target-independent geometric amplification of the fused products. This can lead to high background signal of false-positive results. These target-independent products are indistinguishable from the desired amplified target sequence.

Both PCR and LCR have an additional drawback due to the requirement of polymerases or ligases, respectively, in order to achieve amplification. In addition to being expensive, such enzymes exhibit lot-to-lot variations in activity and in the concentration of undesired nuclease contaminants. Such variations detract further from the reliability of these methods.

In order to overcome the use of enzymes in the amplification process, Segev disclosed (international PCT application US 94/06690) a new chemical process, aimed at the non-enzymatic amplification of any specific nucleic acid sequence. In this method, named Chemical Amplification Reaction (CAR), two oligonucleotide probe complement pairs are used, wherein:

(a) the first oligonucleotide probe complement pair consists of oligonucleotide probe 1 and oligonucleotide probe 1', and the second oligonucleotide probe complement pair consists of oligonucleotide probe 2 and oligonucleotide probe 2';

(b) Oligonucleotide probe 1 includes a long sequence H and a short sequence I; oligonucleotide probe 1' includes a long sequence H' and a short sequence I'; Oligonucleotide probe 2 includes a long sequence J and a short sequence K; oligonucleotide probe 2' includes a long sequence J' and a short sequence K';

(c) Oligonucleotide probes 1 and 2 form a first oligonucleotide pair, whereas oligonucleotide probes 1' and 2' form a second oligonucleotide pair; long sequence H of oligonucleotide probe 1 and long sequence J of oligonucleotide probe 2 are complementary to adjacent portions of the target sequence; and long sequence H' of oligonucleotide probe 1' and long sequence J' of oligonucleotide probe 2' are complementary to adjacent portions of the target complementary sequence;

(d) Short sequence I of oligonucleotide probe 1 is complementary to short sequence K of oligonucleotide probe 2 and short sequence I' of oligonucleotide probe 1' is complementary to short sequence K' of oligonucleotide probe 2'; Short sequences do not hybridize to the target sequence.

(e) The sugar or base moieties of nucleotides consisting short sequences are modified with chemical functionality groups X and Y, wherein X and Y groups could form a chemical bond. The oligonucleotide probes used for CAR are shown in FIG. 1 wherein the vertical line demarcate the border between long and short sequences.

(f) When these oligonucleotide probes are made in contact with a double-stranded sequence, composed of a target sequence and a target complementary sequence, the hybridizations shown in FIG. 2 occur.

In the CAR method. Long sequences serve for target oriented hybridization while short sequences serve a dual function: (a) they shield and therefore restrict chemical active groups X and Y from interacting with one another when long sequences are not hybridized with the target sequence; (b) they bring chemical active groups X and Y to a proximity and orientation facilitating their interaction when long sequences are hybridized with the target sequence. leading to hybridization between the short sequences.

However, his method has a major drawback since a cross-like structure (shown in FIG. 3) of a high thermodynamic stability may form, and upon amplification may result in a template independent false-positive amplification products.

Another drawback of the above method is its inability to discriminate among target nucleic acid sequences which differ by a minute sequence alteration, such as a point mutation, i.e. a single base pair alteration. Therefore, the CAR method is not suitable for the detection of minute sequence alterations such as point mutations.

It is an object of the present invention to provide a simple, rapid and highly accurate method of amplification and detection of target sequences that uses neither polymerase nor ligase. and that reduced spurious background signals and, therefore, improves the reliability of a chemical amplification reaction of a nucleic acid.

It is another object of the present invention to provide a sensitive method for chemical amplification of nucleic acids which is sensitive enough to discriminatively amplify nucleic acid sequences which differ by a minute sequence alteration, such as for example a single base alteration, i.e., a point mutation.

It is yet another object of the present invention to provide a diagnostic kit to be used for carrying out the above method of the invention, which will enable in situ detection, that is a detection procedure that yields a detectable signal associated with amplification, without the need to reopen the reaction vessel post amplification, which procedure reduces the problem of contamination by previous amplification products and, therefore, reduces false-positive results.

SUMMARY OF THE INVENTION

The present invention concerns a method and kit for detecting a target nucleic acid sequence which may be present in a test sample. The method is sensitive enough to discriminate among sequences which differ by a minute sequence alteration such as, for example, a point mutation, i.e. a single base pair alteration. The method may employ both an amplification procedure and a detection procedure. These and other objectives, as will become apparent to those who are skilled in the art, have been met by providing a process for amplifying and detecting, in a sample, a single-stranded nucleic acid target molecule consisted of a target sequence, or a double-stranded nucleic acid target molecule consisted of a target sequence and a target complementary sequence.

Amplification is accomplished through the use of a minimum of two oligonucleotide probe complement pairs, wherein members oligonucleotide probes from both pair of oligonucleotide probe complement pairs form two oligonucleotide probe pairs which are complementary to a given portion of the target nucleic acid sequence and the target nucleic acid complementary sequence, should it exist, which act as templates. The nucleotide sequence of the members of each pair of oligonucleotide probes is selected to be complementary to a different portion of the target nucleic acid sequence, so as each oligonucleotide probe pair essentially cover a predefined nucleotide stretch of the target sequence in a non-contiguous manner. The mode of amplification imposed by these unique oligonucleotide probe pairs consists of the following steps:

(a) contacting a first oligonucleotide probe complement pair and a second oligonucleotide probe complement pair with stretches of nucleotide bases present in the nucleic acids of interest, wherein:

(i) the first oligonucleotide probe complement pair consists of oligonucleotide probe 1 and oligonucleotide probe 1' and the second oligonucleotide probe complement pair consists of oligonucleotide probe 2 and oligonucleotide probe 2';

(ii) oligonucleotide probe 1 consists of a targeting sequence A, which includes a long part $\alpha$ and a short part $\alpha'$, and of a protecting sequence B; oligonucleotide probe 1' consists of a targeting sequence A' and a protecting sequence B';

(iii) oligonucleotide probe 2 consists of a targeting sequence C; oligonucleotide probe 2' consists of a targeting sequence C' which includes a long part $\gamma$ and a short part $\gamma'$;

(iv) part $\alpha$ of targeting sequence A of oligonucleotide probe 1 and targeting sequence A' of oligonucleotide probe 1' are complementary to each other;

(v) targeting sequence C of oligonucleotide probe 2 and part $\gamma$ of targeting sequence C' of oligonucleotide probe 2' are complementary to each other; part $\gamma'$ of targeting sequence C' of oligonucleotide probe 2' and part $\alpha'$ of targeting sequence A of oligonucleotide probe 1 are complementary to each other;

(vi) oligonucleotide probes 1 and 2 form a first oligonucleotide pair wherein targeting sequence A of oligonucleotide probe 1 and targeting sequence C of oligonucleotide probe 2 are complementary to adjacent portions of the target sequence;

(vii) oligonucleotide probes 1' and 2' form a second oligonucleotide pair wherein targeting sequence A' of oligonucleotide probe 1' and targeting sequence C' of oligonucleotide probe 2' are complementary to adjacent portions of the target complementary sequence;

(viii) protecting sequence B do not hybridize to the target sequence when targeting sequence A and targeting sequence C hybridize to the target sequence;

(ix) protecting sequence B' do not hybridize to the target complementary sequence when targeting sequence A' and targeting sequence C' hybridize to the target complementary sequence;

(x) in the junction of targeting sequence A and protecting sequence B, a chemical functionality group X1 is attached to the sugar or base moiety of the last nucleotide in targeting sequence A of oligonucleotide probe 1; the sugar or base moiety of the end-nucleotide of targeting sequence C of oligonucleotide probe 2 is modified with chemical functionally group Y1; chemical functionality group X1 is reactive with chemical functionality group Y1;

(xi) in the junction of targeting sequence A' and protecting sequence B', a chemical functionality group X2 is attached to the sugar or base moiety of the last nucleotide in targeting sequence A' of oligonucleotide probe 1'; the sugar or base moiety of the end-nucleotide of targeting sequence C' of oligonucleotide probe 2' is modified with chemical functionality group Y2; chemical functionality group X2 is reactive with chemical functionality group Y2;

(xii) when targeting sequence A and targeting sequence C hybridize to target sequence, chemical functionality group X1 reacts with chemical functionality group Y1 to form a chemical bond, and a complementary strand of joined oligonucleotide (i.e. amplification) product is formed; when targeting sequence A' and targeting sequence C' hybridize to target complementary sequence, chemical functionality group X2 reacts with chemical functionality group Y2 to form a chemical bond, and a complementary strand of amplification product is formed;

(b) providing hybridization conditions to enable targeting sequence A of oligonucleotide probe 1 and targeting sequence C of oligonucleotide probe 2 to hybridize with adjacent portions of the target sequence and to enable targeting sequence A' of oligonucleotide probe 1' and targeting sequence C' of oligonucleotide probe 2' to hybridize with adjacent portions of the target complementary sequence;

(c) providing conditions which will enable the joining oligonucleotide probe 1 and oligonucleotide probe 2, hybridized after step (b) to adjacent portions of the target sequence, to each other by forming a chemical bond between chemical functionality groups X1 and Y1, thereby forming a first joined oligonucleotide product having the target complementary sequence;

(d) providing conditions which will enable the joining of oligonucleotide probe 1' and oligonucleotide probe 2', hybridized after step (b) to adjacent portions of the target complementary sequence, to each other, by forming a chemical bond between chemical functionality groups X2 and Y2, thereby forming a second joined oligonucleotide product having the target sequence;

(e) treating the sample under denaturing conditions;

(f) repeating steps (b) through (e) a desired number of times; and (g) detecting the joined oligonucleotide products.

The method of the present invention is also suitable for the detection of a minute sequence alteration, such as for example a point mutation, i.e. a single base pair alteration, in a target nucleic acid sequence. To this end, two sets each of four oligonucleotide probes are designed. The first set is aimed at the amplification of a wild-type target nucleic acid sequence and of a wild-type target nucleic acid complementary sequence, whereas the second set is aimed at the amplification of a mutant target nucleic acid sequence and of a mutant target nucleic acid complementary sequence. The oligonucleotide probe sets are employed according to the following steps:

(a) contacting a first and a second oligonucleotide probes set with stretches of nucleotide bases present in the nucleic acids of interest, wherein:

(i) the first oligonucleotide probes set is designed to amplify the wild-type sequences and includes four oligonucleotide probes designated 1, 1', 2 and 2' which are similar in their built-up to the ones described above; oligonucleotide probes 1 and 1' form a first oligonucleotide probe complementary pair; oligonucleotide probes 2 and 2' form a second oligonucleotide probe complementary pair; oligonucleotide probes 1 and 2 form a first oligonucleotide probe pair; oligonucleotide probes 1' and 2' form a second oligonucleotide probe pair;

(ii) the second oligonucleotide probes set is designed to amplify the mutant sequences and includes four oligonucleotide probes designated 3, 3', 4 and 4' which are similar in built-up to oligonucleotide probes 1, 1', 2 and 2' of the first oligonucleotide probes set, respectively; oligonucleotide probes 3 and 3' form a third oligonucleotide probe complementary pair; oligonucleotide probes 4 and 4' form a fourth oligonucleotide probe complementary pair; oligonucleotide probes 3 and 4 form a third oligonucleotide probe pair; oligonucleotide probes 3' and 4' form a fourth oligonucleotide probe pair;

(iii) oligonucleotide probes 1 and 3 are each consisted of a targeting sequence A, which includes a long part $\alpha$ and a short part $\alpha'$, and of a protecting sequence B and D, respectively; oligonucleotide probe 1' and 3' are each consisted of a targeting sequence A' and a protecting sequence B' and D', respectively;

(iv) oligonucleotide probe 2 and 4 are each consisted of a targeting sequence C; oligonucleotide probe 2' and 4' are each consisted of a targeting sequence C' which includes a long part $\gamma$ and a short part $\gamma'$;

(v) part $\alpha$ of targeting sequences A of oligonucleotide probes 1 and 3 and targeting sequences A' of oligonucleotide probes 1' and 3' are complementary to each other, respectively;

(vi) targeting sequences C of oligonucleotide probes 2 and 4 and part $\gamma$ of targeting sequences C' of oligonucleotide probes 2' and 4' are complementary to each other, respectively; part $\gamma'$ of targeting sequences C' of oligonucleotide probes 2' and 4' and part $\gamma'$ of sequences A of oligonucleotide probes 1 and 3 are complementary to each other, respectively;

(vii) the sequence of oligonucleotide probes 3' and 4 of the second oligonucleotide probes set is identical or closely similar to the sequence of oligonucleotide probes 1' and 2 of the first oligonucleotide probes set, respectively; the sequence of oligonucleotide probes 3 and 4' of the second oligonucleotide probes set differ from that of oligonucleotide probes 1 and 2' of the first oligonucleotide probes set, respectively, in a position of a sequence alteration to be determined, so that oligonucleotide probes 1 and 2' are fully complementary to the wild-type target sequence and the wild-type target complementary sequence, respectively, at that position, and oligonucleotide probes 3 and 4' are fully complementary to the mutant target sequence and the mutant target complementary sequence, respectively, at that position;

(viii) targeting sequence A of oligonucleotide probe 1 and targeting sequence C of oligonucleotide probe 2 are complementary to adjacent portions of the wild-type target sequence; targeting sequence A of oligonucleotide probe 3 and targeting sequence C of oligonucleotide probe 4 are complementary to adjacent portions of the mutant target sequence;

(ix) targeting sequence A' of oligonucleotide probe 1' and targeting sequence C' of oligonucleotide probe 2' are complementary to adjacent portions of the wild-type target complementary sequence; targeting sequence A' of oligonucleotide probe 3' and targeting sequence C' of oligonucleotide probe 4' are complementary to adjacent portions of the mutant target complementary sequence;

(x) protecting sequences B and D do not hybridize to the wild-type or mutant target sequences, respectively, when targeting sequences A and targeting sequences C hybridize to these target sequences;

(xi) protecting sequences B' and D' do not hybridize to the wild-type or mutant target complementary sequences, respectively, when targeting sequences A' and targeting sequences C' hybridize to these target complementary sequence;

(xii) in the junction of targeting sequence A and protecting sequence B of oligonucleotide probe 1, a chemical functionality group X1 is attached to the sugar or base moiety of the last nucleotide of sequence A; the sugar or base moiety of the end-nucleotide of targeting sequence C of oligonucleotide probe 2 is modified with chemical functionally group Y1; chemical functionality group X1 is reactive with chemical functionality group Y1;

(xiii) in the junction of targeting sequence A and protecting sequence D of oligonucleotide probe 3, a chemical functionality group X3 is attached to the sugar or base moiety of the last nucleotide of sequence A; the sugar or base moiety of the end-nucleotide of targeting sequence C of oligonucleotide probe 4 is modified with chemical functionally group Y3; chemical functionality group X3 is reactive with chemical functionality group Y3;

(xiv) in the junction of targeting sequence A' and protecting sequence B' of oligonucleotide probe 1', a chemical functionality group X2 is attached to the sugar or base moiety of the last nucleotide of sequence A'; the sugar or base moiety of the end-nucleotide of targeting sequence C' of oligonucleotide probe 2' is modified with chemical functionality group Y2; chemical functionality group X2 is reactive with chemical functionality group Y2;

(xv) in the junction of targeting sequence A' and protecting sequence D' of oligonucleotide probe 3', a chemical functionality group X4 is attached to the sugar or base moiety of the last nucleotide of sequence A'; the sugar or base moiety of the end-nucleotide of targeting sequence C' of oligonucleotide probe 4' is modified with chemical functionality group Y4; chemical functionality group X4 is reactive with chemical functionality group Y4;

(xvi) when targeting sequence A and targeting sequence C of oligonucleotide probes 1 and 2, respectively, hybridize to a wild-type target sequence, chemical functionality group X1 reacts with chemical functionality group Y1 to form a chemical bond, and a complementary strand of wild-type joined oligonucleotide product is formed; when targeting sequence A' and targeting sequence C' of oligonucleotide probes 1' and 2' hybridize to a wild-type target complementary sequence, chemical functionality group X2 reacts with chemical functionality group Y2 to form a chemical bond, and a strand of wild-type joined oligonucleotide product is formed;

(xvii) when targeting sequence A and targeting sequence C of oligonucleotide probes 3 and 4, respectively, hybridize to a mutant target sequence, chemical functionality group X3 reacts with chemical functionality group Y3 to form a chemical bond, and a complementary strand of mutant joined oligonucleotide product is formed; when targeting sequence A' and targeting sequence C' of oligonucleotide probes 3' and 4', respectively, hybridize to a mutant target complementary sequence, chemical functionality group X4 reacts with chemical functionality group Y4 to form a chemical bond, and a strand of mutant joined oligonucleotide product is formed;

(b) providing hybridization conditions to enable:

(i) targeting sequence A of oligonucleotide probe 1 and targeting sequence C of oligonucleotide probe 2 to hybridize with adjacent portions of the wild-type target sequence;

(ii) targeting sequence A' of oligonucleotide probe 1' and targeting sequence C' of oligonucleotide probe 2' to hybridize with adjacent portions of the wild-type target complementary sequence;

(iii) targeting sequence A of oligonucleotide probe 3 and targeting sequence C of oligonucleotide probe 4 to hybridize with adjacent portions of the mutant target sequence;

(iv) targeting sequence A' of oligonucleotide probe 3' and targeting sequence C' of oligonucleotide probe 4' to hybridize with adjacent portions of the mutant target complementary sequence;

(c) providing conditions which will enable the joining of oligonucleotide probe 1 and oligonucleotide probe 2, hybridized after step (b) to adjacent portions of the wild-type target sequence, to each other, by forming a chemical bond between chemical functionality groups X1 and Y1, thereby forming a first joined oligonucleotide product having the wild-type target complementary sequence;

(d) providing conditions which will enable the joining of oligonucleotide probe 1' and oligonucleotide probe 2', hybridized after step (b) to adjacent portions of the wild-type target complementary sequence, to each other, by forming a chemical bond between chemical functionality groups X2 and Y2, thereby forming a second joined oligonucleotide product having the wild-type target sequence;

(e) providing conditions which will enable the joining of oligonucleotide probe 3 and oligonucleotide probe 4, hybridized after step (b) to adjacent portions of the mutant target sequence, to each other, by forming a chemical bond between chemical functionality groups X3 and Y3, thereby forming a first joined oligonucleotide product having the mutant target complementary sequence;

(f) providing conditions which will enable the joining of oligonucleotide probe 3' and oligonucleotide probe 4', hybridized after step (b) to adjacent portions of the mutant target complementary sequence, to each other, by forming a chemical bond between chemical functionality groups X4 and Y4, thereby forming a second joined oligonucleotide product having the mutant target sequence;

(g) treating the sample under denaturing conditions;

(h) repeating steps (b) through (g) a desired number of times; and (i) detecting the joined oligonucleotide products.

Also according to the present invention, there is provided a diagnostic kit for amplifying specific nucleotide sequences a sample, consisting of two or more oligonucleotide probes complementary pairs and at least one buffer.

A straight forward approach to achieve an in situ detection of amplification products, that is a detection procedure which does not involve opening the test tubes post amplification, is to design the chemical functionality groups of the X types and of the Y types such as they form a detectable compound when a chemical bond is formed between them.

The detectable compound may for example be detected colourimetically in O.D. units or flourimetrically depending on the chemical nature of the compound. The compound may also be detected via directly or indirectly labeled antibodies, for example a monoclonal antibody, raised against the compound.

During the execution of the amplification procedure described above, at least two single-stranded products B and B' and/or D and D' are formed. These single-stranded sequences are unique to joined oligonucleotide products, therefore, some or all, are employed to detected the presence of joined oligonucleotide products in accordance with two alternative detection procedures. As a matter of simplicity the detection procedure will be described herein for the first oligonucleotide probes set. A similar approach may of course be ascribed to the second oligonucleotide probes set.

In the first detection procedure employed are two labeled detection oligonucleotide probes in a detection process which involves proximity energy transfer labeling. As a first detection oligonucleotide probe serve protecting sequence B and/or B' of oligonucleotide probes 1 and 1', respectively. To the first detection oligonucleotide probe conjugated is a proximity label moiety R1. Conjugated to the second detection oligonucleotide probe B.1 and/or B'.1 is a corresponding second proximity label moiety R2. The second detection oligonucleotide probes B.1 and B'.1 may also be connected directly or indirectly to form a continues molecule B.1–B'.1. The second detection oligonucleotide probes B.1 and B'.1 are complementary to protecting sequence B and B', respectively. The first and second labeled detection oligonucleotide probes hybridize to one another and therefore bring the proximity label moieties R1 and R2 to a proximity which is sufficient for their interaction to produce a detectable signal. When the two labeled detection oligonucleotide probes are hybridized, proximity labeling moieties R1 and R2 are brought into proximity that enables an energy transfer reaction between them to occur, resulting in a measurable energy emission.

The second detection procedure of the amplification products is based upon the release of a label moiety L conjugated to single-stranded B and/or B' sequences which are incorporated into joined oligonucleotide products, and the removal of all double-stranded B and B' sequences along with label moieties L conjugated to them from the test vessel via an affinity separation moiety S conjugated to oligonucleotide probes 1 and/or 1'. The single-stranded B and B' sequences may be nucleated post amplification via the use of a single-stranded specific nuclease, or by a suitable chemical procedure, resulting in the release of the label moiety L conjugated to them to the surrounding solution. To one or more locations of one or more of the oligonucleotide probes used in the amplification reaction, conjugated is one or more affinity separation moiety S. The affinity separation moiety S is characterized by its ability to bind a counterpart moiety S' in high affinity. The counterpart affinity separation moiety S' is preferably attached to a solid support. Following amplification, a single-strand specific nucleolitic process is used to degrade single-stranded sequences B and B' which are incorporated to joined oligonucleotide products.

The result of the nucleolysis is the release of the label moiety L to the solution, in an amount which is proportional to the level of amplification. Label moieties L that where not thus released, these are label moieties which are conjugated to sequences B or B' that were not incorporated into joined oligonucleotide products, are removed by affinity separation. The released label moieties L may thus be detected.

Also according to the present invention, there is provided a diagnostic kit for detecting the presence of specific nucleotide sequences in samples, consisting: (a) two or more oligonucleotide probes complementary pairs; (b) two or more detection oligonucleotide probes conjugated to a proximity labeling moiety; and (c) at least one buffer;

or alternatively consisting: (a) two or more oligonucleotide probes complementary pairs, one or more are conjugated to a separation moiety, and one or more are conjugated to a label moiety; (b) a single-strand specific nuclease; and (e) a solid support for affinity separation of joined oligonucleotide products.

BRIEF DESCRIPTION OF THE DRAWINGS

The invention is herein described, by way of example only, with reference to the accompanying drawings, wherein:

FIG. 5 is a schematic depiction of twelve alternative oligonucleotide probe pairs used for amplification of nucleic acid sequences according to the method of the present invention.

FIG. 22 shows a case in which ultimate chemical functionality groups which are ones that distore the tertiary structure of the hybridized sequences to a permissible degree that enables the use of oligonucleotide probe complementary pairs that are of the same length are used in which the modified nucleotides themselves, to which the chemical functionality groups are conjugated, act as the amplification discriminative sequences.

DESCRIPTION OF THE PREFERRED EMBODIMENTS

Figure 1:
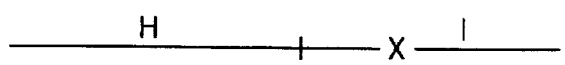
FIG. 1 is a schematic depiction of the oligonucleotide probes used in the chemical amplification reaction (CAR) method of the prior art.
Figure 1:
Figure 1:
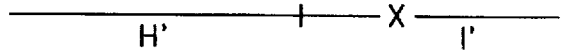
Figure 1:
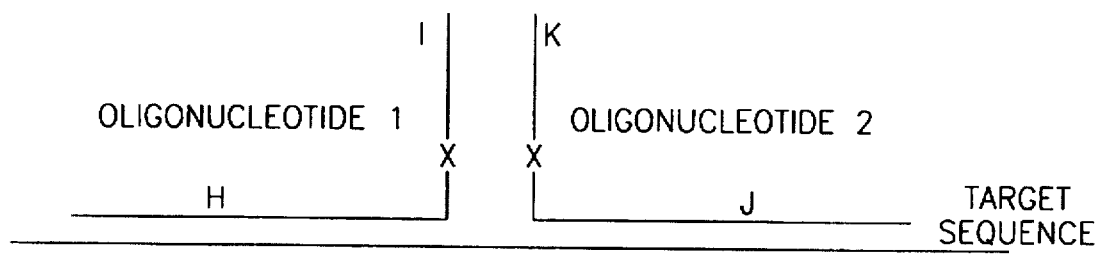
Figure 2:
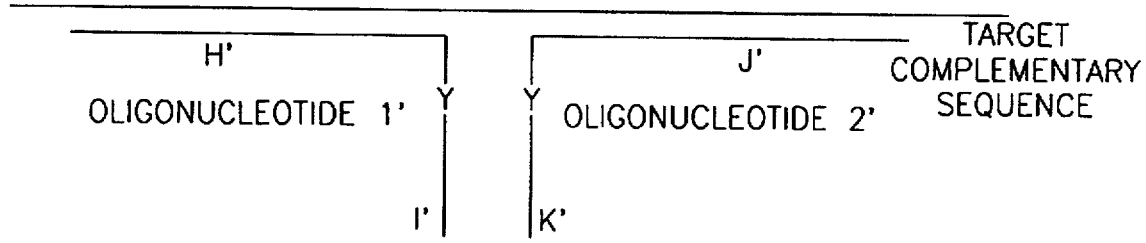
FIG. 2 is a schematic depiction of the hybridizations characterizing oligonucleotide probes of the CAR method when contacted with a target nucleic acid sequence and a target nucleic acid complementary sequence.

The present invention is of a novel non-enzymatic method for amplifying and detecting existing target nucleic acid sequences in a test sample and of kits for use in implementing the method. The method of the present invention may employ both an amplification procedure and a detection procedure and is also useful in the detection of minute sequence alterations such as point mutations, i.e. a single base pair alteration.

The principles and operation of a method according to the present invention may be better understood with reference to the drawings and the accompanying description.

The present invention will be described in detail with emphasis on a method for identifying the presence of a target nucleic acid sequence in an examined sample and on a method for identifying minute sequence alterations in genes, which alterations are associated with genetic disorders. While the later applications of the method of the invention are presently preferred, this is by no means the only applications of the invention as will no doubt be appreciated by those skilled in the art. For example, the method has various other applications including, but not limited to, the detection of specific genetic sequences in a sample such as those associated with certain genetic polymorphisms, such as, for example, in the HLA locus; in testing of paternity and in forensic medicine; and in the diagnosis of certain cancers.

As used herein, the following terms have their definitions designated below.

Target Nucleic Acid Sequence

The process of the present invention can produce a geometric amplification of a target nucleic acid sequence, provided that at least part of the nucleotide sequence is known in sufficient detail that complementary oligonucleotide probe pairs can be synthesized. The "amplification" that is achieved through the methods of the present invention denotes an increase in the amount of desired nucleic acid molecules present in a reaction vessel. "Substantial amplification" refers to greater than about 100-fold amplification. The target nucleic acid sequence that is amplified by the method of the present invention may be single-stranded or double-stranded DNA, single-stranded or double-stranded RNA, single-stranded or double-stranded protein nucleic acid (PNA) or a hybrid of DNA, RNA and/or PNA. Since no enzymes are used in the amplification process of the present invention, therefore, the target sequence may be in a purified or a non-purified form. The sample of nucleic acids can be drawn from any source and may be natural or synthetic. The sample of nucleic acids may be made up of deoxyribonucleic acids, ribonucleic acids, or copolymers of deoxyribonucleic acid and ribonucleic acid or combinations thereof. The nucleic acid of interest can be synthesized enzymatically in vitro, or be synthesized non-enzymatically. The sample containing the nucleic acid or acids of interest can also comprise extragenomic DNA from an organism, RNA transcripts thereof, or cDNA prepared from RNA transcripts thereof. Also, the nucleic acid or acids of interest can be synthesized by the polymerase or ligase chain reaction.

The cells that contain the target nucleic acid sequence, could be lysed in the presence of the reagents used in implementing the method. Typically, the sample is treated to a sufficient degree such that extraneous materials which might otherwise interfere with amplification of the nucleic acid are removed. For example, the preparation of a serum sample for analysis using the method of the invention may consist incubation of the serum sample for 1 hr. at 70° C. in the presence of proteinase K at a concentration of 2.5 mg/ml in 25 ml MOPS (pH 6.5), 2.5 mM EDTA and 0.5% SDS. Following this treatment, the sample is ready for amplification without any further purification steps.

The nucleic acid sample contains the specific nucleotide sequences to which the oligonucleotide probes hybridize. If a target sequence is double-stranded, it contains a target sequence and its complement called the target complementary sequence. The target sequence can be as short as twelve nucleotides, but preferably contains at least sixteen nucleotides and more preferably at least twenty nucleotides. There is no maximum number of nucleotides in the target sequence or target complementary sequence, which can constitute either a portion of the nucleic acid sample or the entire nucleic acid sample.

Among the molecules which may be amplified using the invented method included are genetic material in the form of DNA or RNA obtained from any naturally occurring prokaryotes such as for example, pathogenic or non-pathogenic bacteria including but not limited to species of Escherichia, Salmonella, Clostridium, Chlamydia, etc.; eukariots such as for example, protozoans and parasites, fungi, yeast, higher plants, lower and higher animals, including mammals and humans and cells in tissue culture; or viruses such as for example, Herpes viruses, HIV, influenza virus, Epstein-Barr virus, hepatitis B virus, etc. The nucleic acid molecules can also be any nucleic acid molecule which has been or can be chemically or enzymatically synthesized.

DNA or RNA from these sources may, for example, be found in samples of a bodily fluid from an animal, including a human, such as, but not limited to, blood, urine, lymphatic fluid, synovial fluid, bile, phlegm, saliva, menstrual fluid and semen. In addition, samples containing DNA or RNA may, for example, be found in fluids from a plant, such as, but not limited to, xylem fluid, phloem fluid and plant exudates. Samples containing DNA or RNA may, for example also be found in non-living sources such as, but not limited to, food, sewage, forensic samples, lakes, reservoirs, rivers and oceans.

Although the nucleic acid target molecule which is to be amplified by the method of the present invention may be in either a double-stranded or a single-stranded form, in the case where the nucleic acid target molecule is double-stranded it is preferably first treated by a denaturation agent to render the two strands into a single-stranded, or partially single-stranded form, at the start of the amplification reaction, by methods known in the art such as heating, alkali treatment, or by enzymatic methods. General methods for accomplishing this treatment are provided by Sambrook, J. et al. In: *Molecular Cloning: A Laboratory Manual* Cold Spring Harbor Laboratory Press, Cold Spring Harbor, N.Y. (1989).

Complementarity

As used herein, two sequences are said to "hybridize" to one another if they are capable of forming an anti-parallel double-stranded nucleic acid structure. Two nucleic acid molecules are said to be "complementary" if they can hybridize to one another with sufficient stability to permit them to remain annealed to one another under at least conventional "low stringency" conditions. (These conditions are described in Sambrook, as above).

Thus, two complementary molecules need not exhibit precise complementarity, but need only be sufficiently complementary in sequence to be able to form a stable double-stranded structure. Departures from complete complementarity are therefore permissible, as long as such departures are not sufficient to completely preclude hybridization to form a double-stranded structure.

Oligonucleotide Probe Complement Pair

Figure 4:
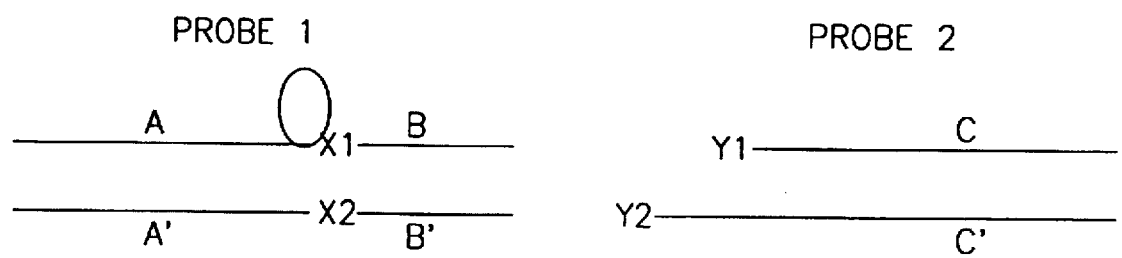
FIG. 4 is a schematic depiction of oligonucleotide probe pairs used for amplification of nucleic acid sequences according to the method of the present invention.

The term "oligonucleotide probe complement pair" as used herein refers to two different oligonucleotide probes designated, for example, oligonucleotide probe 1 and oligonucleotide probe 1' or oligonucleotide probe 2 and oligonucleotide probe 2', as shown in FIG. 4. As will shortly be demonstrated in details, oligonucleotide probes 1 and 1', oligonucleotide probes 2 and 2', oligonucleotide probes 3 and 3' as well as oligonucleotide probes 4 and 4', share sequence regions which are complementary. Each oligonucleotide probe of a complement pair of oligonucleotide probes can be equal or preferably, as shown in the Figure, unequal in length to its co-member. It should be understood that more that two oligonucleotide probe complement pairs per target sequence or target complementary sequence could be used during the execution of the method of the present invention.

Oligonucleotide Probe Pair

The term "oligonucleotide probe pair", as used herein, refers to the grouping of oligonucleotide probes 1 and 2 as a first "oligonucleotide probe pair", the grouping of oligonucleotide probes 1' and 2' as a second "oligonucleotide probe pair", the grouping of oligonucleotide probes 3 and 4 as a third "oligonucleotide probe pair" and the grouping of oligonucleotide probes 3' and 4' as a fourth "oligonucleotide probe pair".

The oligonucleotide probes are preferably constructed from deoxyribonucleotides, though ribonucleotides and nucleotide analogs such as but not limited to protein nucleic acid (PNA), are acceptable substitutes.

Referring to the first oligonucleotide probe complement pair in FIG. 4, oligonucleotide probe 1 has a targeting sequence A and a protecting sequence B; Oligonucleotide probe 1' has a targeting sequence A' and a protecting sequence B'; oligonucleotide probe 2 has a targeting sequence C; and oligonucleotide probe 2' has a targeting sequence C'. X and Y are chemical functionality groups, wherein X and Y groups could form a chemical bond. The oval shape, as will shortly be described, is a single-stranded looput, is a part of targeting sequence A and is complementary to the single-stranded sequence portion of targeting sequence C'.

As is understood by ones with skills in the art, twelve slightly different versions exist for the sequences arrangement among these oligonucleotide probes. These versions are shown in FIG. 5 and include: (1) oligonucleotide probe 1 has a targeting sequence A and a protecting sequence B; oligonucleotide probe 1' has a targeting sequence A' which is shorter than targeting sequence A of oligonucleotide probe 1; oligonucleotide probe 2 has a targeting sequence C; oligonucleotide probe 2' has a targeting sequence C' which is longer than targeting sequence C of oligonucleotide probe 2 and a protecting sequence B'; (2) oligonucleotide probe 1 has a targeting sequence A and a protecting sequence B; oligonucleotide probe 1' has a targeting sequence A' which is longer than targeting sequence A of oligonucleotide probe 1; oligonucleotide probe 2 has a targeting sequence C;

17 oligonucleotide probe 2' has a targeting sequence C' which is shorter than targeting sequence C of oligonucleotide probe 2 and a protecting sequence B'; (3) oligonucleotide probe 1 has a targeting sequence A and a protecting sequence B; oligonucleotide probe 1' has a targeting sequence A' which equals in length to targeting sequence A of oligonucleotide probe 1; oligonucleotide probe 2 has a targeting sequence C; oligonucleotide probe 2' has a targeting sequence C' which equals in length to targeting sequence C of oligonucleotide probe 2 and a protecting sequence B'; (4) oligonucleotide probe 1 has a targeting sequence A and a protecting sequence B; oligonucleotide probe 1' has a targeting sequence A' which is shorter than targeting sequence A of oligonucleotide probe 1 and a protecting sequence B'; oligonucleotide probe 2 has a targeting sequence C; oligonucleotide probe 2' has a targeting sequence C' which is longer than targeting sequence C of oligonucleotide probe 2; (5) oligonucleotide probe 1 has a targeting sequence A and a protecting sequence B; oligonucleotide probe 1' has a targeting sequence A' which is longer than targeting sequence A of oligonucleotide probe 1 and a protecting sequence B'; oligonucleotide probe 2 has a targeting sequence C; oligonucleotide probe 2' has a targeting sequence C' which is shorter than targeting sequence C of oligonucleotide probe 2; (6) oligonucleotide probe 1 has a targeting sequence A and a protecting sequence B; oligonucleotide probe 1' has a targeting sequence A' which equals in length to targeting sequence A of oligonucleotide probe 1 and a protecting sequence B'; oligonucleotide probe 2 has a targeting sequence C; oligonucleotide probe 2' has a targeting sequence C' which equals in length to targeting sequence C of oligonucleotide probe 2; (7) oligonucleotide probe 1 has a targeting sequence A; oligonucleotide probe 1' has a targeting sequence A' which is shorter than sequence A of oligonucleotide probe 1; oligonucleotide probe 2 has a targeting sequence C and a protecting sequence B; oligonucleotide probe 2' has a targeting sequence C' which is longer than targeting sequence C of oligonucleotide probe 2 and a protecting sequence B'; (8) oligonucleotide probe 1 has a targeting sequence A; oligonucleotide probe 1' has a targeting sequence A' which is longer than sequence A of oligonucleotide probe 1; oligonucleotide probe 2 has a targeting sequence C and a protecting sequence B; oligonucleotide probe 2' has a targeting sequence C' which is shorter than targeting sequence C of oligonucleotide probe 2 and a protecting sequence B'; (9) oligonucleotide probe 1 has a targeting sequence A; oligonucleotide probe 1' has a targeting sequence A' which equals in length to sequence A of oligonucleotide probe 1; oligonucleotide probe 2 has a targeting sequence C and a protecting sequence B; oligonucleotide probe 2' has a targeting sequence C' which equals in length to targeting sequence C of oligonucleotide probe 2 and a protecting sequence B'; (10) oligonucleotide probe 1 has a targeting sequence A; oligonucleotide probe 1' has a targeting sequence A' which is shorter than targeting sequence A of oligonucleotide probe 1 and a protecting sequence B; oligonucleotide probe 2 has a targeting sequence C and a protecting sequence B'; oligonucleotide probe 2' has a targeting sequence C' which is longer than targeting sequence C of oligonucleotide probe 2; (11) oligonucleotide probe 1 has a targeting sequence A; oligonucleotide probe 1' has a targeting sequence A' which is longer than targeting sequence A of oligonucleotide probe 1 and a protecting sequence B; oligonucleotide probe 2 has a targeting sequence C and a protecting sequence B'; oligonucleotide probe 2' has a targeting sequence C' which is shorter than targeting sequence C of oligonucleotide probe 2; (12) oligonucleotide probe 1 has a targeting sequence A;

18 oligonucleotide probe 1' has a targeting sequence A' which equals in length to targeting sequence A of oligonucleotide probe 1 and a protecting sequence B; oligonucleotide probe 2 has a targeting sequence C and a protecting sequence B'; oligonucleotide probe 2' has a targeting sequence C' which equals in length to targeting sequence C of oligonucleotide probe 2. It is understood that similar versions exist for oligonucleotide probes 3, 3', 4 and 4' wherein oligonucleotide probe 3 is similar to oligonucleotide probe 1; oligonucleotide probe 4 is similar to oligonucleotide probe 2; oligonucleotide probe 3' is similar to oligonucleotide probe 1'; and oligonucleotide probe 4' is similar to oligonucleotide probe 2';

As a matter of convenience all further descriptions will regard option 4 described above, in which oligonucleotide probe 1 has a targeting sequence A and a protecting sequence B; Oligonucleotide probe 1' has a targeting sequence A' and a protecting sequence B'; oligonucleotide probe 2 has a targeting sequence C; and oligonucleotide probe 2' has a targeting sequence C'.

Figure 6:
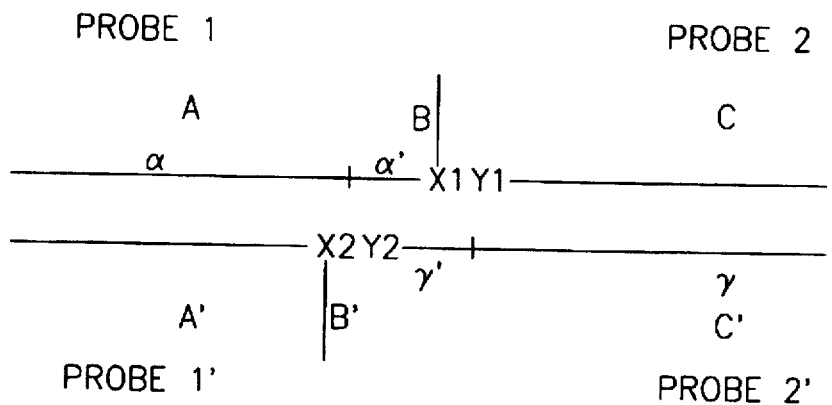
FIG. 6 is a schematic depiction of the built-up of the oligonucleotide probes used for amplification of nucleic acid sequences according to the method of the present invention.

As further detailed in FIG. 6, targeting sequence A of oligonucleotide probe 1 includes a long part $\alpha$ and a short part $\alpha'$ (the border between part $\alpha$ and part $\alpha'$ is denoted by a vertical line in the Figure); targeting sequence C' of oligonucleotide probe 2' includes a long part $\gamma$ and a short part $\gamma'$ (the border between part $\gamma$ and part $\gamma'$ is denoted by a vertical line in the Figure); part $\alpha$ of targeting sequence A of oligonucleotide probe 1 and targeting sequence A' of oligonucleotide probe 1' are complementary to each other; part $\alpha'$ of targeting sequence A of oligonucleotide probe 1 and part $\gamma'$ of targeting sequence C' of oligonucleotide probe 2' are complementary to each other; targeting sequence C of oligonucleotide probe 2 and part $\gamma$ of targeting sequence C' of oligonucleotide probe 2' are complementary to each other; part $\gamma'$ of targeting sequence C' of oligonucleotide probe 2' and part $\gamma'$ of sequence A of oligonucleotide probe 1 are complementary to each other. X and Y are chemical functionality groups, wherein X and Y groups could form a chemical bond. A similar structure characterizes oligonucleotide probes 3, 3', 4 and 4'. For simplicity, some of the descriptions herein will refer only to oligonucleotide probes 1, 2, 1', and 2' whereas these descriptions suit also oligonucleotide probes 3, 4, 3' and 4', except if noted otherwise.

Figure 7:
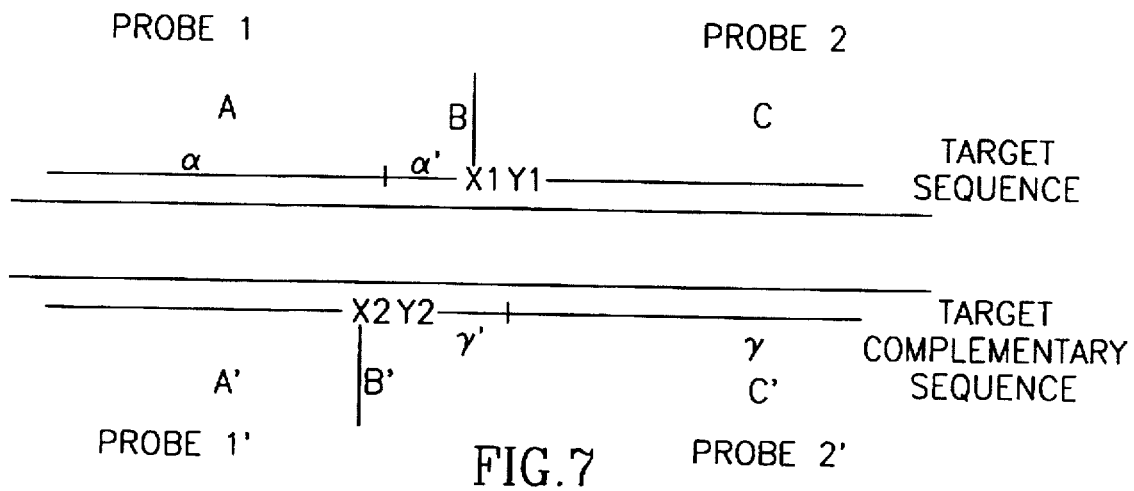
FIG. 7 is a schematic depiction of the hybridizations characterizing oligonucleotide probes of the method of the present invention, when contacted with a target nucleic acid sequence and a target nucleic acid complementary sequence.

As shown in the FIG. 7, if a target nucleic acid sequence is present in a test sample, targeting sequence A and targeting sequence C are either entirely complementary or are sufficiently complementary to adjacent regions of the target sequence to form a stable hybrid under selected hybridization conditions. If a strand complementary to a target nucleic acid sequence is present in a test sample, targeting sequence A' and targeting sequence C' are either entirely complementary to the target complementary sequence or are sufficiently complementary to adjacent regions of the target complementary sequence to form a stable hybrid under selected hybridization conditions.

The terms "adjacent regions of a target sequence" or "adjacent regions of a target complementary sequence" as used herein refer to sequences in these nucleic acid molecules that are preferably immediately abutting and juxtaposed to one another or alternatively are separated by one or two nucleotide bases.

The term "abutting" as used herein refer to targeting sequences A and C or A' and C' which are not forming a chemical bond between their 3' end and 5' end positions, as in the enzymatic ligation, but may form chemical bonds between the X and Y chemical functionality groups, wherein X and Y groups could form a chemical bond as will be detailed below.

The minimum number of nucleotides of targeting sequences A and A' and of targeting sequences C and C' of the relevant oligonucleotide probes is the smallest number that gives sufficient selectivity in the amplification and detection process of the present invention. For example, these sequences may include at least six, preferably at least twelve and more preferably at least twenty deoxyribonucleotides ribonucleotides or their analogs.

The maximum length of targeting sequences A and A' and of targeting sequences C and C' of the relevant oligonucleotide probes is limited only by the length of the target nucleic acid sequence in the test sample. These sequences should be of sufficient length to form a stable hybrid with the target sequence, but are preferably not too long to require excessive hybridization times. Some suitable maximum lengths of these sequences are 200 nucleotides, preferably 150 nucleotides and more preferably 100 nucleotides. Some suitable lengths of these sequences are 6–100 nucleotides, preferably 10–70 nucleotides, more preferably 16–50 nucleotides and most preferably 18–30 nucleotides.

Protecting sequences B and B', may not be, but preferably are complementary to each other. Protecting sequences B and B' are preferably not complementary to any nucleic acid sequence existing in the examined nucleic acid sample. Protecting sequences B and B' may be consisted of a random universal sequence but they may also differ in sequence from one oligonucleotide probe molecule to the other.

Protecting sequences D and D', may not be, but preferably are complementary to each other. Protecting sequences D and D' are preferably not complementary to any nucleic acid sequence existing in the examined nucleic acid sample. Protecting sequences D and D' may be consisted of a random universal sequence but they may also differ in sequence from one oligonucleotide probe molecule to the other. In some of the applications to be described herein protecting sequences B and D and protecting sequences B' and D' may be identical.

Protecting sequences of any oligonucleotide probe are designed so they do not hybridize to the target sequence when the targeting sequences of the oligonucleotide probes have hybridized to the target sequence or to the target complementary sequence. Therefore, for example, protecting sequence B is unhybridized when targeting sequence A and targeting sequence C hybridize to adjacent portions of the target sequence. Likewise, protecting sequence B' is unhybridized when targeting sequence A' and targeting sequence C' hybridize to adjacent portions of the target complementary sequence. These unhybridized single-stranded sequences are used for an in situ detection procedure as will be emphasized herein.

The design of the oligonucleotide probes built-up is preferably made so that the reaction point between the chemical functionality groups of targeting sequences A and C, is located apart from the reaction point between the chemical functionality groups of targeting sequences A' and C'. The $\alpha'$ part of targeting sequence A and the $\gamma'$ part of targeting sequence C' should be long enough to avoid failure of amplification due to distortion of the tertiary structure of the hybridized sequences imposed by the chemical functionality groups themselves after the formation of a chemical bond between them. The ultimate chemical functionality groups would, therefore, be ones that distore the tertiary structure of the hybridized sequences to a permissible degree that enables the use of oligonucleotide probe complementary pairs which are of the same length, that is the length of targeting sequence A equals that of targeting sequence A' and that of targeting sequence C equals that of targeting sequence C'. In these oligonucleotide probes the nucleotide content of parts $\alpha'$ and $\gamma'$ equal zero.

Figure 8:
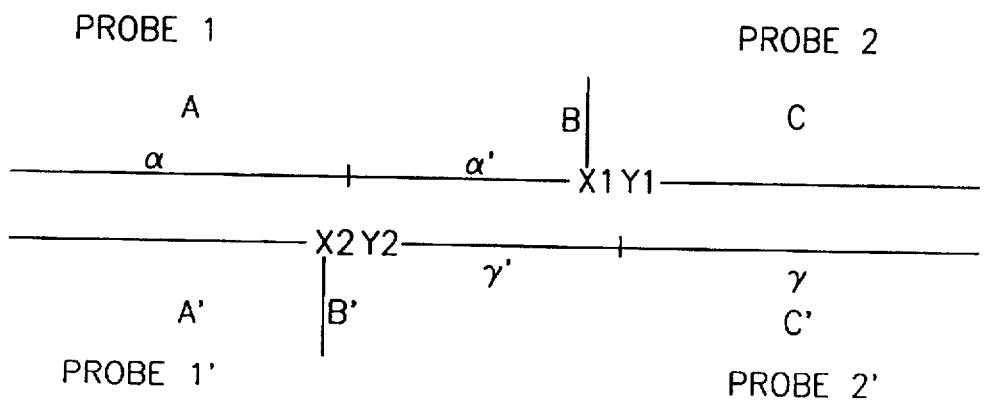
FIG. 8 is a schematic depiction of a structure of a high thermodynamic stability the oligonucleotide probes used under the method of the present invention.

The maximum length of an $\alpha'$ sequence of targeting sequence A and of an $\gamma'$ sequence of targeting sequence C' depends on the length ratio between the $\alpha$ and the $\alpha'$ sequences and the $\gamma$ and the $\gamma'$ sequences, respectively. $\alpha'$ and $\gamma'$ sequences which are too long might lead to the undesired formation of template independent amplification products through the formation of a stable structure of the type shown in FIG. 8.

There is no length limitations regarding protecting sequences B, B', D and D'. This enables a versatile use of these sequences for detection of joined oligonucleotide products as will be described herein.

Figure 9:
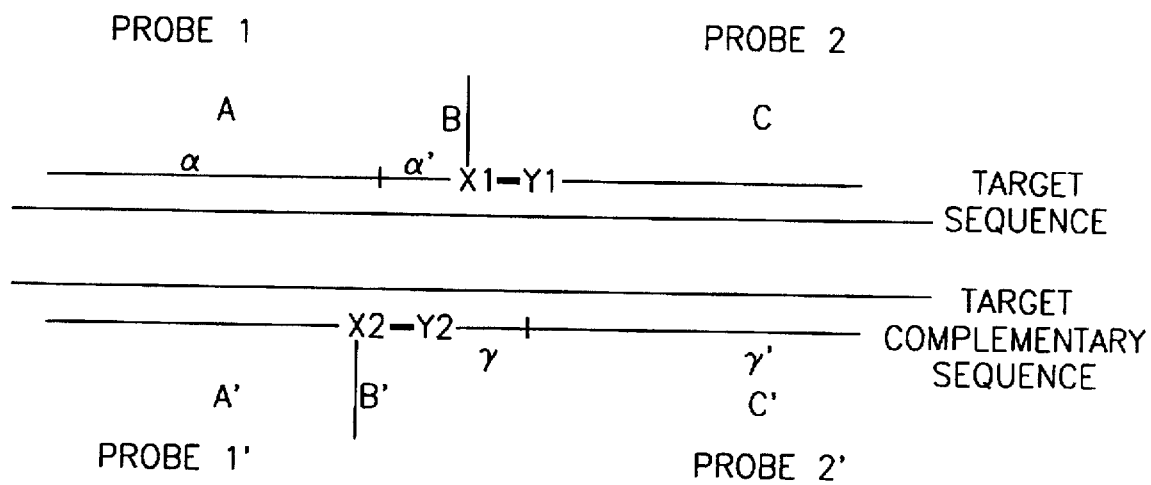
FIG. 9 is a schematic depiction of the formation of joined oligonucleotide products during the amplification of a nucleic acid sequence according to the method of the present invention.
Figure 10:
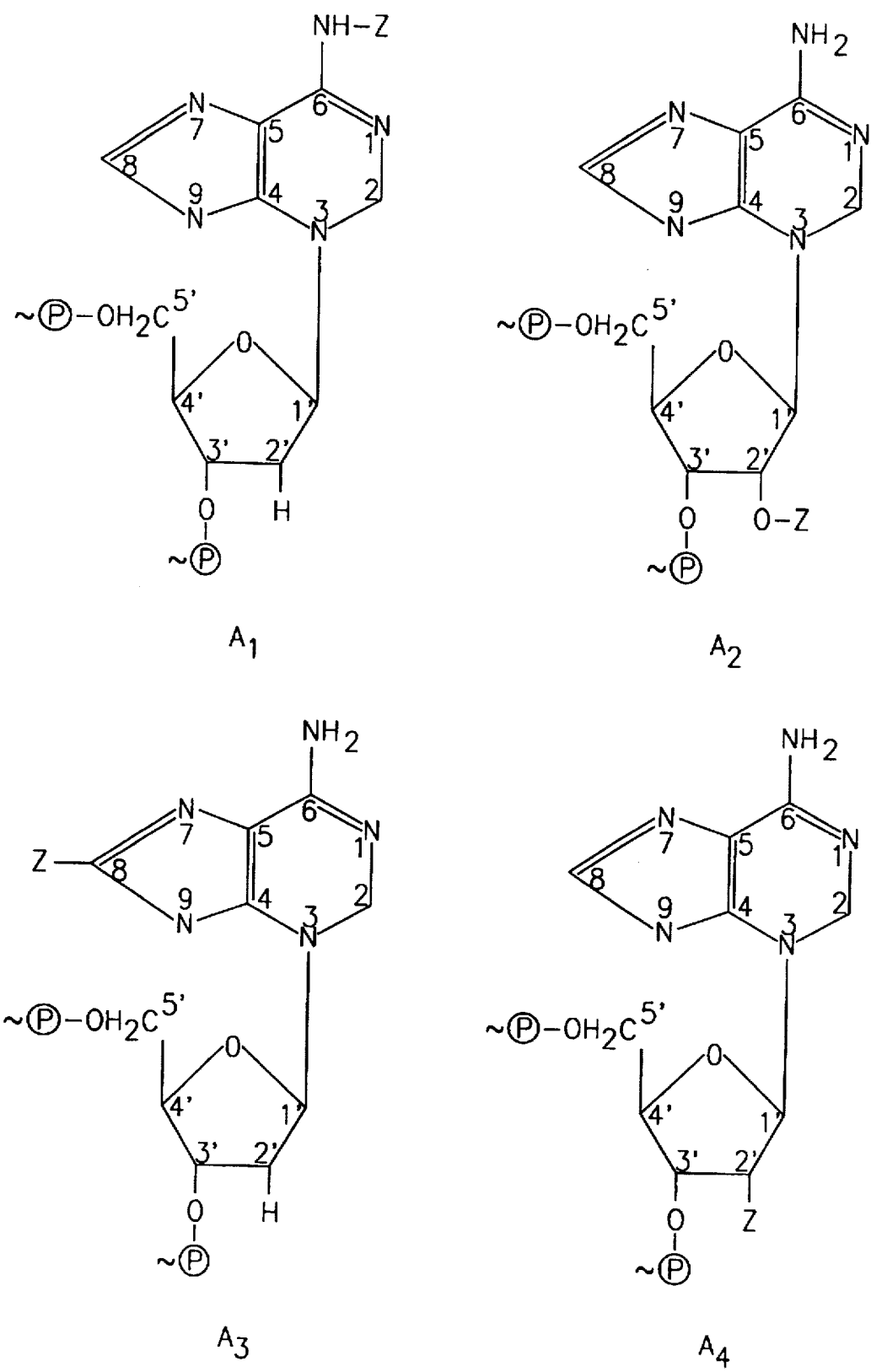
FIG. 10 shows adenine derivatives A1, A2, A3 and A4 modified with a chemical functionality group Z.
Figure 11:
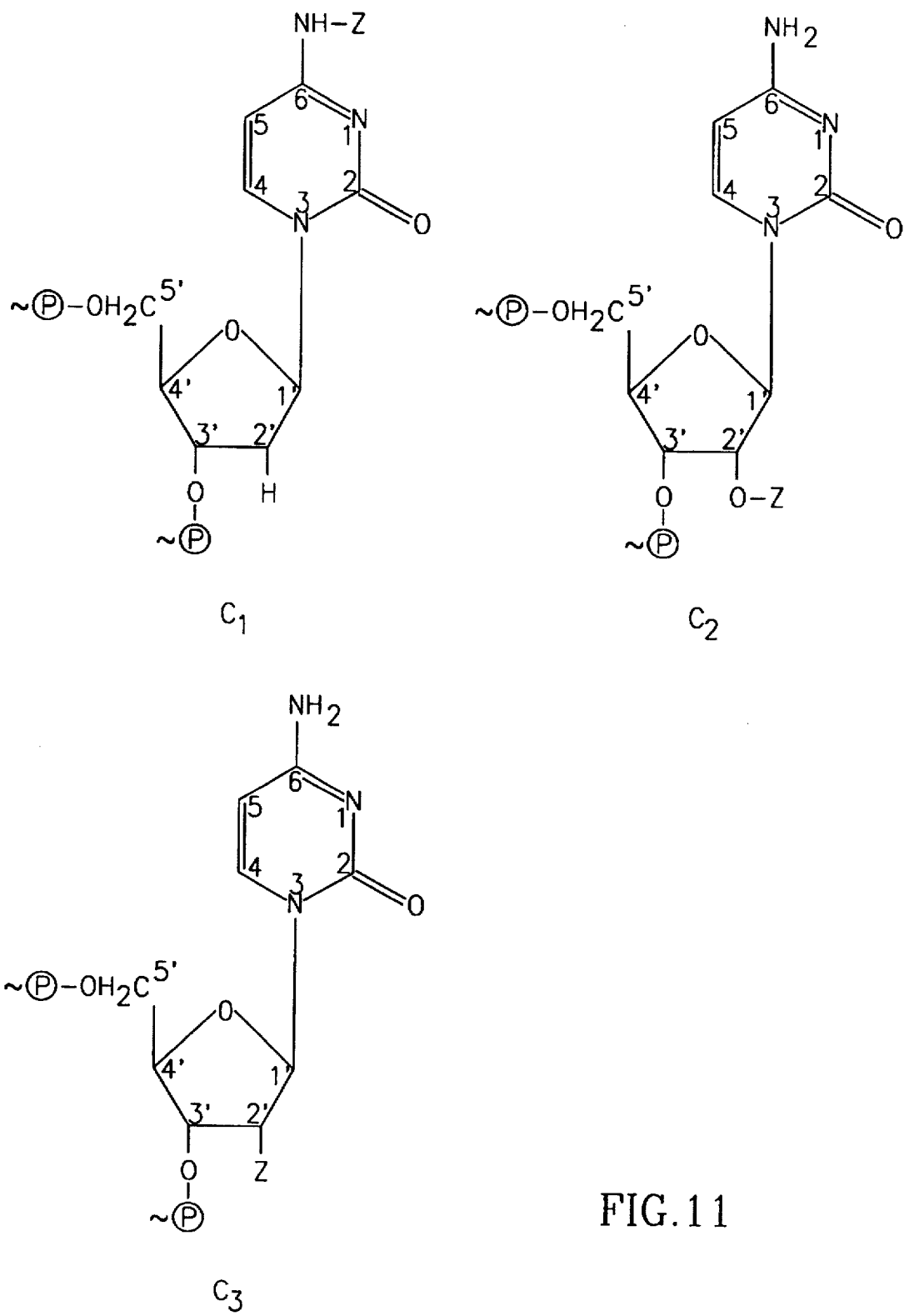
FIG. 11 shows cytidine derivatives C1, C2, C3 and C4 modified with a chemical functionality group Z.
Figure 12:
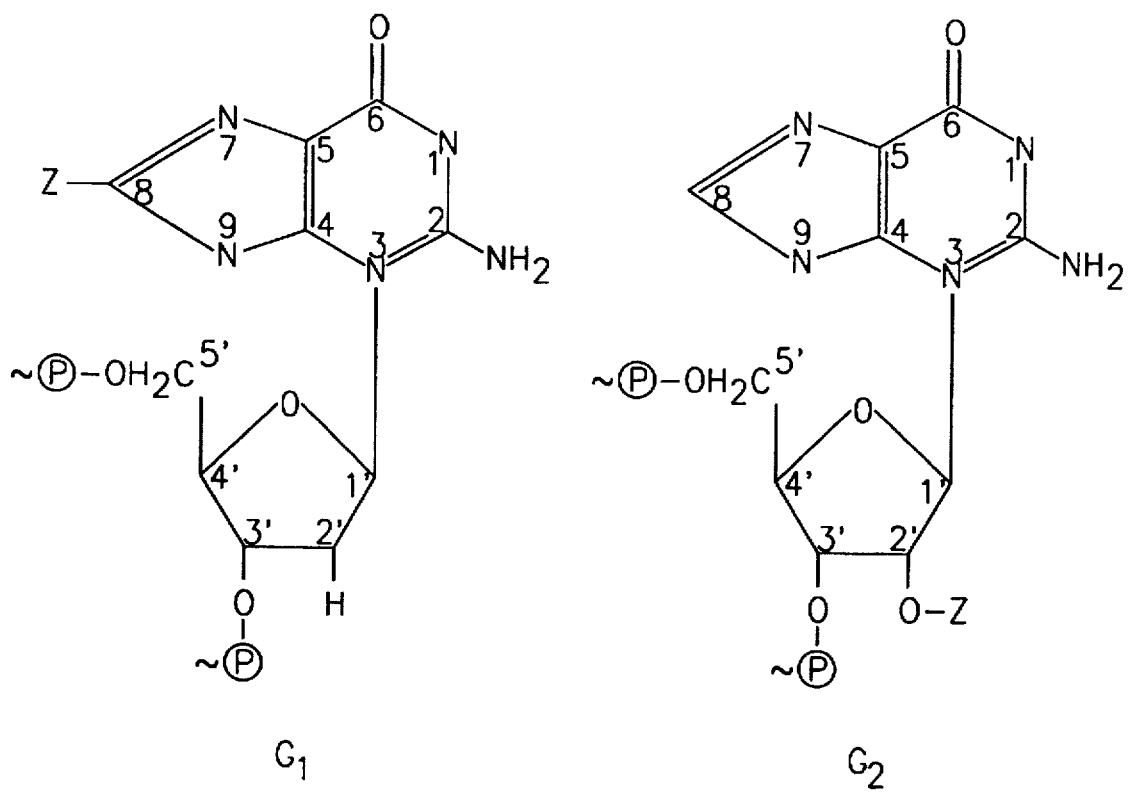
FIG. 12 shows guanine derivatives G1, G2, G3 and G4 modified with a chemical functionality group Z.
Figure 12:
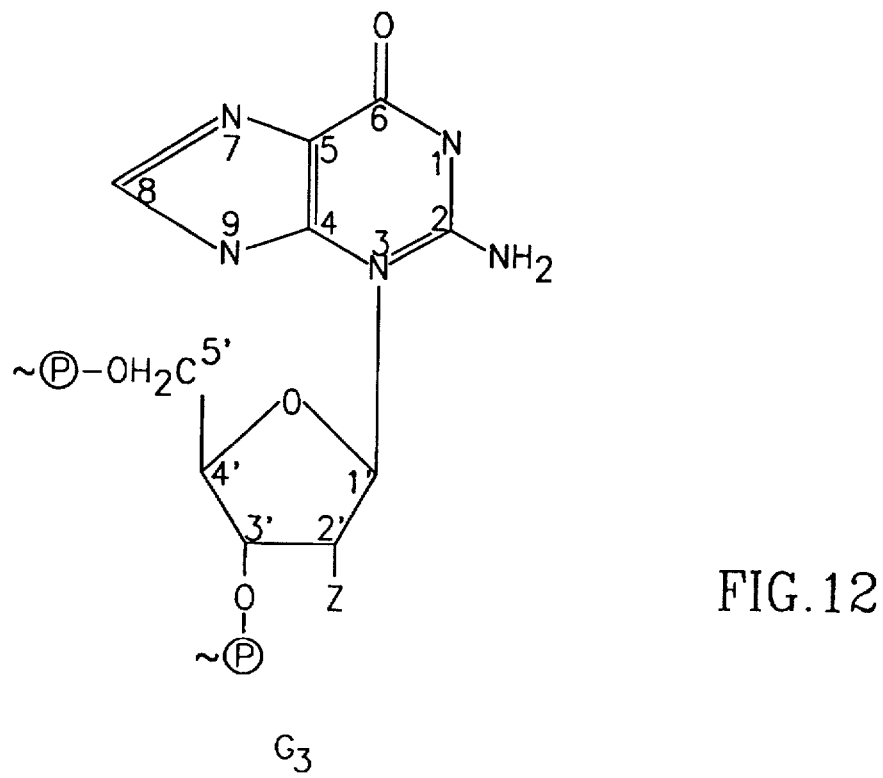
Figure 13:
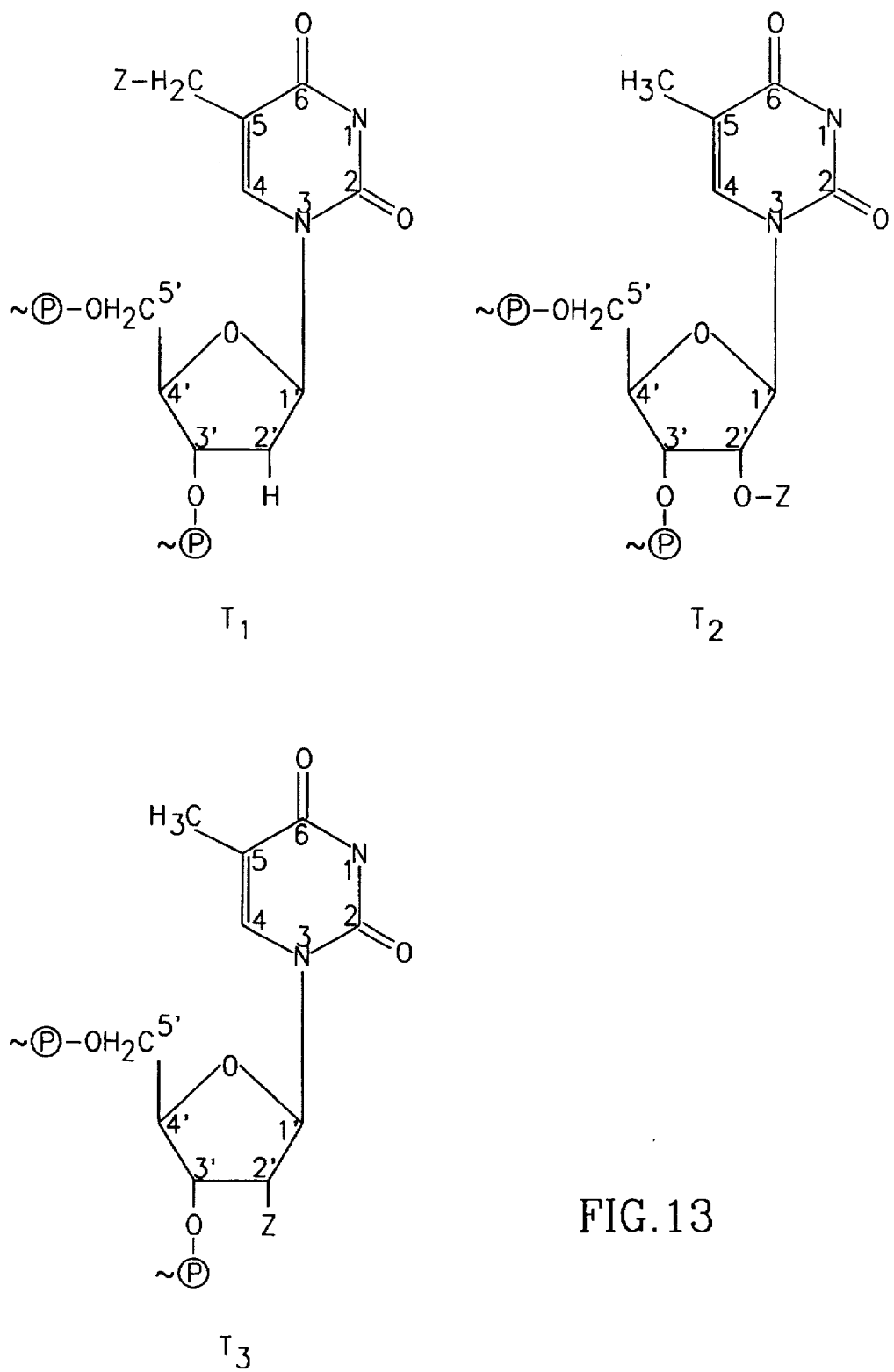
FIG. 13 shows thymidine derivatives T1, T2, T3 and T4 modified with a chemical functionality group Z.
Figure 14:
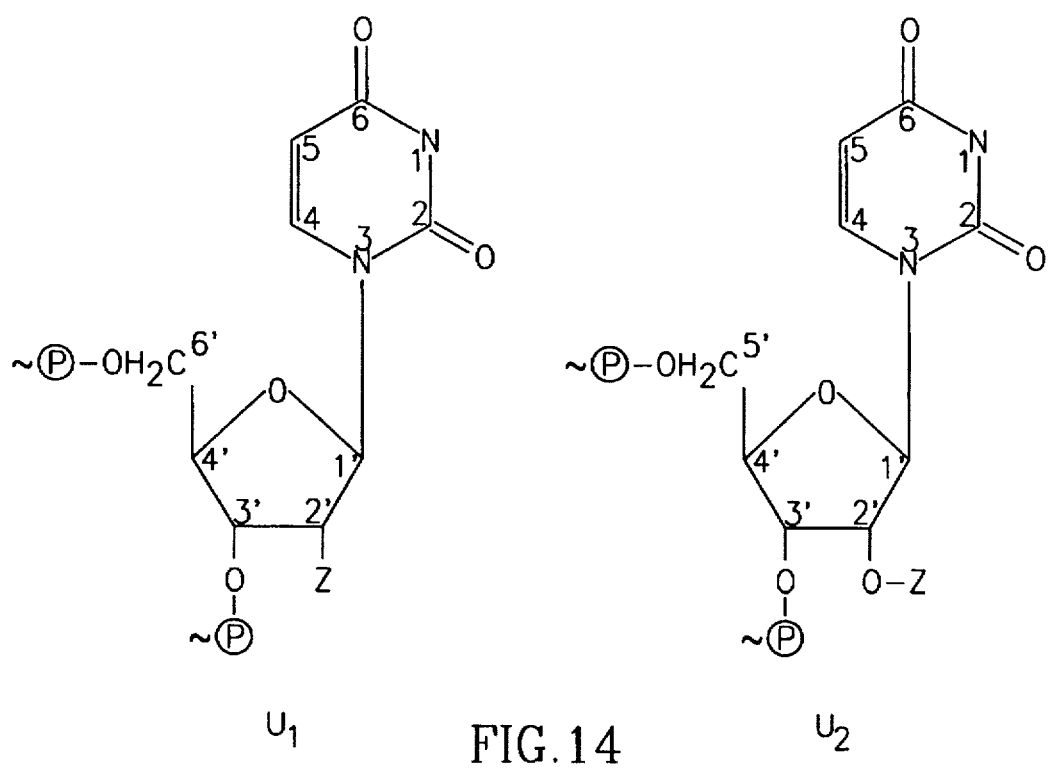
FIG. 14 shows uridine derivatives U1, U2, U3 and U4 modified with a chemical functionality group Z.

At the end of targeting sequence A, in the junction between targeting sequence A and protecting sequence B of oligonucleotide probe 1 and at the end of targeting sequence A', in the junction between targeting sequence A' and protecting sequence B' of oligonucleotide probe 1', located are chemical functionality groups, designated as X1 and X2, respectively. To each of the targeting sequences C of oligonucleotide probe 2 and C' of oligonucleotide probe 2', attached is a chemical functionality group, designated Y1 and Y2, respectively. These chemical functionality groups are covalently attached to the sugar and/or base moieties of one of the nucleotides in each sequence. When targeting sequences A and C of oligonucleotide probes 1 and 2, respectively, or targeting sequences A' and C' of oligonucleotide probes 1' and 2', respectively, are hybridized to the target nucleic acid sequence or the target nucleic acid complementary sequence, the chemical functionality groups X1 and Y1, and X2 and Y2, respectively, react chemically to form a chemical bond that joins oligonucleotide probes 1 and 2 and oligonucleotide probes 1' and 2', respectively, to form a first and a second joined oligonucleotide products of the form shown in FIG. 9. Oligonucleotide probes 3 and 4 and oligonucleotide probes 3' and 4' form joined oligonucleotide products in a similar fashion.

When the target nucleic acid sequence and the target nucleic acid complementary sequence do not exist in the examined nucleic acid sample, the nucleotides to which the chemical functionality group X1 and X2 are attached and the neighboring nucleotide or nucleotides in the relevant oligonucleotide probe protect the chemical functionality groups from reacting with the Y1 and Y2 chemical functionality group on another oligonucleotide probe, respectively.

The oligonucleotide probe pairs may be synthesized chemically from the four nucleotides in whole or in part by methods known in the art. Such methods include those described by Caruthers in Science 230, 281–285 (1985) and by Beaucage, et al., in Tetrahedron Letters 22, 1859–1862 (1981).

Template Sequence

The term "template sequence" as used herein refers to nucleic acid sequence to which a plurality of oligonucleotide probe pairs or a plurality of detection oligonucleotide probes hybridize. In the first cycle of the amplification procedure as will be detailed herein, the target nucleic acid sequence and the target nucleic acid complementary sequence act as template sequences. In subsequent cycles of the amplification procedure and in the detection procedure as will be detailed herein, joined oligonucleotide products serve as template sequences as well.

Amplification Product

The term "amplification product" as used herein refers to the nucleic acid sequences which are produced from chemically joining oligonucleotide probe pairs to each other to form joined sequences.

Spurious Amplification By-Product

The term "spurious amplification by-product" as used herein, is a product, resulting from a reaction between X and Y chemical functionality groups, leading to the joining of the oligonucleotide probes belonging to an oligonucleotide probe pair to form an joined oligonucleotide product, which is target nucleic acid sequence or target nucleic acid complementary sequence hybridization independent.

Proximity Label

The term "proximity label" as used herein, is one of at least two labels which interact with each other to produce a detectable signal where the proximity labels are brought together. Typically, a first proximity label is used in combination with a corresponding second proximity label in order to produce a detectable signal under conditions wherein the two proximity labels are proximate to each other.

Chemical Functionality Groups

Chemical functionality groups X and Y (X=X1, X2, X3 or X4 and Y=Y1, Y2, Y3 or Y4) are pairs of atoms and/or groups that are reactive with each other (X1 with Y1; X2 with Y2; X3 with Y3; and X4 with Y4) to form chemical bonds when they are brought into close proximity with one another by hybridization of targeting sequences A and targeting sequences C to a target nucleic acid sequence, or by hybridization of targeting sequences A' and targeting sequences C' to a target nucleic acid complement sequence. The distance between pairs of chemical functionality groups (e.g. X1 and Y1) should be approximately 4A° or less and in the appropriate orientation in order for a chemical reaction between the groups to take place.

A chemical functionality group of an X1 type is attached to the base or sugar moiety of a nucleotide positioned in the junction of targeting sequence A and protecting sequence B of oligonucleotide probe 1; an X2 type is attached to the base or sugar moiety of a nucleotide positioned in the junction of targeting sequence A' and protecting sequence B' of oligonucleotide probe 1'; an X3 type is attached to the base or sugar moiety of a nucleotide positioned in the junction of targeting sequence A and protecting sequence D of oligonucleotide probe 3; an X4 type is attached to the base or sugar moiety of a nucleotide positioned in the junction of targeting sequence A' and protecting sequence D' of oligonucleotide probe 3'; Y1 and Y2 types are attached to the end of targeting sequences C and C' of oligonucleotide probes 2 and 2', respectively; and Y3 and Y4 types are attached to the end of targeting sequences C and C' of oligonucleotide probes 4 and 4', respectively.

Chemical functionality groups X1, X2, X3 and X4 can be of a same or of a different chemical nature; and chemical functionality groups Y1, Y2, Y3 and Y4 can be of a same or of a different chemical nature, as long as the members of a chemical functionality group pair (e.g. X1 and Y1) can form a chemical bond between them when targeting sequences A and C, and, A' and C', of the relevant oligonucleotide probes are hybridized to the target nucleic acid sequence and the target nucleic acid complementary sequence, respectively.

A chemical functionality group is covalently attached to a nucleotide at a sterically tolerant site which is defined as a position on a nucleotide base or sugar moiety at which a chemical functionality group can be attached without causing significant interference with hybridization of targeting sequences A and targeting sequences C of oligonucleotide probes 1 and 3, and oligonucleotide probes 2 and 4, respectively, to the target sequences or of targeting sequences A' and targeting sequences C' of oligonucleotide probes 1' and 3', and oligonucleotide probes 2' and 4', respectively, to the target complementary sequences. Sterically tolerant sites include positions on the purine and pyrimidine bases and polyvalent heteroatoms of the base or ribose portion of a nucleotide or a nucleotide analog.

Examples of sterically tolerant sites include the methyl group attached to the C-5 position of thymidine, the amino group attached to the C-6 position of adenine or cytidine, the C-8 position of adenine or guanine, the C-2' position of the ribose ring of each type of nucleotide and the hydroxyl group attached to the C-2' position of the ribose ring of a ribonucleotide.

The modification of the purine and pyrimidine bases may, for example, be performed according to methods known in the art, such as those described by Ruth in EP 135 587. The modification of a ribonucleotide at the C-2' position of the ribose ring of the ribonucleotide may, for example, be performed according to the method described by Yamana, K. et al. in Bioconjugate Chemistry 1, 319–324 (1990).

An example of nucleotides modified with a chemical functionality group at each of the above-mentioned sterically tolerant sites is shown in FIGS. 10–14. Whether deoxyribonucleotides or modified deoxyribonucleotides are shown in FIGS. 10–14, it is understood that ribonucleotides are acceptable substitutes. A list of the designations of the modified nucleotides is provided below.

A1 represents adenine with a chemical functionality group Z replacing a hydrogen from the amino group located at the C-6 position.

A2 represents adenine with a chemical functionality group Z attached to the hydroxyl group located at the C-2' position of the ribose ring.

A3 represents adenine with chemical functionality group Z replacing the hydrogen located at the C-8 position.

A4 represents adenine with chemical functionality group Z replacing the hydroxyl located at the C-2' position of the ribose ring.

C1 represents cytidine with a chemical functionality group Z replacing a hydrogen from the amino acid group located at the C-6 position.

C2 represents cytidine with a chemical functionality group Z attached to the hydroxyl group located at the C-2' position of the ribose ring.

C3 represents cytidine with chemical functionality group Z replacing the hydroxyl group located at the C-2' position of the ribose ring.

G1 represent guanine with a chemical functionality group Z replacing the hydrogen located at the C-8 position.

G2 represents guanine with a chemical functionality group Z attached to the hydroxyl group located at the C-2' position of the ribose ring.

G3 represents guanine with chemical functionality group Z replacing the hydroxyl group located at the C-2' position of the ribose ring.

T1 represents thymidine with chemical functionality group Z replacing a hydrogen from the methyl group located at the C-5 position.

T2 represents thymidine with a chemical functionality group Z attached to the hydroxyl group located at the C-2' position of the ribose ring.

T3 represents thymidine with chemical functionality group Z replacing the hydroxyl group located at the C-2' position of the ribose ring.

U1 represents uridine with chemical functionality group Z replacing the hydroxyl group located at the C-2' position of the ribose ring.

U2 represents uridine with a chemical functionality group Z attached to the hydroxyl group located at the C-2' position of the ribose ring.

Z represents chemical functionality groups X1, X2, X3, X4, Y1, Y2, Y3 or Y4.

It is important to note that chemical functionality groups X and Y do not have to be attached at the same positions on their respective nucleotides. For example, without limitation, group X could be attached to uridine at position C-5 on an nucleotide in the junction of A/B sequence and group Y could be attached to position C-2' on an appropriate nucleotide in the end of targeting sequence C.

The preferred position for attaching one of the chemical functionality group, Y, for example, to a nucleotide is the C-2' position of the ribose ring of the nucleotide. For example, it is convenient to replace the hydroxyl group at the C-2' position of the ribose ring with an amino group by, for example, the protocol described in Moffatt, et al., J. Org. Chem. 36, 250 (1971), or by an aminomethyl group as described by Ioannidid et al. Nucleosides and Nucleotides, 11: 1205 (1992), while the second chemical functionality group, X, for example, is attached, for example, to the C-5 position of the pyrimidine base. For example, see Ruth in EP 135 587. The amino group can serve either as a chemical functionality group, or as a bridging group for the attachment of chemical functionality groups to the ribose ring.

A chemical functionality group can optionally contain a bridging group through which it is attached to the nucleotide. Examples of bridging groups include, but are not limited to, amino, amido, thio, carbonyl, carboxyl, alkyl groups, aryl, alkylaryl and arylalkyl groups, optionally at any position with groups such as but not limited to amido, carbonyl, carboxyl, amino and thio. Alkyl groups may be cyclic in whole or in part. Examples of alkyl groups include, but are not limited to, methyl, ethyl, propyl, pentyl, cyclopentyl, hexyl, cyclohexyl, etc. Examples of aryl groups include, but are not limited to, phenyl, naphthyl, imidazolyl, indyl, etc.

In a given pair of oligonucleotide probes one member of the pair has a nucleophilic chemical functionality group and the other member of the pair has an electrophilic chemical functionality group (i.e. if X is a nucleophile, then Y is an electrophile, and vice versa).

Some examples of nucleophiles include —SH, —NH$_2$, —NHA (where A is an alkyl group, such as methyl, ethyl, propyl, butyl, etc. or an aryl group, such as phenyl, naphthyl, imidazolyl, indyl, etc.). Electrophiles are capable of forming single or double bonds via electron transfer from a nucleophile. The reaction between the nucleophile and the electrophile may involve the addition of the nucleophile across a double bond attached to an electron withdrawing group or the substitution of a nucleophile for an electrophilic leaving group.

One example of the addition of a nucleophile across a double bond is a Michael addition such as the addition of a thiol group to a double bond of a maleimido moiety.

Other types of reaction between the chemical functionality groups are, for example, the Diels-Alder reaction or any pericyclic reaction that produces one or more new chemical bonds.

Figure 15:
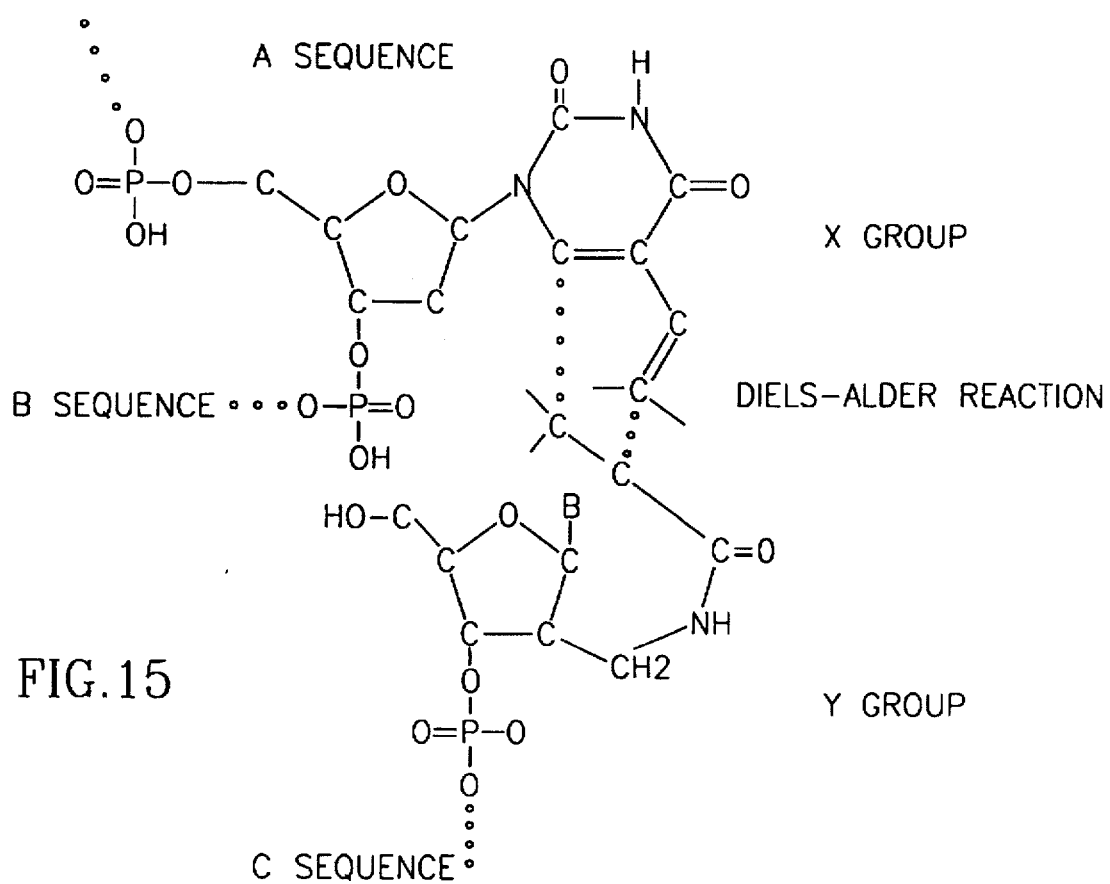
FIG. 15 shows the preferred embodiment for a Diels-Alder reaction is the system where uridine is modified at the C-5 position to form a Diene which functions as a chemical functionality group, X, for example in oligonucleotide probes 1, 1', 3 and 3'. Whereas in the end of targeting sequences C and C', the sugar is modified at the C-2' position by 2-butenedioic acid which functions as a chemical functionality group, Y, for example.

The preferred embodiment for a Diels-Alder reaction is the system where uridine is modified at the C-5 position to form a Diene which functions as a chemical functionality group, X, for example in oligonucleotide probes 1, 1', 3 and 3'. Whereas in the end of targeting sequences C and C', the sugar is modified at the C-2' position by 2-butenedioic acid which functions as a chemical functionality group, Y, for example, as is illustrated in FIG. 15.

Computer modeling of this particular example revealed that in order for Diels-Alder reaction to take place, the amino group at the C-2' position should be extended one more atom that has a tetrahedral configuration. Methylene group for example, could meet this requirement.

Chemical functionality groups can also be selected that form chemical bonds via a photochemical reaction such as [2+2] photo-cyclodimerization or other type of photocycling.

Protection of Chemical Functionality Groups From Being Reactive With Each Other in the Absence of the Target Nucleic Acid Sequence One of the most important features in DNA oligonucleotide probe amplification according to the method of invention, is to eliminate spurious amplification by-products. The present invention offers versatile ways of protecting chemical functionality groups (X and Y) from being reacted with each other in a template-independent manner. In a preferred embodiment, the chemical bond between X and Y groups is formed via the Diels-Alder reaction. This reaction is preferred since it is region controlled and stereospecific by nature. For example, the $\pi$ electrons of the Diene and the Ene groups should precisely overlap in order to interact in a pericyclic reaction.

Description of the Chemical Amplification Process of the Method of the Invention for the Detection of the Presence of a Nucleic Acid Sequence in a Sample In a first embodiment of the method of the present invention it is employed for the detection of the presence of a nucleic acid sequence in a sample.

Amplification of a target nucleic acid sequence is accomplished in the present invention by joining two or more chemically modified oligonucleotide probes for each strand of a target nucleic acid sequence, to form a joined oligonucleotide product. The "amplification" that is achieved through the methods of the present invention denotes an increase in the amount of desired nucleic acid molecules present in the reaction vessel. "Substantial amplification" refers to greater than about 100-fold amplification. Once formed, the joined oligonucleotide product serves as a template for further production of joined oligonucleotide products. The steps of the process are repeated a sufficient number of times to produce a detectable amount of joined oligonucleotide products. Each repetition of the steps of the process of the present invention is referred to as a cycle. The number of cycles required to produce a detectable amount of joined nucleotide products depends to a great extent on the number of target molecules initially present in the examined nucleic acid sample. The greater the number of target molecules in a sample, the fewer the number of cycles needed to produce a detectable amount of joined oligonucleotide products. When a desired amount of joined oligonucleotide products is formed, it is detected. A novel aspect of the present invention is the way in which the oligonucleotide probes are joined to form an oligonucleotide product. Neither DNA polymerase nor DNA ligase is used in the present invention to form the joined oligonucleotide products.

Oligonucleotide probes 1, 1', 2, and 2' are used in the process of the present invention to amplify target sequences in a single or double-stranded nucleic acid molecule as follows.

As described above, when a target nucleic acid sequence is present in a test sample, under carefully controlled hybridization conditions, only targeting sequence A and targeting sequence C of oligonucleotide probes 1 and 2 respectively, hybridize to adjacent regions of the target sequence. This leaves protecting sequence B of oligonucleotide probe 1 unhybridized to the target sequence. When targeting sequence A and targeting sequence C have formed stable hybrid complexes with the target sequence, chemical functionality groups X1 and Y1 are brought into sufficiently close proximity to form a chemical bond. The bond between chemical functionality groups X1 and Y1 joins oligonucleotide probe 1 to oligonucleotide probe 2, forming a first joined oligonucleotide product. Once formed, the two sequences of the first joined oligonucleotide product constitute a "target complementary sequence", and are complementary to adjacent sequences of the target sequence.

Similarly, when targeting sequence A' and targeting sequence C' of oligonucleotide probes 1' and 2', respectively, hybridize to adjacent regions of the target complementary sequence, protecting sequence B' of oligonucleotide probe 1' is left unhybridized. This, in turn, brings chemical functionality group X2 of targeting sequence A' and chemical functionality group Y2 of targeting sequence C' into sufficient proximity to form a chemical bond that joins oligonucleotide probes 1' and 2' together to produce a second joined oligonucleotide product. Once formed, the two sequences of the second joined oligonucleotide product constitute a "target sequence" and are complementary to adjacent sequences of the target complementary sequence.

The chemical functionality groups X1 and X2 on oligonucleotide probes 1 and 1' are sheltered, and therefore protected from interacting with chemical functionality groups Y1 and Y2, by nucleotides of the protecting sequences B and B', on one side, and by nucleotides of the targeting sequences A and A' on the other side, respectively.

Furthermore, the chemical functionality groups X2 and X2 on oligonucleotide probes 1 and 1' may be sheltered, and therefore protected from interacting with chemical functionality groups Y1 and Y2, by providing protecting sequences B and B' with sequences which are complementary in a palindrome manner to targeting sequences A and A', therefore creating a stem and loop structure, which stem is positioned so that the chemical functionality groups are base paired and therefore protected. Similarly, providing protecting sequences D and D' with sequences which are complementary in a palindrome manner to targeting sequences A and A' would protect chemical functionality groups X3 and X4 on oligonucleotide probes 3 and 3' from interacting with chemical functionality groups Y3 and Y4 on oligonucleotide probes 4 and 4' when they are free in solution.

The chemical functionality groups X1 and X2 on oligonucleotide probes 1 and 1' and the chemical functionality groups Y1 and Y2 on oligonucleotide probes 2 and 2' may be further sheltered and protected by oligonucleotides 1.1, 2.1, 1.1' and 2.1' which are complementary to oligonucleotide probes 1, 2, 1' and 2', respectively, in the region where the chemical functionality groups are located (equivalent oligonucleotides 3.1, 4.1, 3.1' and 4.1' may be used to protect chemical functionality groups X3, Y3, X4 and Y4, respectively).

As a result of the protection of the chemical functionality groups X1 and X2 of oligonucleotide probes 1 and 1', respectively, each chemical functionality group is prevented from reacting with a corresponding chemical functionality groups of other oligonucleotide probes. Chemical functionality groups are brought into sufficiently close proximity by hybridization of targeting sequence A and targeting sequence C of oligonucleotide probes 1 and 2, respectively, to the target nucleic acid sequence, or of targeting sequence A' and targeting sequence C' of oligonucleotide probes 1' and 2' to the target nucleic acid complementary sequence.

Figure 16:
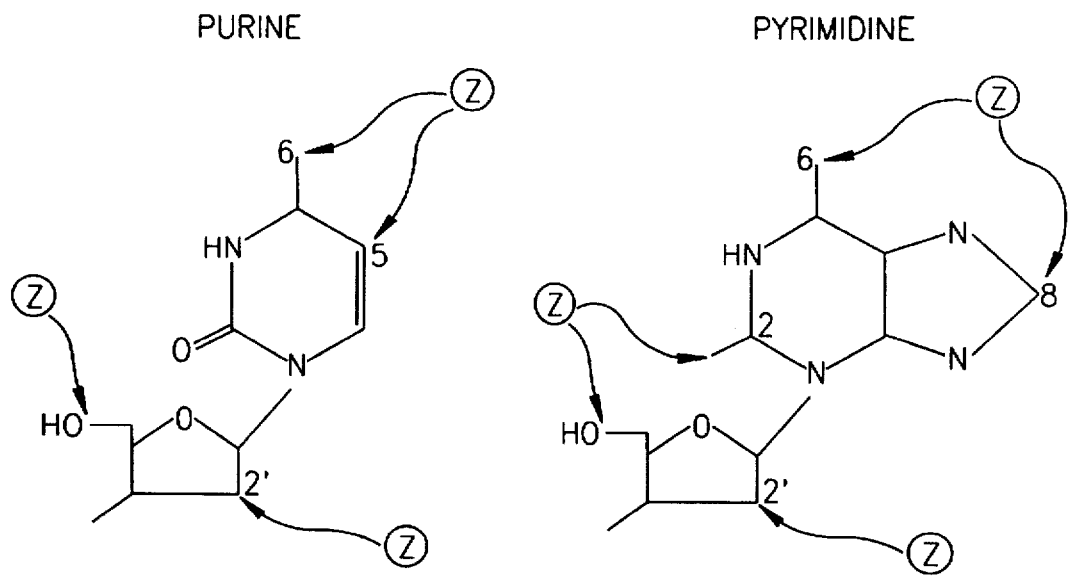
FIG. 16 shows a generalized illustrations of hybridized targeting sequence A and targeting sequence C, or of targeting sequence A' and targeting sequence C' to the target nucleic acid sequence or the target nucleic acid complementary sequence, with chemical functionality groups attached to the nucleotide bases.

A generalized illustrations of hybridized targeting sequence A and targeting sequence C, or of targeting sequence A' and targeting sequence C' to the target nucleic acid sequence or the target nucleic acid complementary sequence, with chemical functionality groups attached to the nucleotide bases, is illustrated in FIG. 16. As can be seen in the Figure, chemical functionality groups X and Y can be attached either to the C-2' position of the ribose ring or to the nucleotide base.

Figure 17:
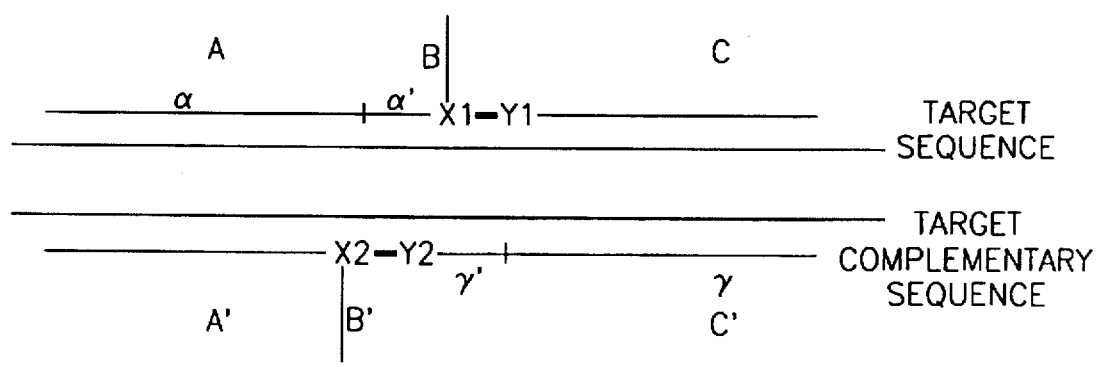
FIG. 17 shows a generalized illustration of oligonucleotide probes hybridized to a double-stranded target molecule and joined by chemical functionality groups to form a first and a second joined oligonucleotide products.

A generalized illustration of both pairs of oligonucleotide probes hybridized to a double-stranded target molecule and joined by chemical functionality groups to form a first and a second joined oligonucleotide product is shown in bolded lines in FIG. 17. It is understood that in the preferred embodiments of the present invention, there is no gap between the oligonucleotide probes, although in some applications, a gap of one or two nucleotides is permissible.

In a sample containing a single-stranded target molecule, the second joined oligonucleotide product is formed after the first cycle. In order to form a second joined oligonucleotide product in the absence of a target complementary molecule, a first joined oligonucleotide product must be formed in the first cycle of the process. The first joined oligonucleotide product has the target complementary sequence and functions as a template to which oligonucleotide probes 1' and 2' hybridize. Oligonucleotide probes 1' and 2' form a second joined oligonucleotide product, having the target sequence, on the second cycle and subsequent cycles of the process.

Once the first joined oligonucleotide product is formed in the first cycle of the process, the product is separated from the target sequence by denaturation. The terms "denature" or "denaturation" as used herein refer to a reversible loss of a higher order structure and to separation of hybridized nucleic acids into single-strands, produced by physiological or non-physiological conditions, such as, for example, enzymes, pH, temperature, salt or organic solvents.

The second joined oligonucleotide product, once it is formed, is also separated from the target complementary sequence or first joined oligonucleotide product by denaturation. The target molecule and the first and second joined oligonucleotide products serve as templates for repeated cycles of the process.

Figure 18:
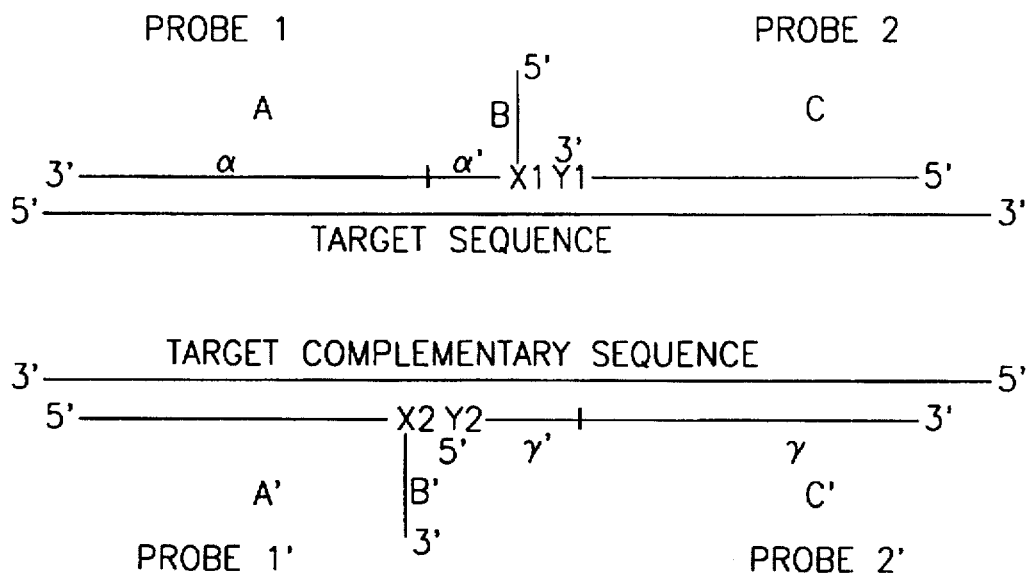
FIG. 18 is a schematic depiction of the first cycle in the amplification procedure of a double-stranded sequence which includes hybridization of the oligonucleotide probes to the target sequence and the target complementary sequence and joining of the oligonucleotide probes via the chemical functionality groups to form joined oligonucleotide products.
Figure 19:
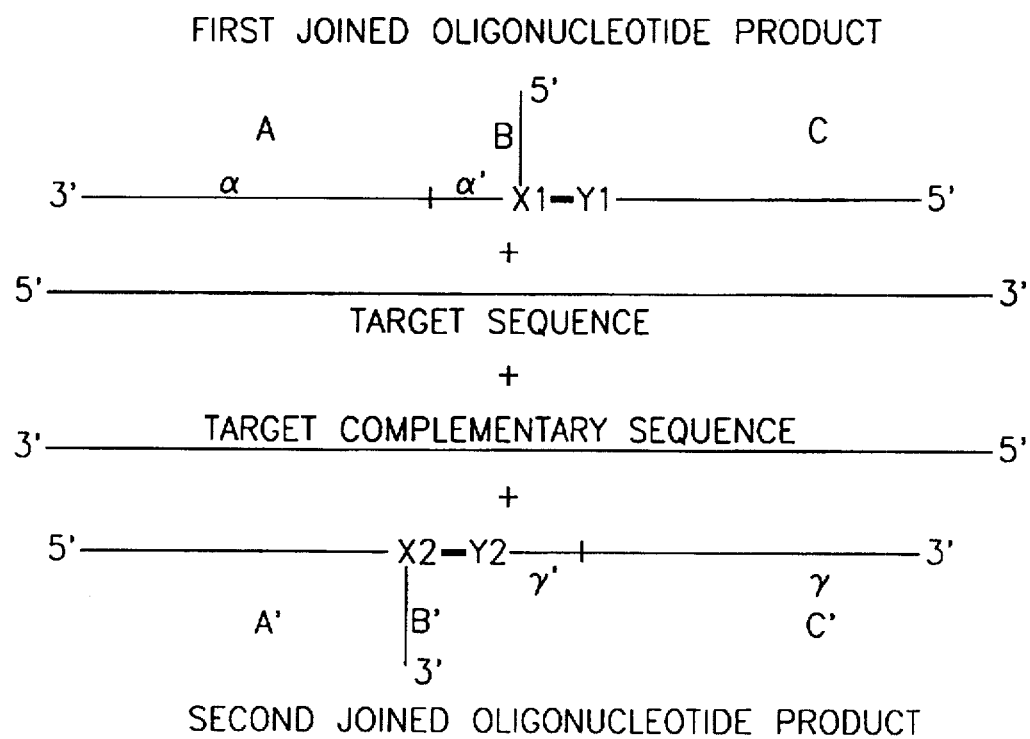
FIG. 19 is a schematic depiction of the formation of joined oligonucleotide probes via the chemical functionality groups which is followed by denaturation of the first and second joined oligonucleotide products from the target sequence and the target complementary sequences, respectively.
Figure 20:
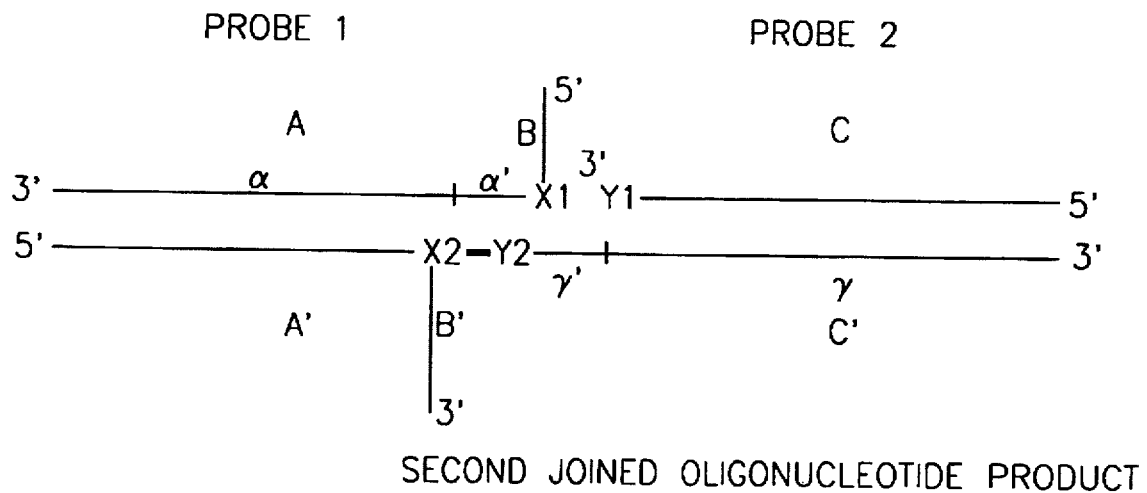
FIG. 20 shows a generalized illustration of the ability of the first and second joined oligonucleotide products to act as a template for the formation of additional second and first joined oligonucleotide products, respectively, during the second and all subsequent cycles of the amplification process.
Figure 20:
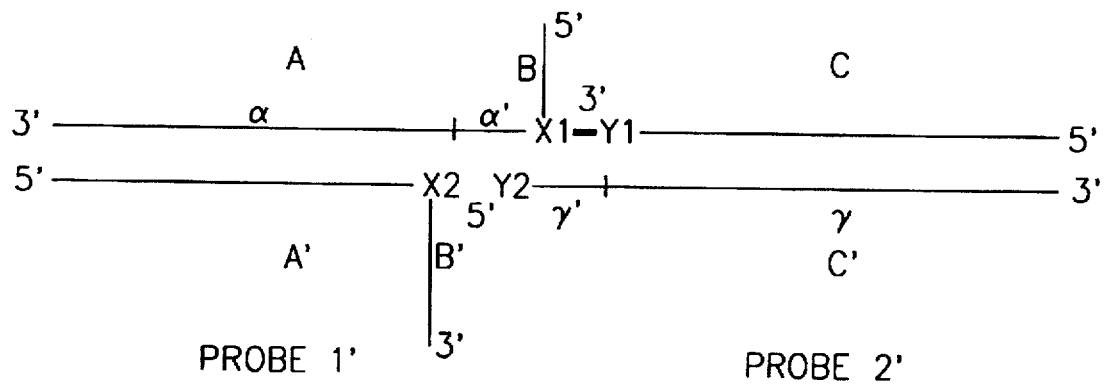

A generalized illustration of the first cycle of the amplification process of the present invention for a double-stranded sequence is shown in FIGS. 18–20.

As illustrated in FIG. 18, the first cycle in the amplification procedure of a double-stranded sequence includes hybridization of the oligonucleotide probes to the target sequence and the target complementary sequence and joining of the oligonucleotide probes via the chemical functionality groups to form joined oligonucleotide products.

As illustrated in FIG. 19, the formation of joined oligonucleotide probes via the chemical functionality groups is followed by denaturation of the first and second joined oligonucleotide products from the target sequence and the target complementary sequences, respectively.

Once the first cycle of the process is completed, further amplification of the target sequence is achieved by repeated cycles of denaturation of the joined oligonucleotide products, annealing of the oligonucleotide probe pairs to the joined oligonucleotide products and formation of chemical bonds between the chemical functionality groups to produce more joined oligonucleotide products. Therefore, All cycles following the first cycle necessarily have both target sequence and target complementary sequence.

A generalized illustration of the ability of the first and second joined oligonucleotide products to act as a template for the formation of additional second and first joined oligonucleotide products, respectively, during the second and all subsequent cycles of the amplification process for a single or double-stranded target sequence is shown in FIG. 20.

Hybridization of oligonucleotide probes to the target sequence and the target complementary sequence of the first and second joined oligonucleotide products formed as described in the previous step, and joining the oligonucleotide probes to form more joined oligonucleotide products.

In another embodiment of the present invention, linear amplification of a target sequence or, alternatively, a target complementary sequence, if present, can be accomplished by using only probes 1 and 2 or probes 1' and 2' in the above-described process, respectively.

In a preferred embodiment of the present invention, a standard hybridization buffer, such as, for example, 30% deionized formamide in water (vol/vol), 0.54M NaCl, 30 mM sodium phosphate (pH 7.4), 0.3 mM EDTA, 5% dextran sulfate 500K m.w. (Sigma) (w/vol) and 0.1% Triton X-100 (vol/vol), is used with oligonucleotide probes of any length from six to one hundred nucleotides. Only the temperature of denaturation and the temperature of hybridization change as the length (more accurately, the melting temperature, Tm) of the oligonucleotide probes changes. The hybridization temperature and the denaturation temperature are both functions of the length (or Tm) of the oligonucleotide probes.

Generally, the oligonucleotide probe pairs will be present in molar excess of about $10^5$–$10^{15}$, preferably $10^9$–$10^{15}$, pairs per nucleic acid target sequence or target complementary sequence. The exact amount of the pairs to be used in diagnostic purposed may not be known due to uncertainty as to the amount of the nucleic acid target in a sample. However, using an average amount of $10^{15}$ oligonucleotide probe pairs is applicable in a typical diagnosis assay format. A large molar excess is preferred in any case to improve the efficiency of the invented process.

Since the chemical functionality groups are prohibited from reacting and joining the oligonucleotide probes together if the target hybridizing sequences of both oligonucleotide probes have not hybridized to the target sequence, formation of target-independent joined oligonucleotide product is avoided.

Description of the Chemical Amplification Process of the Method of the Invention for the Detection of Sequence Alterations In a second embodiment of the method of the present invention it is employed for the detection of nucleotide alterations in a target nucleic acid sequence. As will shortly be described, the method of the present invention, when employed for the detection of a nucleotide alteration in a target nucleic acid sequence is sensitive enough to detect a single base alteration, such as, for example, a point mutation, e.g. a single base pair alteration.

The ability of the method of the present invention to detect sequence alterations will herein be described for the detection of a single base alteration such as a point mutation in a target nucleic acid sequence.

Figure 21:
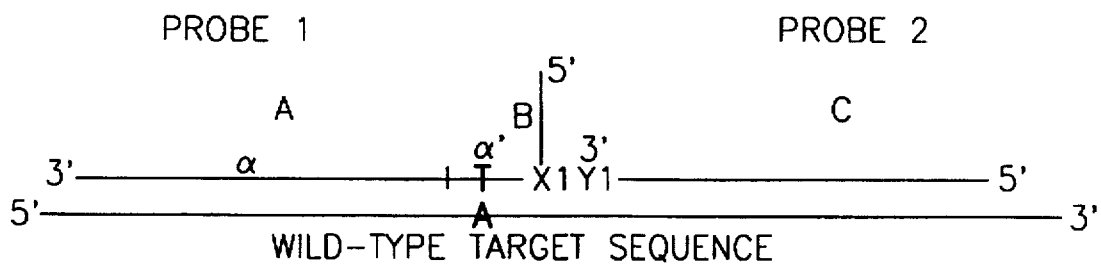
FIG. 21 shows a the similarities and differences among the oligonucleotide probes constituting the first and second oligonucleotide probe sets aimed at the discriminative amplification of nucleic acid sequences which differ by an A→G point mutation.
Figure 21:
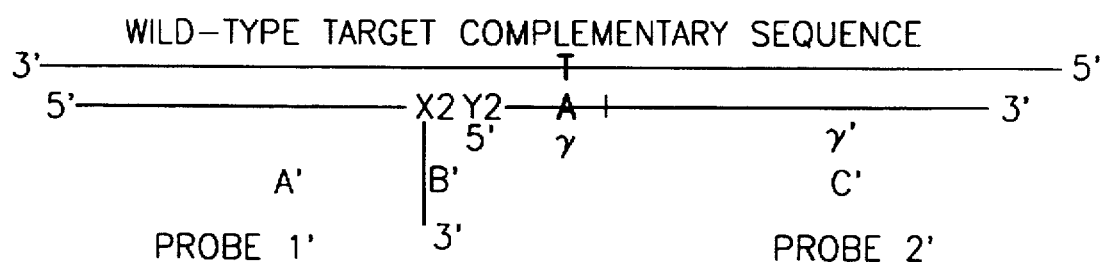
Figure 21:
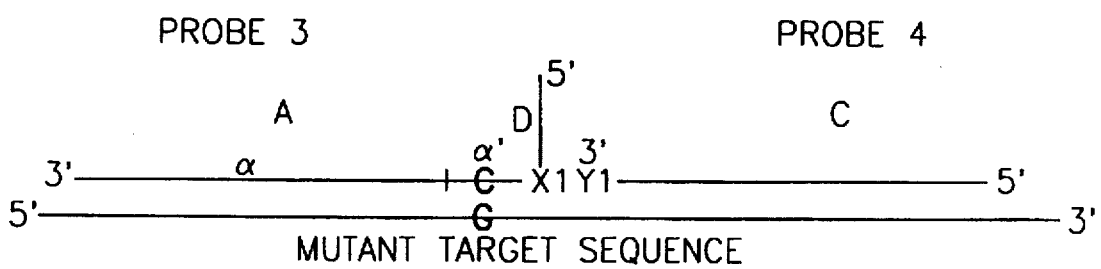
Figure 21:
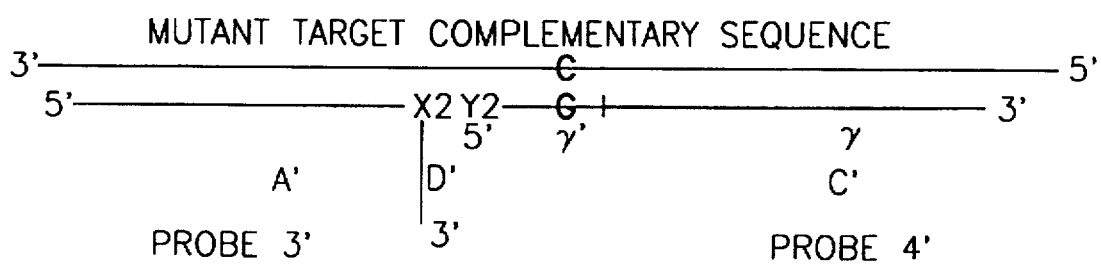

To this end, two sets of four oligonucleotide probes are designed. The first set is designed to amplify a wild-type sequence and includes four oligonucleotide probes designated 1, 1', 2 and 2'. These oligonucleotide probes are similar in their built-up, that is the arrangement of protecting and targeting sequences, to the ones described above, used for the detection of the presence of a target nucleic acid in a test sample. The second set of oligonucleotide probes consists of oligonucleotide probes designated 3, 3', 4 and 4'. The built-up of oligonucleotide probes 3, 3', 4 and 4' of the second oligonucleotide probes set is similar to the built-up of oligonucleotide probes 1, 1', 2 and 2' of the first oligonucleotide probes set, respectively. The sequence of oligonucleotide probes 3' and 4 of the second oligonucleotide probes set is similar to the sequence of oligonucleotide probes 1' and 2 of the first oligonucleotide probes set, respectively, whereas oligonucleotide probes 3 and 4' of the second oligonucleotide probes set differ in their sequence from oligonucleotide probes 1' and 2 of the first oligonucleotide probes set, in a position that is complementary to the sequence alteration to be determined, in the target nucleic acid sequence or the target nucleic acid complementary sequence, respectively. In these positions oligonucleotide probes 3 and 4' are fully complementary to the mutant target sequence and to the mutant target complementary sequence, respectively. Furthermore, at equivalent location on oligonucleotide probes 3, 3', 4 and 4' positioned are chemical functionality groups X3, X4, Y3 and Y4 wherein X3 and Y3 chemical functionality groups can form a chemical bond when oligonucleotide probes 3 and 4 are hybridized to the mutant target nucleic acid sequence, and X4 and Y4 chemical functionality groups can form a chemical bond when oligonucleotide probes 3' and 4' are hybridized to the mutant target nucleic acid complementary sequence. These similarities and differences among the oligonucleotide probes constituting the first and second oligonucleotide probe sets are schematically depicted in FIG. 21 along with a wild-type and a mutant (A→G point mutation as read from the target nucleic acid sequence) target nucleic acid sequence and complementary sequence.

For the execution of a minute sequence alteration detection procedure according to the second embodiment of the method of the present invention in its simplest form, two reaction vessels are used. In a first reaction vessel contained are a nucleic acid sample, a suitable buffer to carry out an amplification process as described above and oligonucleotide probes of the first oligonucleotide probes set, these are oligonucleotide probes 1, 1', 2 and 2'. In a second reaction vessel contained are the nucleic acid sample, the suitable buffer and oligonucleotide probes of the second oligonucleotide probes set, these are oligonucleotide probes 3, 3', 4 and 4'. Suitable number of amplification cycles are carried out as outlined above, and, following amplification, a detection procedure is exercised to determine the presence or absence of amplification products in each of the vessels.

If the target nucleic acid sequence contained in the examined nucleic acid sample is homozygous for the wild-type nucleotide (A in the above given example) amplification products will accumulate only in the first reaction vessel containing oligonucleotide probes 1, 2, 1' and 2' which are complementary to the wild-type target nucleic acid sequence and to the wild-type target nucleic acid complementary sequence, at the examined nucleotide site, respectively.

whereas amplification products will not accumulate in the second reaction vessel containing oligonucleotide probes 3, 4, 3' and 4' which are not complementary to the wild-type target nucleic acid sequence and to the wild-type target nucleic acid complementary sequence, at the examined nucleotide site, respectively. If, on the other hand, the target nucleic acid sequence contained in the examined nucleic acid sample is homozygous for the mutant nucleotide (G in the above given example) amplification products will accumulate only in the second reaction vessel containing oligonucleotide probes 3, 4, 3' and 4' which are complementary to the mutant target nucleic acid sequence and to the mutant target nucleic acid complementary sequence, at the examined nucleotide site, respectively, whereas amplification products will not accumulate in the first reaction vessel containing oligonucleotide probes 1, 2, 1' and 2' which are not complementary to the mutant target nucleic acid sequence and to the mutant target nucleic acid complementary sequence, at the examined nucleotide site, respectively. If the target nucleic acid sequence contained in the examined nucleic acid sample is heterozygous, that is the examined nucleic acid sample contains both the wild-type and the mutant nucleic acid sequences and their corresponding nucleic acid complementary sequence amplification products will accumulate in both reaction vessels. Therefore, if the examined nucleic acid sequence is obtained from a specific individual, the genotype of the individual (i.e. whether the individual is homozygous for the wild-type or mutant sequence or whether the individual is heterozygous) at the mutation site may thus be determined In a more sophisticated form for the execution of a minute sequence alteration detection procedure according to the second embodiment of the method of the present invention, one reaction vessel may be used provided that the amplification products derived from a wild-type sequence are distinguishable from the amplification products derived from the mutant sequence.

When the minute sequence alteration detection procedure according to the second embodiment of the method of the present invention described above is exercised, X1, X2, X3 and X4 chemical functionality groups may all or some be identical to each other, although it is preferred that X1 and X2 chemical functionality groups are different than X3 and X4 chemical functionality groups when the reaction is performed in a single reaction vessel according to the more sophisticated form outlined above. In all cases Y1, Y2, Y3 and Y4 chemical functionality groups are selected to enable the formation of a chemical bond with the X1, X2, X3 and X4 corresponding chemical functionality groups.

In order for second embodiment of the method of the present invention to be useful at the detection of a minute sequence alteration such as a point mutation, as described above, few limitations in the built-up of the oligonucleotide probes and in the type of the chemical functionality groups should be exercised to enable a discriminative amplification described. The α' parts of oligonucleotide probes 1 and 3 and the γ' parts of oligonucleotide probes 2' and 4' should be as short as required to impose a distortion in the tertiary structure of the hybridized sequences at the position of the chemical functionality groups even in the case of a single nucleotide mismatch. On the other hand, α' parts of oligonucleotide probes 1 and 3 and the γ' parts of oligonucleotide probes 2' and 4' should be long enough to avoid failure of amplification due to distortion in the tertiary structure imposed by the chemical functionality groups themselves after the formation of a chemical bond between them. The chemical functionality groups should be selected to meet these specifications. The ultimate chemical functionality groups would, therefore, be ones that distore the tertiary structure of the hybridized sequences to a permissible degree that enables the use of oligonucleotide probe complementary pairs that are of the same length. As schematically presented in FIG. 22, in this case, the modified nucleotides themselves (designated in the Figure T1, T2, A1, A2, C1, C2, G1 and G2, and T3, T4, A3, A4, C3, C4, G3 and G4), to which the chemical functionality groups are conjugated, act as the amplification discriminative sequences.

In another embodiment of the present invention, linear amplification of a target sequence or, alternatively, a target complementary sequence, if present, can be accomplished by using only probes 1, 2, 3 and 4 or probes 1', 2', 3' and 4' in the above-described process.

Detection of Amplification Products

Once a sufficient quantity of joined oligonucleotide products is produced, it may be detected by routine methods of the art, such as, for example by immobilizing one oligonucleotide probe member of a joined oligonucleotide product (i.e. oligonucleotide probe 1 or 1') and labeling the other member (i.e. oligonucleotide probe 2 or 2') with, for example, one or more radioactive, chromogenic, chemilluminescent, or fluorescent moieties, or by sizing the joined oligonucleotide products on a gel.

Methods for labeling oligonucleotide probes have been described, for example, by Leary et al., Proc. Natl. Acad. Sci. USA (1983) 80: 4045; Renz and Kurz, Nucl. Acids res., (1984) 12: 3435; Richardson and Gumport, Nucl. Acids Res. (1983) 11: 6167; Smith et al., Nucl. Acids Res. (1985) 13: 2399; and Meinkoth and Wahl, Anal. Biochem. (1984) 138: 267.

The label may be radioactive. Some examples of useful radioactive labels include $^{32}P$, $^{33}P$, $^{125}I$, $^{131}I$ and $^3H$. Use of radioactive labels have been described in U.K. 2,034,323, U.S. Pat. Nos. 4,358,535 and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates (in brackets) include, for example, horseradish peroxidase (pyrogallol and o-phenylenediamine), beta-galactosidase (fluorescein beta-D-galactopyranoside) and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981–1991 (1961).

Useful chromophores include, for example, fluorescent, chemilluminescent, and bioluminmolecules, as well as dyes. Some specific chromophores useful in the present invention include for example, fluorescein, rhodamine, Texas red, phycoerythrin, umbelliferone and luminol.

Detection of the joined oligonucleotide product is performed by methods known in the art, such as with a radioactive label or with a non-radioactive capture assay. For example, joined oligonucleotide products with a radioactive label are detected by autoradiography following sizing of the joined oligonucleotide products on a gel. Alternatively, joined oligonucleotide products are detected in a non-radioactive capture assay by attaching a receptor, such as, for example, biotin to oligonucleotide probe 1 and attaching an enzymatic label, such as, for example, heat stable alkaline phosphatase, to oligonucleotide probe 2. A microtiter plate coated with a ligand for the receptor, such as, for example, avidin is used to capture oligonucleotide probe 1 via the biotin attached to the probe. The enzymatic label attached to oligonucleotide probe 2 is exposed to a chromogenic substrate, such as 5-bromo-4-chloro-3-indolyl phosphate/ nitro blue tetrazolium, for example, and a colorimetric change in the substrate is detected by, for example, measuring the optical density (O.D.) of the solution.

The labels may be conjugated to the oligonucleotide probe by methods that are well known in the art. The labels may be directly attached through a functional group on the oligonucleotide probe. Some examples of suitable functional groups include, for example, amino, carboxyl, sulfhydryl, melamide, isocyanate and isothiocyanate.

Alternatively, labels such as enzymes and chromophoric molecules may be conjugated to the oligonucleotide probe by means of coupling agents, such as dialdehydes, carbodiimides, and the like.

The label may also be conjugated to the oligonucleotide probe by means of a ligand attached to the oligonucleotide probe by a method described above, and a receptor for that ligand attached to the label. Any of the known ligand-receptor combinations is suitable. Some suitable ligand-receptor pairs include, for example, biotin-avidin or biotin-streptavidin, and antigen-antibody. The biotin-avidin combination is preferred.

If a label is used to detect the joined oligonucleotide product, label can be attached to either part or sequence of one or more of the oligonucleotide probes.

In Situ Detection of Amplification Products

Following a sufficient number of cycles a detectable quantity of amplification products is generated and may be detected in accordance with the detection procedures of the present invention, described above. Nevertheless, it is highly advantageous to have an effective in situ detection procedure (s) that enables the detection of thus formed amplification products merely by the addition of a detection reagent to the reaction vessel preferably before the amplification process is initiated or, alternatively, after the amplification process is completed.

A straight forward approach to achieve the above in situ detection of amplification products is to design the chemical functionality groups X1 and Y1, X2 and Y2, X3 and Y3 and/or X4 and Y4 such as they form a detectable compound when a chemical bond is formed between them.

The detectable compound may for example be detected colorimetically in O.D. units or fluorimetrically depending on the chemical nature of the compound. The compound may also be detected via directly or indirectly labeled antibodies, for example a monoclonal antibody, raised against the compound.

In situ detection of amplification products may also be accomplished as delineated herein:

During the execution of the amplification procedures described above, single-stranded sequences B and B', and/or D and D', are obtained. These single-stranded sequences are unique to amplification products, therefore, one or all, may be employed to detect the presence of amplification products in accordance with two detection procedures to be described herein:

For simplicity purposes the description below refers mainly to protecting sequences B and B' of oligonucleotide probes of the first oligonucleotide probes set. It should be understood that the same description is valid also for protecting sequences D and D' of oligonucleotide probes of the second oligonucleotide probes set.

Figure 23:
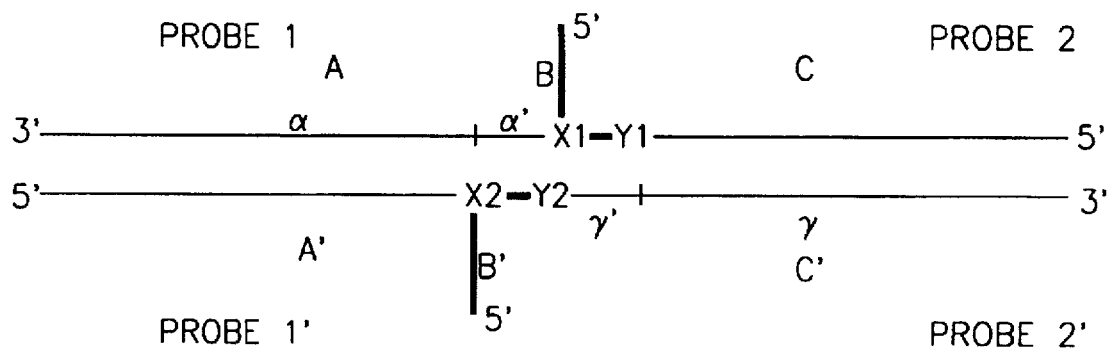
FIG. 23 is a schematic depiction of the single-stranded B and B' protecting sequences formed during the amplification procedure of the method of invention.
Figure 23:
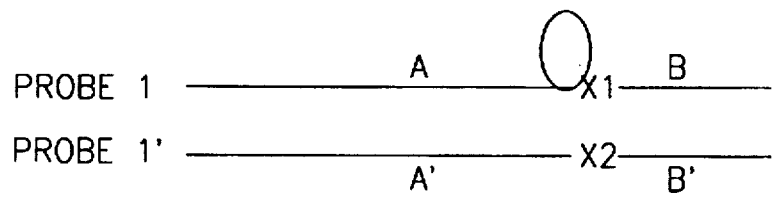
Figure 23:
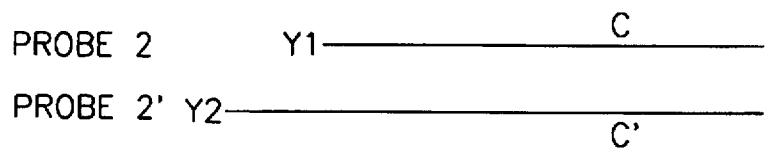

If the nucleotide sequence of protecting sequences B and B' are selected to render them complementary to each other, than after the amplification process is completed, all B and B' protecting sequences that are not incorporated into an amplification product eventually hybridize to one another along with the targeting sequences A and A' of oligonucleotide probes 1 and 1', whereas B and B' protecting sequences that are incorporated into amplification product remain single-stranded, as depicted in thick lines in FIG. 23.

In a case where protecting sequences B and B' are selected to be universal in sequence, they may be employed to detect any desired target nucleic acid sequence as will be described herein for the third and fourth embodiments of the method of the present invention.

Figure 24:
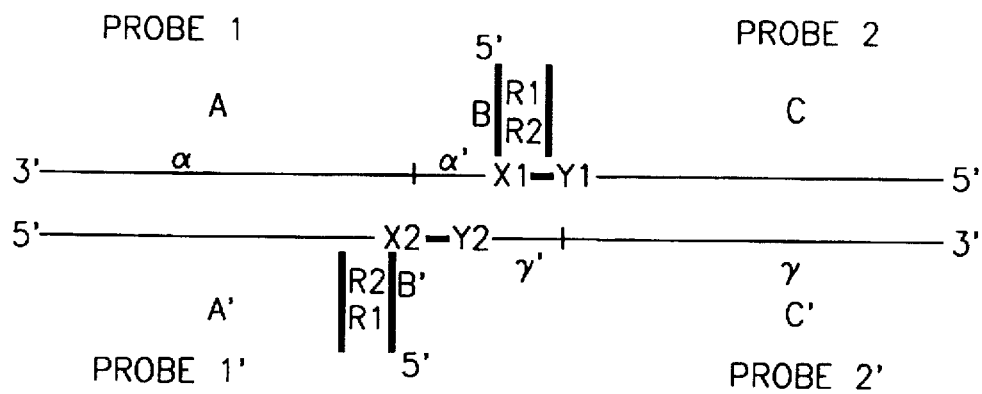
FIG. 24 is a schematic depiction of the labeled detection oligonucleotide probes employed in an in situ detection process which involves proximity energy transfer labeling.
Figure 25:
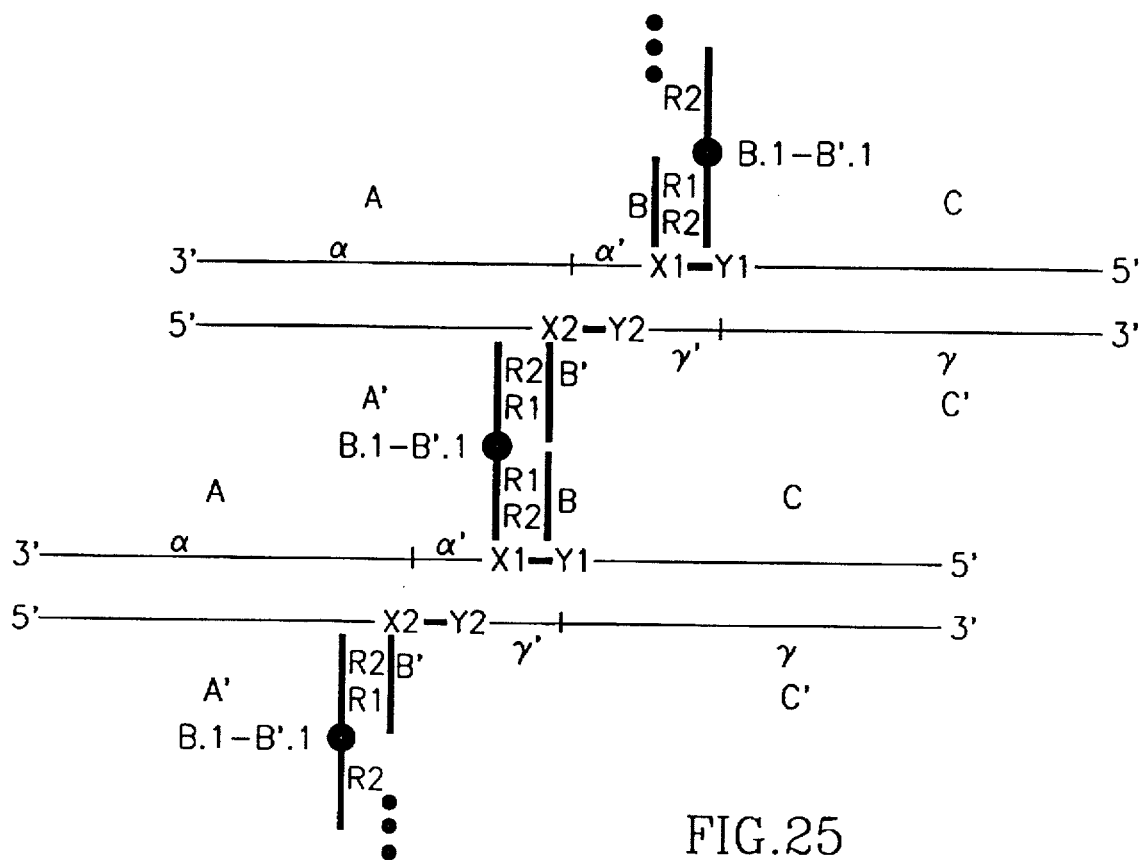
FIG. 25 is a schematic depiction of the labeled detection oligonucleotide probes employed in an in situ detection process which involves proximity energy transfer labeling in which hybridization leads to the formation of aggregates composed of a variable number of joined oligonucleotide products linked to one another via the B.1–B'.1 molecule.

In a third embodiment of the method of the present invention, employed are two labeled detection oligonucleotide probes in an in situ detection process which involves proximity energy transfer labeling. As a first detection oligonucleotide probe serve protecting sequences B and/or B' of oligonucleotide probes 1 and 1', respectively. The first detection oligonucleotide probe is conjugated to a proximity label moiety R1. A second detection oligonucleotide probe B.1 and/or B'.1 is being conjugated to a corresponding second proximity label moiety R2. As shown in FIG. 24, the second detection oligonucleotide probes B.1 and B'.1 are complementary to protecting sequences B and B', respectively. In a preferred embodiment of the invention, the second detection oligonucleotide probes B.1 and B'.1 are connected directly or indirectly to form a continuos molecule B.1–B'.1, as shown in FIG. 25.

The two labeled detection oligonucleotide probes hybridize to one another and therefore bring the proximity label moieties R1 and R2 to a proximity which is sufficient for their interaction to produce a detectable signal. In the case where detection oligonucleotide probes B.1 and B'.1 are each an individual molecule, hybridization of the kind shown in FIG. 24 is formed, whereas, if the detection oligonucleotide probes B.1 and B'.1 are connected to form a continuous molecule B.1-B'.1 ( delineated as —●— in FIG. 25), hybridization leads to the formation of aggregates composed of a variable number of amplification products linked to one another via the B.1-B'.1 molecule, as shown in FIG. 25, where ●●● delineate a linkage position of additional amplification products.

When the two labeled detection oligonucleotide probes, for example B and B.1, are hybridized, proximity labeling moieties R1 and R2 are brought into proximity that enables an energy transfer reaction between them to occur, resulting in a measurable energy emission.

For example, the first proximity label $R_1$ may be an energy donor and the second proximity label $R_2$ may be an energy acceptor. For example an energy donor, such as a fluorescent or chemilluminescent compound, may be used as one proximity label, with an energy acceptor, such as rhodamine being utilized as the second proximity label.

The detection procedure described above is relatively simple to use in combination with the amplification procedure since all it requires is additional oligonucleotide probes (B.1 and/or B'.1 or B.1-B'.1) and one additional cycle of hybridization.

The second detection oligonucleotide probe, to which R2 proximity labeling moiety is attached may be added to the reaction vessel along with all other reagents, before the amplification process is started, or alternatively it may be added to the reaction vessel after the amplification process is completed.

If, in turn, the target nucleic acid is not included in the examined sample, no amplification occurs, all B and B' sequences are hybridized to one another along with the targeting sequences A and A' of oligonucleotide probes 1 and 1', respectively and therefore the second proximity labeling detection oligonucleotide probe do not hybridize to them and a signal is not formed.

If the second embodiment of the method of the present invention, which embodiment aimed at the detection of minute sequence alterations is exercised, use of different proximity labeling moieties (i.e. ones that produce a different signal when are brought to an appropriate proximity) on each of the oligonucleotide probes sets, will enable to perform the sequence discriminative amplification of the wild-type or the mutant nucleic acid sequences in a single reaction vessel, simultaneously.

Yet, in a fourth embodiment of the method of the present invention the in situ detection of the amplification products is based upon the release of a label moiety L conjugated to single-stranded B and/or B' sequences which are incorporated into amplification products, and the removal of all double-stranded B and B' sequences along with label moieties conjugated to them from the test vessel via an affinity separation moiety S conjugated to oligonucleotide probes 1 and/or 1'.

As explained above, after the amplification process is completed, protecting sequences B and B' which are incorporated into amplification products are the sole B and B' single-stranded sequences in the reaction vessel, since protecting sequences B and B' of oligonucleotide probes 1 and 1' that were not incorporated into an amplification product are hybridized to one another as shown above. These single-stranded B and B' sequences may be nucleated, for example, via the use of a single-stranded specific nuclease, or an appropriate chemical process, resulting in the release of the label moiety L conjugated to them to the surrounding solution.

To one or more locations of one or more of the oligonucleotide probes used in the amplification reaction of the method of invention, these are, for example, various locations along the targeting sequences A and A' of oligonucleotide probes 1 and 1', respectively, conjugated is one or more affinity separation moiety S. The affinity separation moiety S is characterized by its ability to bind a counterpart moiety S' in high affinity. The affinity separation moiety S may for example be a hapten or a biotin and the counterpart moiety may, therefore, be a suitable antibody or, avidin or streptavidin, respectively. The counterpart affinity separation moiety S' is preferably attached to a solid support such as for example plastic, dextran, glass or magnetic beads or preferably to the top of the reaction vessel, for example to a screw cap.

Figure 26:
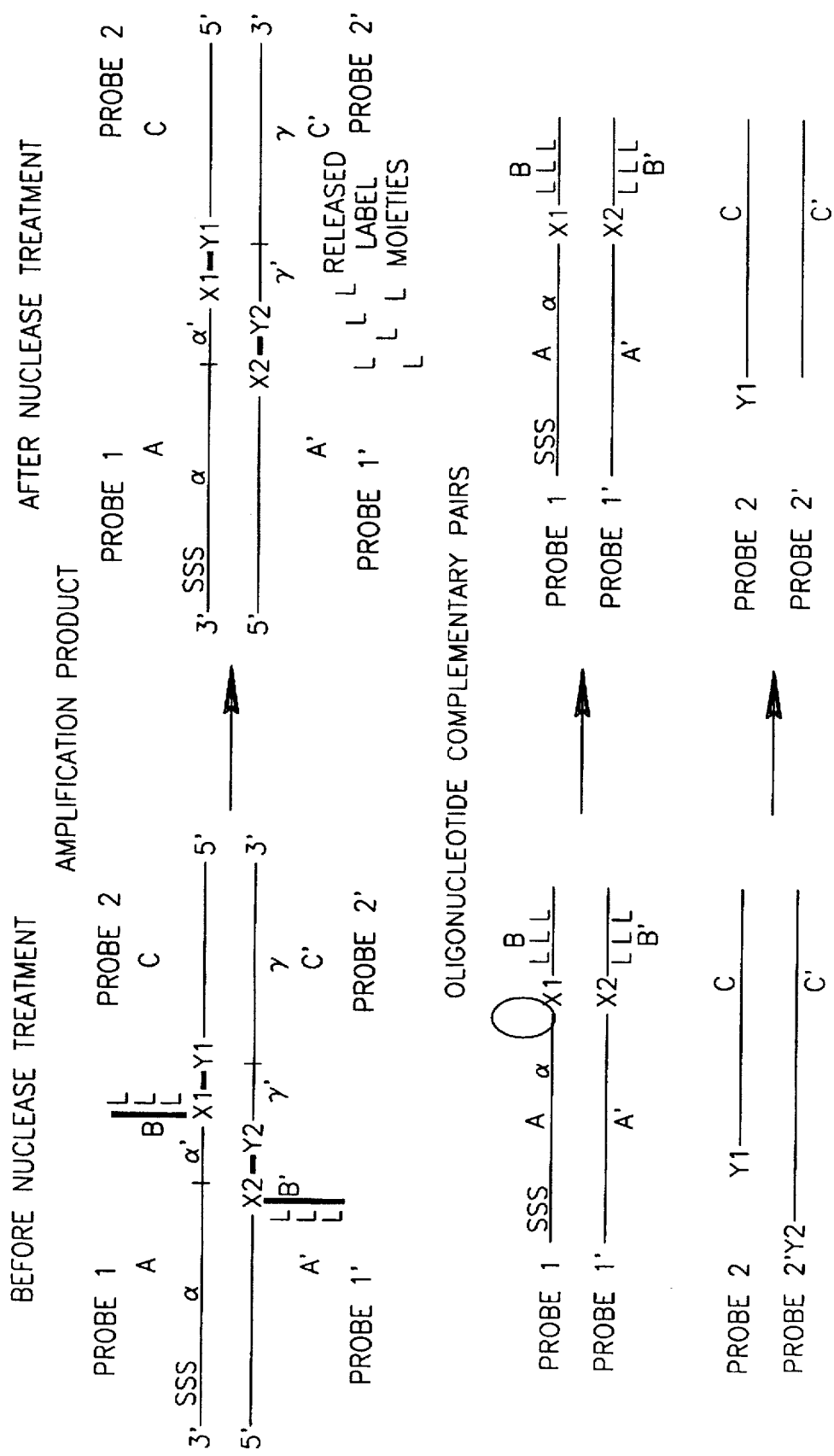
FIG. 26 is a schematic depiction of an in situ detection method which involves the release and the detection of a label moiety L from single-stranded B and B' protecting sequences via the activity of a single-stranded specific nuclease and the removal of label moieties L not thus released via affinity separation.
Figure 27:
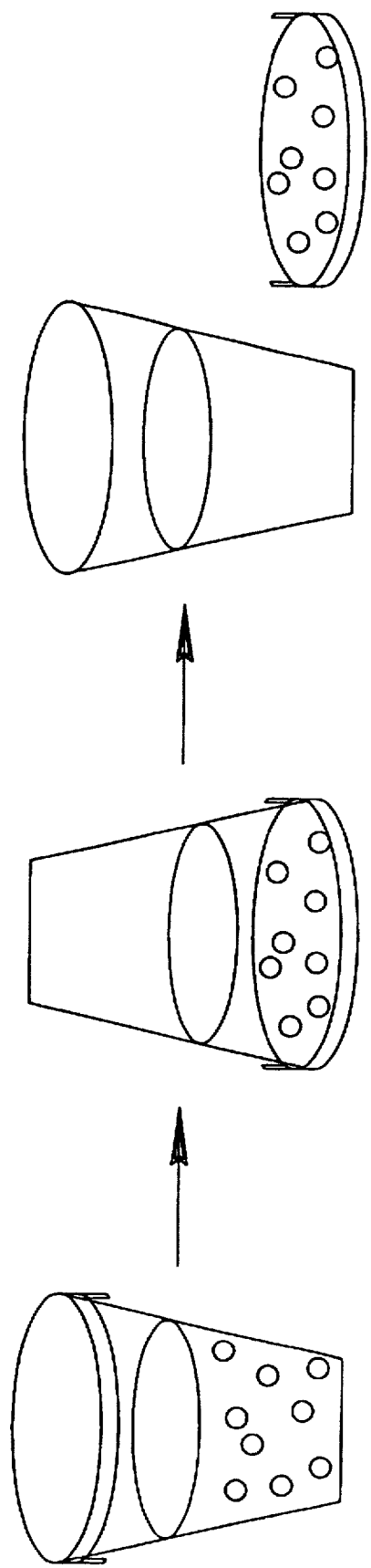
FIG. 27 is a schematic depiction of a reaction tube which serve for affinity separation.

Following amplification, a single-strand specific nuclease, such as, for example, Exonuclease VII, from *E. coli.* which is a processive single-stranded exonuclease that acts from both the 3' and 5' ends of single-stranded DNA and is, therefore, a suitable nuclease to carry out the above function (See, e.g. Berk A. J. et al Cell 12: 721–732 (1977) and Goff S. et al, Proc. Natl. Sci. USA 75: 1763–1767 (1978)), is added to the reaction vessel along with an appropriate buffer. Alternatively, a suitable chemical process aimed at the specific degradation of single stranded sequences is employed. The mixture is incubated at the appropriate conditions (for example at 37° C. for 30 minutes if a nuclease is used) to degrade single-stranded sequences B and B' which are incorporated to amplification products. B and B' sequences which are not incorporated to amplification products are hybridized to one another along with the A and A' targeting sequences of oligonucleotides 1 and 1', respectively, and, therefore, are not nucleated, for example, by the nuclease. The result of the nucleolysis is the release of the label moiety L to the solution, in an amount which is proportional to the level of amplification. The result of the nucleolysis is illustrated in FIG. 26. Label moieties L that where not thus released, these are label moieties conjugated to sequences B or B' that were not incorporated into amplification products, are removed by affinity separation, for example by rotating the reaction vessel by 180°, leading to the adsorption of the separation moiety S, such as biotin, to the screw cap coated with an affinity separation counterpart molecule S', such as avidin in the given example. The released label moiety L, such as for example fluorescein, may thus be, fluorimetrically in the given example, detected. In a preferred embodiment, the counterpart moiety S' is attached to magnetic beads which may be removed from the reaction via rotating the reaction vessel by 180°, leading to the adsorption of the beads to the magnate embedded in the vessels cap as illustrated in FIG. 27.

If, in turn, the target nucleic acid is not included in the examined sample, no amplification occurs, all B and B' sequences are hybridized to one another, no release of detectable label moiety L occurs upon the addition of the single-strand specific nuclease and, therefore, no label is detected in the reaction vessel after the adsorption of the affinity separation moieties to a solid support.

For simplicity purposes the amplification and detection procedures described above refer to the amplification and detection of a single target nucleic acid it should be understood that more oligonucleotide probes per sampled nucleic acid can be employed in the process of the present invention to detect various target nucleic acid sequences or sequence alterations and, as noted above, to detect a sequence alteration using one reaction vessel. Joined oligonucleotide products from different sequences of the same sampled nucleic acid can be distinguished from one another, for example, by using different labels, detection methods, or oligonucleotide probes of distinctively different lengths. It should also be understood that each target nucleic acid sequence may be tested by two sets of oligonucleotide probes. In this case, the detection is monitored twice as a double check.

Advantages of the Method of the Present Invention as Compared With Prior Art Methods according to preferred embodiments of the present invention enjoy a number of advantages relative to methods of prior art aimed at nucleic acid amplification and detection of sequence variations.

As far as the enzyme-based methods such as allele specific oligonucleotide probe (ASO) hybridization; reverse-ASO; restriction site generating PCR (RG-PCR); denaturing/temperature gradient gel electrophoresis (D/TGGE); single-strand conformation polymorphism (SSCP); heteroduplex analysis; restriction fragment length polymorphism (RFLP); PCR restriction fragment length polymorphism (PCR-RFLP); nuclease protection assays; chemical cleavage and other, less frequently used, methods are concerned, the method of the present invention acts as an enzyme-free system for selective amplification of target nucleic acid sequences and enjoys a number of advantages:

First, the method of the present invention do not require highly skilled personnel for (a) accurate execution of the amplification and detection procedures which include one to two simple steps and do not involve complicated steps such as gel electrophoresis and/or complicated blotting and hybridization procedures, and (b) for interpreting the results;

Second, strict calibration steps are not required before the examination of any new DNA alteration;

Third, theoretically, the method of the present invention is suitable for the detection of all sequence alterations;

Fourth, the method of the present invention is easy to automate;

Fifth, the method of the present invention is not based upon the use of enzymes such as DNA and RNA polymerases, restriction endonucleases single-strand-specific endo- and exonucleases and the like, which in addition to being expensive, exhibit lot-to-lot variations in activity and in the concentration of undesired nuclease contaminants.

Figure 3:
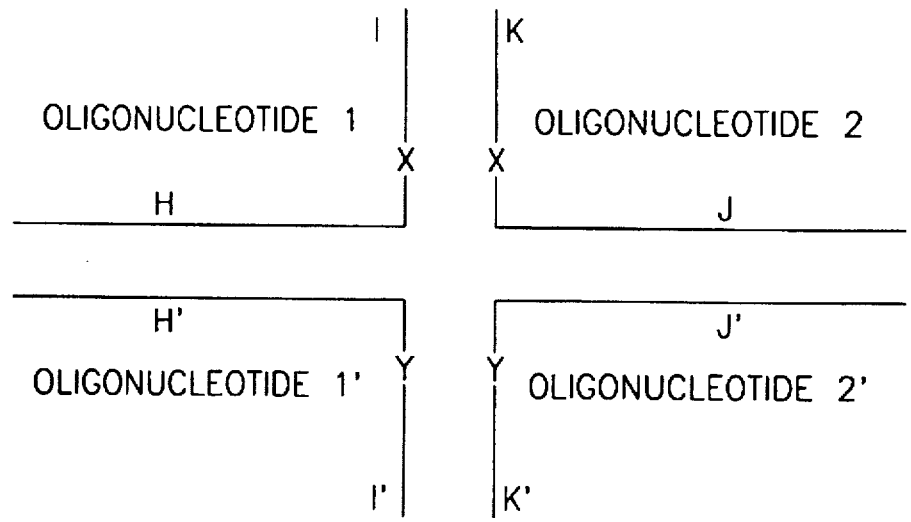
FIG. 3 is a schematic depiction a cross-like structure of a high thermodynamic stability characterizing the oligonucleotide probes used under the CAR method, which upon amplification may result in a template independent false-positive amplification products.

As far as the chemical amplification reaction (CAR) (international PCT application US 94/06690) is concerned:

First, as explained above, the CAR method has a major drawback since a cross-like structure (shown in FIG. 3) of a high thermodynamic stability may form, and upon amplification may result in a template independent false-positive amplification product. The oligonucleotide probes built-up of the methods of the present invention was carefully designed to avoid the formation of target nucleic acid sequence independent stable hybridization structures such as the one shown in FIG. 3. Nevertheless, protecting sequences implemented in the present invention are not limited by their length. This characteristic became advantageous for the detection procedures described above.

Second, the method of the present invention is fully capable of discriminative amplification of sequences differing by a minute sequence alteration such as a point mutation, whereas the CAR method is incompetent in discriminating between target nucleic acid sequences which differ by minute sequence alterations. Therefore, the method of the present invention is suitable for analysis of mutations associated with various genetic diseases as well as detecting the presence of any target nucleic acid sequence in a sample including those of pathogens. The ability of the method of the present invention to detect point mutations is due to the positioning of the chemical functionality groups close to the examined site of the target nucleic acid sequence, that is in the junction between targeting sequences A and A' and protecting sequences B or D and B' or D', respectively, and in the end of targeting sequences C and C'. The positioning of the chemical functionality groups in the CAR method is away from the target nucleic acid sequence, therefore, this method is not sensitive enough to discriminate between sequences which differ by a minute sequence alteration such as a point mutation.

Third, in some of the preferred embodiments of the method of the present invention all reagents required for the amplification and the detection processes are included in the test vessel prior to amplification. Therefore, the present invention is particularly advantageous because of its unique ability to generate a positive or a negative signal without the need to open the test vessel. The simplicity of the detection process is due to the formation of single-stranded protecting sequences B and B' and/or D and D' which are unique to amplification products generated by the method of the present invention.

A method according to the present invention can be used to determine the identity of nucleotide bases at different alleles each of a specific position in nucleic acids of interest via the procedure as described above A method according to the present invention can also be used to type a sample containing nucleic acids. Such a process includes identifying the nucleotide base or bases at each of one or more specific positions, each such nucleotide base being identified using different oligonucleotide probe sets as described above.

A method according to the present invention can be further used to identify different alleles in a sample containing nucleic acids. Such a process includes identifying the nucleotide base or bases present at each of one or more specific positions, each of such nucleotide bases being identified by the method described above.

Another application of a method according to the present invention is in the determination of the genotype of an organism at one or more particular genetic loci. Such a process calls for obtaining from the organism a sample containing genomic, mitochondrial or chloroplast DNA or RNA. The nucleotide base or bases present at each of one or more specific positions in nucleic acids of interest is identified by the process described above. In this way, different alleles are identified and, in turn, the genotype of the organism is determined at one or more particular genetic loci.

The subject invention also provides a method of typing a sample of nucleic acids which consists of identifying the base or bases present at each of one or more specific positions, all such nucleotide bases being identified using the method as outlined above, where each specific position in the nucleic acids of interest is determined using different oligonucleotide probe sets. The identity of each nucleotide base or bases at each position can be determined individually or, preferably, the identities of the nucleotide bases at different positions can be determined simultaneously using for example different label moieties.

The subject invention also provides another method of typing a sample of nucleic acids which comprises determining the presence or absence of one or more particular nucleotides sequences as outlined above.

The subject invention also provides an additional method of typing a sample containing nucleic acids. First, the presence or absence of one or more particular nucleotide sequences is determined as outline above. Second, the nucleotide base or bases present at each of one or more specific positions is identified as outlined above.

The subject invention further provides a method for identifying different alleles in a sample containing nucleic acids which comprises identifying the base or bases present at each of one or more specific positions as outlined above.

Sets of oligonucleotide probes as described above can be used under appropriate hybridization conditions as a kit for diagnosing or typing nucleic acids. The kit further includes the appropriate reagents aimed at the detection of amplification products as outlined above, and suitable buffers, such as an hybridization solution.

Table I lists a sampling of the various diseases which are known to result from the presence of one or more mutations in a gene encoding a specific protein or enzyme. Most of these diseases are recessive diseases, i.e., the diseased individual has both alleles carrying a mutation, the mutation resulting in the protein being absent (gene not expressed); being in an inactive state (having an altered amino acid sequence); or being present in less than the required amounts (significantly reduced gene expression).

TABLE I

| DISEASE | GENE |
| --- | --- |
| Hemophilia A | factor VIII |
| Hemophilia B | factor IX |
| Lesch-Nyhan syndrome | HPRT |
| Ornithine transcarbamylase | OTC |
| Hereditary Amyloidosis (HA) | transthyretin (TTR) |
| Gaucher | glucocerebrosidase |
| Cystic Fibrosis | CFTR |
| Osteogenesis imperfecta | collagen (I, II), procollagen |
| Hemoglobinopathies (e.g., β-thalassemia, Sickle cell anemia) | hemoglobin genes |
| Acute intermittent porphyria (AIP) | uroporphyrinogen I synthetase |
| Phenylketonuria | phenylalanine hydroxylase |
| Tay Sachs | hexosaminidase A (HEXA) |
| Familial hypercholesterolemia (FH) | LDL receptor |
| Neurofibromatosis | NF1 |

The ongoing research to determine the genetic basis for diseases and the advent of technologies such as the polymerase chain reaction (PCR) has resulted in the discovery and complete sequencing of more and more genes encoding structural protein or enzyme products, a mutation in which would lead to either no expression of the gene product or expression of a product which is qualitatively or quantitatively impaired and thereby resulting in a disease. There is thus an ever expanding field of application of the above method of the invention.

The method of the invention, besides having use in diagnosis of specific disease linked mutations in known gene regions, may also be of use in testing for the presence of a specific sequences associate with blood typing, tissue classification—HLA-typing, sex determination or possible susceptibility of an individual to certain diseases. Tissue classifications, for example, may be determined by identifying polymorphism being specific for a particular individual. Screening these known HLA gene sequences by the present method may also be used as a diagnostic tool to determine whether the individuals in question are susceptible to certain diseases, e.g., various specific autoimmune diseases, which are correlated with the specific HLA genes carried by the individual.

As noted above, the method of the invention may also be applied in the field of forensic medicine in which polymorphism in specific genes, e.g., the β-globin gene cluster and the various known repeat sequences, can be determined in, for example, blood or semen samples obtained at the scene of a crime and the results used to indicate whether or not a particular suspect was involved in the crime. Similarly, the aforesaid determination may also be used to determine whether a certain male individual is the father in cases of disputed paternity.

There is evidence that certain cancers may be the result of specific point mutation in the sequence of certain genes and, accordingly, the present methods may be used as an early diagnostic tool to screen the general population or those individuals considered most likely to develop such cancers.

Another application of the present methods, as noted above, is the detection of microorganisms in a sample on the basis of the presence of specific sequences in the sample. For example, an individual suspected of being infected by a microorganism, such as a bacteria or virus, can be tested by using a combination of oligonucleotide probes which anneal only with a specific bacterial and/or viral DNA sequences and not with sequences present in the individual. One example of such an application is in the screening of individuals for the presence of the AIDS virus. Similarly, different species or strains of bacteria in a sample may be distinguished one from the other, e.g., the presence of Shigella vs. Salmonella bacteria which are difficult to distinguish from one another by standard techniques.

Gene regions corresponding to all of those set forth in Table I above and many others, may be analyzed for the presence of one or more point or other mutations at any number of sites within the gene region, or the existence of polymorphism for any specific allele, or whether the individual being tested is homozygous for a specific mutation, heterozygous therefor (i.e. carrier) or whether the individual is normal at this specific location (i.e. carrying two normal alleles).

The present method can be a very effective alternative for the traditional mutation detection methods which use radioactive material, different hybridization or PCR conditions for every mutation, specific gels or an expensive automated sequencer. The present method enables a large scale diagnostic procedure with the possibility of screening many different samples in a short period of time. Furthermore, the present method provides a means for population screening for a wide range of inherited diseases and genetic disorders such as genetic cancers and the like, and can also be easily adapted for screening polymorphism such as those in HLA genes, or detecting for the presence of pathogenic RNA or DNA, or the differentiation among different strains of bacteria or viruses.

The invention will now be further illustrated by the following examples:

EXAMPLE 1

The use of the amplification and the detection methods of the present invention to amplify and detect a 54 base pair DNA sequence contained in the Human Papilloma Virus type 16 genome.

The region to be amplified and detected is a double-stranded sequence which spans nucleotide base numbers 800 to 854 (numbers according to Seedorf, K., et a.. Virology 145, 181–185 (1985)) of the Human Papilloma Virus type 16 (HPV-16) genome, having the sequence (SEQ. ID. NO. 1):

5'-AGACCTGTTAATGGGCACACTAGGAAT-
TGTGTGCCCCATCTGTTCTCAGAAACC-3'

3'-TCTGGACAATTACCCGTGTGATCCTTAA-
CACACGGGGTAGACAAGAGTCTTTGG-5'

Four oligonucleotide probes, designated 1, 1', 2 and 2', are used to amplify the above target sequence, which oligonucleotide probes have the following sequences:

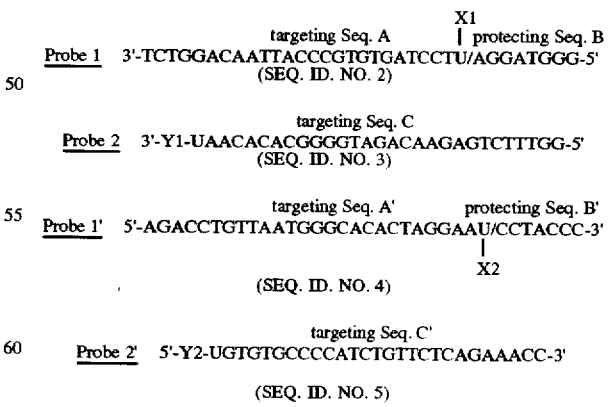

The backslash lines merely depict the demarcation between targeting sequences A and A' and protecting sequences B and B' of oligonucleotide probes 1 and 1', respectively. The single vertical lines indicate a chemical bond that attaches chemical functionality groups X1 and X2 to a substituent group on uridine residues which are located at the end of targeting sequence A and A', between the junctions of targeting sequences A and A' and protecting sequences B and B' of oligonucleotide probes 1 and 1', respectively.

In this example a Diels-Alder reaction between X and Y chemical functionality groups is illustrated. Furthermore, in this example X1 and X2 chemical functionality groups are the same so as Y1 and Y2 chemical functionality groups, therefore, they shall be referred to as X and Y chemical functionality groups in this example.

As can be seen in the above listed oligonucleotide probes, X and Y chemical functionality groups are attached to uridine residues. Y groups, which serve as dienophiles in the Diels-Alder reaction, are each attached to a 2' aminomethyl uridine via the C-2' position of the ribose moiety, whereas X groups which serve as dienes are each attached to the C-5 position of the uridine base moiety.

Synthesis of 2'-trifluoroacetamidomethyluridine phosphoramidite derivative for the attachment of Y groups to probes 2 and 2' via a 2' position of a uridine residue.

A uridine residue is modified so that a desired chemical functionality group can later be covalently attached to it, after which conventional methods are used to synthesize the oligonucleotide probes in a stepwise manner and the modified uridine is positioned in any desired location. Once the oligonucleotide probes are synthesized, Y chemical functionality groups are attached to the modified uridine residues. In this example, Y chemical functionality groups of probes 2 and 2', are a 2-butenedioic acid derivative.

1. Synthesis of 2'-deoxy-2'-C-trifluoroacetamidomethyluridine.

The nucleoside 2'-deoxy-2'C-azidomethyluridine may be prepared according to procedure described in Ioannidis et al, Nucleosides & Nucleotides, 11: 1205 (1992). Thus, a solution containing 10 mmoles azido compound (2.83 grams) in methanol (200 ml) is prepared and is vigorously stirred in a hydrogen atmosphere with 10% palladium-on-carbon catalyst (1.4 grams) for 60 minutes. The mixture is filtered and evaporated, and the aminomethyluridine is left as an oily crude. The aminoproduct, thus prepared, is employed in the following step 2 without further purification.

To a solution (50 ml) containing 10 mmoles C-2'-aminomethyluridine (2.5 grams) and 10 mmoles of triethylamine (1.1 grams) in ethylacetate which is cooled to 0° C., a solution containing 11 mmoles trifluoroacetic anhydride (2.31 grams) in Ethyl acetate (30 ml) is added dropewise. The mixture is stirred for 3 hours and then extraction with ethylacetate-water is performed. The organic layer is washed with brine and dried with anhydrous sodium sulpfhate. The solvent is evaporated to dryness. For further purification the product may be separated on a silica-gel column.

2. Preparation of 5'-dimethoxytrityl-2'-C-trifluroacetamidomethyluridine.

A solution containing 10 mmoles 4,4'-dimethoxytrityl chloride (3.38 grams) in dry pyridine is added dropewise to a cooled (0° C.) solution of dry pyridine (100 ml) containing 10 mmoles trifluoroacetamidouridine (3.54 grams). The mixture is stirred for 3 hours, and the pyridine is evaporated to dryness. The oily product is dissolved in ethylacetate and washed with water, brine, and the organic layer is dried with anhydrous sodium sulfate. The mixture is evaporated to dryness, and the product may be further purified on a silica-gel column.

3. Preparation of 5'-dimethoxytrityl-3'- (2-cyanoethyl N,N-diisopropyl) phosphoramidite-2'-C-trifluoroacetamidomethyluridine.

Ten mmoles of 5'-dimethoxytrityl-2'-C-trifluoroacetamido-methyluridine (6.56 grams) and 20 mmoles of N,N-diisopropylethylamine (2.60 grams) are dissolved in dry dichloromethane (50 ml) under Argon, and the solution is kept at 0° C. To this solution, 10 mmoles of 2-cyanoethyl N,N-diisopropylchlorophosphoramidite (Aldrich) (2.36 grams) in 25 ml of dry dichloromethane is added dropwise. The reaction is stirred for 10 minutes, and kept at room temperature for 10 more minutes. Ethyl acetate (250 ml) is added to the mixture, and is extracted three times with brine. The solvent is removed under vacuum, toluene (50 ml) is added, and the mixture is lyophilized, leaving white powder which is collected under Argon.

Derivatization of uridine at C-5 position for the attachment of X chemical functionality groups to probes 1 and 1' via uridine phosphoramidite derivative.

In this example, X chemical functionality groups of probes 1 and 1', are each a diene which is derived from the attachment of a double bond C=C to the C-5 position of a uridine base. Several dienes could be attached. The attachment of a double bond to the C-5 position of uridine is described by Bergstrom et al in J. Amer. Chem. Soc., 100: 8106 (977). The preferred example is the attachment of propylene to the C-5 position according to this reference.

The preparation of the 5'-dimethoxytrityl-C-5-propylene-3'-(2-cyanoethyl N,Ndiisopropyl) phosphoramidite is accomplished according to Ruth J. R. et al in DNA 4: 93, (1985) and EP 135 587, and as described above.

All of the oligonucleotides listed above are synthesized and purified by the following procedure.

1. Automated Synthesis Procedures.

2-cyanoethyl phosphoramidites are purchased from Applied Biosystems Inc. The automated synthesis procedure includes condensation of nucleoside phosphoramidites to 30 mg of a nucleoside-derivatized controlled pore glass (CPG) bead support (500 Angstrom pore diameter), using type 380B-02DNA synthesizer from Applied Biosystems Inc. The cycles (30 minutes each) include detritylation with 2% trichloroacetic acid in dichloromethane; condensation using tetrazol as an activating proton donor; capping with acetic anhydride and dimethylaminopyridine; detritylation using 2% trichloroacetic acid in dichloromethane; and oxidation of the phosphite to the phosphate with $0.1M$ $I_2/H_2O$/lutidine/tetrahydrofuran. Yields at each step are essentially quantitative and are monitored by collecting the dimethoxytrityl alcohol released during detritylation and examining it spectroscopically.

2. Oligodeoxyribonucleotide Deprotection and Purification Procedures.

The solid support is removed from the column and exposed to 1 ml concentrated ammonium hydroxide for 16 hours at 60° C. in a closed tube. Ammonia is removed and the residue is applied to a preparative 12% polyacrylamide gel containing 7M urea using a Tris-borate-EDTA (TBE) buffer (pH 8.0). Electrophoresis is carried out at 20 volts/cm for 5 hours, after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The aqueous phase is placed on top of a Sephadex G50 column (Pharmacia) (1×10 cm) and is eluted with double distilled water. The eluate is monitored by UV absorbance at 260 nm and the appropriate fractions are collected, quantified by UV absorbance in a fixed volume and evaporated to dryness at room temperature in a vacuum centrifuge.

Reaction of maleic anhydride with aminomethyl groups attached to uridine residues to prepare the Y chemical functionality groups of probes 2 and 2'.

Aliquots of oligonucleotide probes 2 and 2' containing 2'-aminomethyl-2'-deoxyuridine having an optical density of 5.0 (5.0 O.D.) are lyophilized to dryness each in a 1.5 ml disposable eppendorf tubes. Each probe preparation is reconstituted in 200 µl of 1M sodium borate buffer (pH 9.3).

To attach Y chemical functionality groups, 200 μl solution of maleic anhydride (Aldrich) dissolved in dimethyl sulfoxide (DMSO) at a concentration of 20 mg/ml is added to each of the vials which are then agitated at room temperature (RT) for approximately 12 hours. Each of the mixtures is then desalted and purified from excess chemical functionality group reagent via centrifugation through a Pharmacia Sephadex NAP-10 column. Each of the resulting solutions is purified on a Sephadex G50 column (Pharmacia) (1×10 cm). Each eluate is monitored by UV absorbance at 260 nm and the appropriate fractions are collected and are quantified by UV absorbance in a fixed volume. Each of the probes, 2 and 2', is lyophilized to dryness and stored at 4° C. until used.

Amplification

The HPV-16 sequence is, for example, contained in a plasmid which is prepared by cloning the HPV-16 sequence published by Seedorf et al., in Virology 145, 181–185 (1985) in a blue script vector (Stratagene) and is dissolved in double distilled water at a concentration of 20 ng/ml.

The amplification procedure of the HPV-16 sequence shown above (SEQ. ID. NO. 1) according to the method of invention involves the following steps:

$10^{11}$ molecules of each of the oligonucleotide probes (1, 1', 2 and 2') are reconstituted in hybridization buffer at a final volume of 100 μl. The hybridization buffer contains 30% deionized formamide in water (vol/vol)(optional), 0.54M NaCl, 30 mM sodium phosphate (pH 7.4), 0.3 mM EDTA, 5% dextran sulfate 500K m.w. (Sigma)(w/vol) and 0.1% Triton X-100.

To an eppendorf tube (Perkin Elmer), containing a 1 μl sample of the HPV-16 target sequence described above, 99 μl of the hybridization buffer containing the four oligonucleotide probes, 1, 1', 2, and 2', is added. A second tube, which serves as control, contains all reagents but the target sequence in a final volume of 100 μl. The solution in each of the tubes is gently vortexed. 100 μl of mineral oil is added to each of the tubes, to prevent evaporation during the repeated heating cycles of the amplification reaction.

The tubes are placed in a DNA thermal cycler (Perkin Elmer, Cetus) and are subjected to 30 heating and cooling cycles. Each cycle consists of a 65 second incubation at 90° C. and a 240 second incubation at 40° C.

After cycling, 20 μl of each solution is mixed with 2 μl of 40% glycerol in 1×TBE (pH 8.0) containing bromphenol blue dye and is electrophorased on a 12% polyacrylamide gel using 1×TBE buffer (pH 8.0) at 20 volts/cm for three hours, after which the gel is immersed in a 100 ml solution of ethidium bromide (0.5 mg/ml in H$_2$O), for 45 minutes at room temperature. The gel is exposed to Polaroid photographic film, type 57 or 667 (ASA 3000) for 5 second at f8, under an efficient ultra-violet (UV) light source (72,500 mW/cm$^2$) and a band of joined oligonucleotide products in an amount as small as 10 ng may thus be detected.

EXAMPLE 2

In situ nonradioactive detection of the amplified products using Exonuclease VII For the in situ nonradioactive detection of the amplified products using Exonuclease VII oligonucleotide probes 2 and 2' are used as in Example 1 whereas to the 5'-end of oligonucleotide probe 1 attached is a Fluorescein molecule and to the 5'-end of oligonucleotide probe 1' a biotin molecule is attached, as shown below:

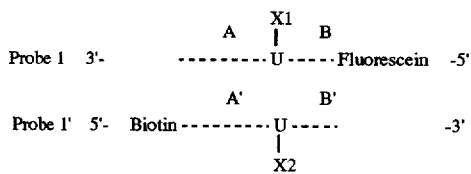

In order to attach fluorescein and biotin to the 5' end of oligonucleotide probes 1 and 1', respectively, the reagents fluorescein phosphoramidite and biotin phosphoramidite (Glenn Research) are used, respectively.

The oligonucleotide probes synthesis and purification is accomplished as exemplified in example 1.

For amplification, a reaction tube is constructed as follows:

A plastic transparent tube which is divided to two compartments separated by a destructible separation, which compartments are situated one on top of the other, is used, wherein the internal separation is coated with avidin (Sigma) on the side facing the lower compartment. The lower compartment contains the reaction mixture, whereas the upper compartment contains 0.4 units of Exonuclease VII in a buffer which consists of 70 mM Tris.Cl, pH 8.0; 8 mM EDTA; 10 mM β-mercaptoethanol; and 50 μg/ml BSA.

Following amplification, the reaction tube is kept at 37° C., and the content of the upper compartment is squeezed out through the destructible separation to mix with the content of the lower compartment containing the amplification products. The reaction mixture is incubated for 30 minutes, to cleave single-stranded B and B' protecting sequences.

After the Exonuclease VII treatment, the reaction tube is rotated at 180°, and is kept at the upside down position for 10 minutes to allow the capture of biotinylated double-stranded DNA to the avidin coated cap. The reaction tube is re-rotated at 180°, and the fluorescein released to the solution from single-stranded B fragment, via the nuclease activity, is detected by a fluorometer (Perkin Elmer).

EXAMPLE 3

The use of the amplification and the detection methods of the present invention to detect the codon 245 (GGC→GAC) point mutation of the human p53 gene.

Two oligonucleotide probe sets are designed to amplify an 58 bp fragment of the human p53 gene. The first oligonucleotide probes set is designed to amplify the wild-type sequence of the gene which have the following sequence (SEQ. ID. NO. 6):

The second oligonucleotide probes set is designed to amplify the mutant sequence of the gene which have the following sequence (SEQ. ID. NO. 7):

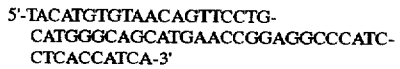

Oligonucleotide probes of the first set includes:

```
                                  X1
              targeting Seq. A   |  protecting Seq. B
probe 1   3'-ATGTACACATTGTCAAGGACGTACCCGCC/CGGAATCATC-flourescein-5'    (SEQ. ID. NO. 8)

targeting Seq. C
probe 2   5'-TGATGGTGAGGATGGGCCTCCGGTTCATG-Y1-3'   (SEQ. ID. NO. 9)

X2
              targeting Seq. A'  |  protecting Seq. B'
probe 1'  5'-TACATGTGTAACAGTTCCTGCATGGGCGG/GCCTTAGTAG-3'    (SEQ. ID. NO. 10)

targeting Seq. C'
probe 2'  3'-ACTACCACTCCTACCCGGAGGCCAAGTAC-Y2-5'   (SEQ. ID. NO. 11)
```

The detection method for the wild-type sequence amplified using the first oligonucleotide probes set is proximity energy transfer labeling. As a first detection oligonucleotide probe serve protecting sequence B of oligonucleotide probe 1. The first detection oligonucleotide probe is conjugated to a flourescein proximity label. A second detection oligonucleotide probe B.1 (shown below; SEQ. ID. NO. 12) is being conjugated to a corresponding second rhodamine proximity label moiety. The two labeled detection oligonucleotide probes hybridize to one another and therefore bring the proximity label moieties flourescein and rhodamine to a proximity which is sufficient for their interaction to produce a detectable signal. When the two labeled detection oligonucleotide probes are hybridized, proximity labeling moieties flourescein and rhodamine are brought into proximity that enables an energy transfer reaction between them to occur, resulting in a measurable energy emission which may be measured flourometrically (excitation 472 nm, readout 577 nm).

```
probe B.1   5'-GCCTTAGTAG-3'   (SEQ. ID. NO. 12)
               |
            rhodamine
```

Oligonucleotide probes of the second set includes:

The oligonucleotide probes synthesis and purification is accomplished essentially as exemplified in example 1.

The experiment described under this example is aimed at the determination of the genotype at codon 245 of the p53 gene of an examined individual, and is based on a simultaneous amplification procedure, combined with a simultaneous detection procedure of both the wild-type and the mutant sequences, which of which exist in the examined individuals genomic DNA is to be determined.

For the combined amplification and detection reactions, tubes are constructed as follows:

Transparent tubes which have a magnate embedded in their caps, as is described in FIG. 27, are used as containers for the experimental and control amplification reactions which are performed essentially as described under Example 1, except for the use of two oligonucleotide probe sets in each tube in this Example, whereas only one set is employed under Example 1.

The experimental tube contains genomic DNA obtained from an individual whose genotype is to be determined. As controls to this combined amplification and detection procedures, four additional similar tubes are employed. The first contains no target DNA sequence and therefore serve as a negative control and should result in no signal obtained by either of the detection methods. The second contains genomic DNA from an individual previously shown to be

```
                                  X3
              targeting Seq. A   |  protecting Seq. D
probe 3   3'-ATGTACACATTGTCAAGGACGTACCCGCT/ATCGATAACG-isoluminol-5'    (SEQ. ID. NO. 13)

targeting Seq. C
probe 4   5'-Biotin-TGATGGTGAGGATGGGCCTCCGGTTCATG-Y3-3'   (SEQ. ID. NO. 14)

X4
              targeting Seq. A'  |  protecting Seq. D'
probe 3'  5'-TACATGTGTAACAGTTCCTGCATGGGCAG/TAGCTATTGC-3'    (SEQ. ID. NO. 15)

targeting Seq. C'
probe 4'  3'-ACTACCACTCCTACCCGGAGGCCAAGTAC-Y4-5'   (SEQ. ID. NO. 16)
```

The detection method for the mutant sequence amplified using the second oligonucleotide probes set is based upon the release of a Isoluminol label moiety conjugated to single-stranded D sequence which is incorporated into amplification products, and the removal of all double-stranded D sequences along with the Isoluminol label moieties conjugated to them from the test vessel via an affinity separation moiety biotin conjugated to oligonucleotide probe 4. The single-stranded D sequence is nucleated post amplification via the nucleolitic activity of Exonuclease VII from E. coli, which is a single-stranded specific nuclease. This results in the release of the Isoluminol label moiety conjugated to single-stranded D sequences, to the surrounding solution. Isoluminol label moieties that where not thus released, these are label moieties conjugated to sequences D that were not incorporated into amplification products, are removed by affinity separation. The released Isoluminol label moieties may thus be detected luminometrically.

homozygous to the wild-type allele and therefore serve as a positive control for the first detection method and as a negative control to the second detection method and should result in a detectable signal of the first but not the second detection method. The third contains genomic DNA from an individual previously shown to be homozygous to the mutant allele and therefore serve as a positive control for the second detection method and as a negative control to the first detection method and should result in a detectable signal of the second but not the first detection method. The fourth contains genomic DNA from an individual previously shown to be heterozygous to the wild-type and the mutant alleles and therefore serve as a positive control for the first and second detection method and should result in a detectable signal of the first and the second detection methods.

Following amplification the second detection oligonucleotide probe B.1, described above, is added to the reaction tubes and is allowed to hybridize with the single-stranded B sequences incorporated into amplification products, which, as described, serve as the first detection oligonucleotide probes, if any are present.

Following detection of the proximity labeling signal, the reaction tube is brought to 37° C., and 0.4 units of Exonuclease VII in a buffer which consists of 70 mM Tris.Cl, pH 8.0; 8 mM EDTA; 10 mM β-mercaptoethanol; 50 μg/ml BSA is added to the tube. The reaction mixture is incubated for 30 minutes, to cleave single-stranded D protecting sequences. After the Exonuclease VII treatment, avidin coated magnetic beads are added to the reaction tube which is placed on a shaker for 10 minutes, to allow capturing of the biotinylated double-stranded DNA to the avidin molecules. The reaction tube is rotated at 180° to allow the magnetic beads to adhere to the cap, after which the reaction tube is re-rotated at 180°, and the Isoluminol released to the solution from single-stranded D fragment, via the nuclease activity, is detected by a luminometer (Perkin Elmer).

If the first detection method yielded a positive signal, than the examined nucleic acid contains the wild-type sequence whereas if the first detection method did not yield a signal than the examined nucleic acid does not contain the wild-type sequence. If the second detection method yielded a positive signal than the examined nucleic acid contains the mutant sequence whereas if the second detection method did not yield a signal than the examined nucleic acid does not contain the mutant sequence.

This give rise to three alternative results: (1) if the first detection method yielded a positive result whereas the second did not, the examined DNA sample is homozygous for the codon 245 (GGC) of the human p53 gene; (2) if the second detection method yielded a positive result whereas the first did not, the examined DNA sample is homozygous for the codon 245 (GAC) point mutation of the human p53 gene; (3) if, on the other hand, both, first and second, detection methods yielded a positive signal, then the examined DNA sample is heterozygous at codon 245 of the human p53 gene, that is one allele has the wild-type sequence whereas the second allele has the mutant sequence.

EXAMPLE 4

Diagnostic kits for carrying out a preferred embodiment of the methods according to the present invention detailed above may contain the following constituents:

A diagnostic kit for amplifying specific nucleotide sequences in samples, consists of two or more oligonucleotide probes complementary pairs and at least one buffer.

One diagnostic kit for detecting the presence of specific nucleotide sequences in samples, consists: (a) two or more oligonucleotide probes complementary pairs; (b) two or more detection oligonucleotide probes conjugated to a proximity labeling moiety; and (c) at least one buffer;

A second diagnostic kit for detecting the presence of specific nucleotide sequences in samples, consists: (a) two or more oligonucleotide probes complementary pairs, one or more are conjugated to a separation moiety, and one or more are conjugated to a label moiety; (b) a single-strand specific nuclease; and (e) a solid support for affinity separation of amplification products.

When the kits are to be used in the screening for the presence of one or all of the various known genetic diseases, e.g., those listed in Table I above, it may contain any suitable number oligonucleotide probes in any suitable combination for screening for mutations in particular disease related genes. In cases where a particular disease related gene may have one or more mutations, e.g., the CFTR gene, the kit should contain the specific oligonucleotide probes for screening the more common of the mutations, which may be different for different intended populations. When the kit is to be used for blood or tissue typing analysis it may contain any combination of oligonucleotide probes, each designed to identify a particular blood or tissue type. Depending on the circumstances, all of the kits may also contain an additional oligonucleotide probes for determining the presence or absence of a nucleic acid sequence corresponding specifically to the presence of a pathogen, for example, the presence of the AIDS virus or a specific strain of such virus, e.g., HIV-I, HIV-II or HIV-III. Accordingly, one kit may be used for testing any number of genes or gene sites within a single gene, and this only requires that the kit contain a number of the specific oligonucleotide probes, all the other components of the kit being the same in all cases.

While the invention has been described with respect to a limited number of embodiments, it will be appreciated that many variations, modifications and other applications of the invention may be made.

---

---

What is claimed is:

1. A process for amplifying and detecting, in a sample containing a nucleic acid of interest, a single stranded target nucleic acid molecule including a target sequence or a double stranded nucleic acid target molecule including a target sequence and target complementary sequence, the process comprising the steps of:

(a) contacting a first oligonucleotide probe complement pair and a second oligonucleotide probe complement pair with stretches of nucleotide bases present in the nucleic acids of interest, wherein:

(i) said first oligonucleotide probe complement pair includes oligonucleotide probe 1 and oligonucleotide probe 1' and the second oligonucleotide probe complement pair includes oligonucleotide probe 2 and oligonucleotide probe 2';

(ii) said oligonucleotide probe 1 includes a targeting sequence A, said oligonucleotide probe 1' includes a targeting sequence A', said oligonucleotide probe 2 includes a targeting sequence C and said oligonucleotide probe 2' includes a targeting sequence C';

(iii) one of said oligonucleotides of each of said first and second oligonucleotide probe pairs includes a protecting sequence B and B', respectively;

(iv) said targeting sequence A of oligonucleotide probe 1 and said targeting sequence A' of oligonucleotide probe 1' are complementary to each other;

(v) said targeting sequence C of oligonucleotide probe 2 and said targeting sequence C' of oligonucleotide probe 2' are complementary to each other;

(vi) said oligonucleotide probes 1 and 2 form a first oligonucleotide pair such that said targeting sequence A of oligonucleotide probe 1 and said targeting sequence C of oligonucleotide probe 2 are complementary to adjacent portions of the target sequence;

(vii) said oligonucleotide probes 1' and 2' form a second oligonucleotide pair such that said targeting sequence A' of oligonucleotide probe 1' and said targeting sequence C' of oligonucleotide probe 2' are complementary to adjacent portions of the target complementary sequence;

(viii) said protecting sequence B does not hybridize to the target sequence when said targeting sequence A and targeting sequence C hybridize to the target sequence;

(ix) said protecting sequence B' does not hybridize to the target complementary sequence when said targeting sequence A' and targeting sequence C' hybridize to the target complementary sequence;

(x) a chemical functionality group X1 is attached to a sugar or base moiety of the last nucleotide in said targeting sequence A of oligonucleotide probe 1, a chemical functionality group Y1 is attached to a sugar or base moiety of the last nucleotide in said targeting sequence C of oligonucleotide probe 2, said chemical functionality group X1 is reactive with said chemical functionality group Y1;

(xi) a chemical functionality group X2 is attached to a sugar or base moiety of the last nucleotide in said targeting sequence A' of oligonucleotide probe 1', a chemical functionality group Y2 is attached to a sugar or base moiety of the last nucleotide in said targeting sequence C' of oligonucleotide probe 2', said chemical functionality group X2 is reactive with said chemical functionality group Y2;

(xii) when said targeting sequence A and said targeting sequence C hybridize to the target sequence, said chemical functionality group X1 reacts with said chemical functionality group Y1 to form a first chemical bond, and a complementary strand of joined oligonucleotide product is formed, whereas when said targeting sequence A' and said targeting sequence C' hybridize to the target complementary sequence, said chemical functionality group X2 reacts with said chemical functionality group Y2 to form a second chemical bond, and a complementary strand of joined oligonucleotide product is formed;

(b) providing hybridization conditions permitting said targeting sequence A of oligonucleotide probe 1 and said targeting sequence C of oligonucleotide probe 2 to hybridize with said adjacent portions of the target sequence and permitting said targeting sequence A' of oligonucleotide probe 1' and said targeting sequence C' of oligonucleotide probe 2' to hybridize with said adjacent portions of the target complementary sequence;

(c) providing conditions permitting joining of said oligonucleotide probe 1 and oligonucleotide probe 2 to each other by forming said first chemical bond between said chemical functionality groups X1 and Y1, thereby forming said first joined oligonucleotide product having the target complementary sequence;

(d) providing conditions permitting joining of said oligonucleotide probe 1' and oligonucleotide probe 2' to each other by forming said second chemical bond between said chemical functionality groups X2 and Y2, thereby forming said second joined oligonucleotide product having the target sequence;

(e) treating the sample under a denaturing condition;

(f) repeating steps (b) through (e) a desired number of times; and (g) detecting the joined oligonucleotide products.

2. A process for linear amplification and detection, in a sample containing a nucleic acid of interest, of a target nucleic acid molecule including a target sequence, the process comprising the steps of:

(a) contacting an oligonucleotide probe pair with stretches of nucleotide bases present in the nucleic acids of interest, wherein:

(i) said oligonucleotide probe pair includes an oligonucleotide probe 1 and an oligonucleotide probe 2;

(ii) said oligonucleotide probe 1 includes a targeting sequence A and said oligonucleotide probe 2 includes a targeting sequence C;

(iii) one of said oligonucleotides includes a protecting sequence B;

(iv) said targeting sequence A of oligonucleotide probe 1 and said targeting sequence C of oligonucleotide probe 2 are complementary to adjacent portions of the target sequence;

(v) said targeting sequence A' of oligonucleotide probe 1' and said targeting sequence C' of oligonucleotide probe 2' are complementary to adjacent portions of the target complementary sequence;

(vi) said protecting sequence B does not hybridize to the target sequence when said targeting sequence A and targeting sequence C hybridize to the target sequence;

(vii) said protecting sequence B' does not hybridize to the target complementary sequence when said targeting sequence A' and said targeting sequence C' hybridize to the target complementary sequence;

(viii) a chemical functionality group X1 is attached to a sugar or base moiety of the last nucleotide in said sequence A of oligonucleotide probe 1, a chemical functionality group Y1 is attached to a sugar or base moiety of the last nucleotide in said sequence C of oligonucleotide probe 2, said chemical functionality group X1 is reactive with said chemical functionality group Y1;

(ix) a chemical functionality group X2 is attached to a sugar or base moiety of the last nucleotide in said sequence A' of oligonucleotide probe 1', a chemical functionality group Y2 is attached to a sugar or base moiety of the last nucleotide in said sequence C' of oligonucleotide probe 2', said chemical functionality group X2 is reactive with said chemical functionality group Y2;

(x) when said targeting sequence A and targeting sequence C hybridize to the target sequence, said chemical functionality group X1 reacts with said chemical functionality group Y1 to form a chemical bond, and a complementary strand of joined oligonucleotide product is formed, whereas when said targeting sequence A' and targeting sequence C' hybridize to the target complementary sequence, said chemical functionality group X2 reacts with said chemical functionality group Y2 to form an alternative chemical bond, a complementary strand of joined oligonucleotide product is formed;

(b) providing hybridization conditions permitting targeting sequence A of oligonucleotide probe 1 and targeting sequence C of oligonucleotide probe 2 to hybridize with adjacent portions of the target sequence and permitting targeting sequence A' of oligonucleotide probe 1' and targeting sequence C' of oligonucleotide probe 2' to hybridize with adjacent portions of the target complementary sequence;

(c) providing conditions permitting joining of said oligonucleotide probe 1 and oligonucleotide probe 2, hybridized after step (b) to said adjacent portions of the target sequence to each other by forming said chemical bond between said chemical functionality groups X1 and Y1, thereby forming said joined oligonucleotide product having the target complementary sequence, and joining of said oligonucleotide probe 1' and oligonucleotide probe 2', hybridized after step (b) to said adjacent portions of the target complementary sequence to each other by forming said alternative chemical bond between said chemical functionality groups X2 and Y2, thereby forming said joined oligonucleotide product having the target sequence;

(d) treating the sample under a denaturing condition;

(f) repeating steps (b) through (d) a desired number of times; and (g) detecting said joined oligonucleotide product.

3. A process for amplifying and detecting, in a sample containing a nucleic acid of interest, a nucleic acid molecule including a wild type target sequence, a mutant target sequence, a wild-type target complementary sequence and/ or a mutant target complementary sequence, in a single or double stranded form, the process comprising the steps of:

(a) contacting a first, second, third and fourth oligonucleotide probe complement pairs with stretches of nucleotide bases present in the nucleic acids of interest, wherein:

(i) said first oligonucleotide probe complement pair includes oligonucleotide probe 1 and oligonucleotide probe 1', said second oligonucleotide probe complement pair includes oligonucleotide probe 2 and oligonucleotide probe 2', said third oligonucleotide probe complement pair includes oligonucleotide probe 3 and oligonucleotide probe 3' and said fourth oligonucleotide probe complement pair includes oligonucleotide probe 4 and oligonucleotide probe 4';

(ii) said oligonucleotide probes 1 and 3 each includes a targeting sequence A, said oligonucleotide probes 1' and 3' each includes a targeting sequence A', said oligonucleotide probes 2 and 4 each includes a targeting sequence C, said oligonucleotide probes 2' and 4' each includes a targeting sequence C';

(iii) one of said oligonucleotides of each of said first and second oligonucleotide probe pairs includes a protecting sequence B and B', respectively, whereas one of said oligonucleotides of each of said third and fourth oligonucleotide probe pairs includes a protecting sequence D and D', respectively;

(iv) said targeting sequence A of oligonucleotide probe 1 and said targeting sequence A' of oligonucleotide probe 1' are complementary to each other, said targeting sequence A of oligonucleotide probe 3 and said targeting sequence A' of oligonucleotide probe 3' are complementary to each other;

(v) said targeting sequence C of oligonucleotide probe 2 and said targeting sequence C' of oligonucleotide probe 2' are complementary to each other, said targeting sequence C of oligonucleotide probe 4 and said targeting sequence C' of oligonucleotide probe 4' are complementary to each other;

(vi) said oligonucleotide probes 1 and 2 form a first oligonucleotide pair such that said targeting sequence A of oligonucleotide probe 1 and said targeting sequence C of oligonucleotide probe 2 are complementary to adjacent portions of the wild type target sequence, said oligonucleotide probes 3 and 4 form a third oligonucleotide pair such that said targeting sequence A of oligonucleotide probe 3 and said targeting sequence C of oligonucleotide probe 4 are complementary to adjacent portions of the mutant target sequence;

(vii) said oligonucleotide probes 1' and 2' form a second oligonucleotide pair such that said targeting sequence A' of oligonucleotide probe 1' and said targeting sequence C' of oligonucleotide probe 2' are complementary to adjacent portions of the wild type target complementary sequence, said oligonucleotide probes 3' and 4' form a fourth oligonucleotide pair such that said targeting sequence A' of oligonucleotide probe 3' and said targeting sequence C' of oligonucleotide probe 4' are complementary to adjacent portions of the mutant target complementary sequence;

(viii) said protecting sequences B, B', D and D' does not hybridize to the nucleic acid of interest when said targeting sequences hybridize to the nucleic acid of interest;

(x) a chemical functionality group X1 is attached to a sugar or base moiety of the last nucleotide in said targeting sequence A of oligonucleotide probe 1, a chemical functionality group Y1 is attached to a sugar or base moiety of the last nucleotide in said targeting sequence C of oligonucleotide probe 2, said chemical functionality group X1 is reactive with said chemical functionality group Y1, a chemical functionality group X3 is attached to a sugar or base moiety of the last nucleotide in said targeting sequence A of oligonucleotide probe 3, a chemical functionality group Y3 is attached to a sugar or base moiety of the last nucleotide in said targeting sequence C of oligonucleotide probe 4, said chemical functionality group X3 is reactive with said chemical functionality group Y3;

(xi) a chemical functionality group X2 is attached to a sugar or base moiety of the last nucleotide in said targeting sequence A' of oligonucleotide probe 1', a chemical functionality group Y2 is attached to a sugar or base moiety of the last nucleotide in said targeting sequence C' of oligonucleotide probe 2', said chemical functionality group X2 is reactive with said chemical functionality group Y2, a chemical functionality group X4 is attached to a sugar or base moiety of the last nucleotide in said targeting sequence A' of oligonucleotide probe 3', a chemical functionality group Y4 is attached to a sugar or base moiety of the last nucleotide in said targeting sequence C' of oligonucleotide probe 4', said chemical functionality group X4 is reactive with said chemical functionality group Y4;

(xii) when said targeting sequence A and said targeting sequence C hybridize to the wild type target sequence, said chemical functionality group X1 reacts with said chemical functionality group Y1 to form a first chemical bond, and a wild type complementary strand of joined oligonucleotide product is formed, when said targeting sequence A' and said targeting sequence C' hybridize to the wild type target complementary sequence, said chemical functionality group X2 reacts with said chemical functionality group Y2 to form a second chemical bond, and a wild type complementary strand of joined oligonucleotide product is formed, when said targeting sequence A and said targeting sequence C hybridize to the mutant target sequence, said chemical functionality group X3 reacts with said chemical functionality group Y3 to form a third chemical bond, and a mutant complementary strand of joined oligonucleotide product is formed, whereas when said targeting sequence A' and said targeting sequence C' hybridize to the mutant target complementary sequence, said chemical functionality group X4 reacts with said chemical functionality group Y4 to form a fourth chemical bond, and a mutant complementary strand of joined oligonucleotide product is formed;

(b) providing hybridization conditions permitting said targeting sequence A of oligonucleotide probe 1 and said targeting sequence C of oligonucleotide probe 2 to hybridize with said adjacent portions of the wild type target sequence, permitting said targeting sequence A' of oligonucleotide probe 1' and said targeting sequence C' of oligonucleotide probe 2' to hybridize with said adjacent portions of the wild type target complementary sequence, permitting said targeting sequence A of oligonucleotide probe 3 and said targeting sequence C of oligonucleotide probe 4 to hybridize with said adjacent portions of the mutant target sequence and permitting said targeting sequence A' of oligonucleotide probe 3' and said targeting sequence C' of oligonucleotide probe 4' to hybridize with said adjacent portions of the mutant target complementary sequence;

(c) providing conditions permitting:
  (i) joining of said oligonucleotide probe 1 and oligonucleotide probe 2 to each other by forming said first chemical bond between said chemical functionality groups X1 and Y1, thereby forming said first joined oligonucleotide product having the wild type target complementary sequence; and
  (ii) joining of said oligonucleotide probe 3 and oligonucleotide probe 4 to each other by forming said third chemical bond between said chemical functionality groups X3 and Y3, thereby forming said third joined oligonucleotide product having the mutant target complementary sequence;

(d) providing conditions permitting:
  (i) joining of said oligonucleotide probe 1' and oligonucleotide probe 2' to each other by forming said second chemical bond between said chemical functionality groups X2 and Y2, thereby forming said second joined oligonucleotide product having the wild type target sequence; and (ii) joining of said oligonucleotide probe 3' and oligonucleotide probe 4' to each other by forming said fourth chemical bond between said chemical functionality groups X4 and Y4, thereby forming said fourth joined oligonucleotide product having the mutant target sequence;

(e) treating the sample under a denaturing condition;

(f) repeating steps (b) through (e) a desired number of times; and (g) detecting the joined oligonucleotide products.

4. A process as in claim 1, wherein said oligonucleotide probes 1, 1', 2, 2' are selected from twelve alternative groups of which:

in the first, said oligonucleotide probe 1 has a targeting sequence A which includes a long part α and a short part α', and a protecting sequence B, said oligonucleotide probe 1' has a targeting sequence A' which is shorter than said targeting sequence A of said oligonucleotide probe 1, said oligonucleotide probe 2 has a targeting sequence C, said oligonucleotide probe 2' has a targeting sequence C' which includes a long part γ and a short part γ', and is longer than said targeting sequence C of said oligonucleotide probe 2 and a protecting sequence B';

in the second, said oligonucleotide probe 1 has a targeting sequence A and a protecting sequence B, said oligonucleotide probe 1' has a targeting sequence A' which includes a long part a and a short part α', and is longer than said targeting sequence A of said oligonucleotide probe 1, said oligonucleotide probe 2 has a targeting sequence C which includes a long part γ and a short part γ', said oligonucleotide probe 2' has a targeting sequence C' which is shorter than said targeting sequence C of said oligonucleotide probe 2 and a protecting sequence B';

in the third, said oligonucleotide probe 1 has a targeting sequence A and a protecting sequence B, said oligonucleotide probe 1' has a targeting sequence A' which equals in length to said targeting sequence A of said oligonucleotide probe 1, said oligonucleotide probe 2 has a targeting sequence C, said oligonucleotide probe 2' has a targeting sequence C' which equals in length to said targeting sequence C of said oligonucleotide probe 2 and a protecting sequence B';

in the fourth, said oligonucleotide probe 1 has a targeting sequence A which includes a long part α and a short part α', and a protecting sequence B, said oligonucleotide probe 1' has a targeting sequence A' which is shorter than said targeting sequence A of said oligonucleotide probe 1 and a protecting sequence B', said oligonucleotide probe 2 has a targeting sequence C, said oligonucleotide probe 2' has a targeting sequence C' which includes a long part γ and a short part γ', and is longer than said targeting sequence C of said oligonucleotide probe 2;

in the fifth, said oligonucleotide probe 1 has a targeting sequence A and a protecting sequence B, said oligonucleotide probe 1' has a targeting sequence A' which includes a long part α and a short part α', and is longer than said targeting sequence A of said oligonucleotide probe 1 and a protecting sequence B', said oligonucleotide probe 2 has a targeting sequence C which includes a long part γ and a short part γ', said oligonucleotide probe 2' has a targeting sequence C' which is shorter than said targeting sequence C of said oligonucleotide probe 2;

in the sixth, said oligonucleotide probe 1 has a targeting sequence A and a protecting sequence B, said oligonucleotide probe 1' has a targeting sequence A' which equals in length to said targeting sequence A of said oligonucleotide probe 1 and a protecting sequence B', said oligonucleotide probe 2 has a targeting sequence C, said oligonucleotide probe 2' has a targeting sequence C' which equals in length to said targeting sequence C of said oligonucleotide probe 2;

in the seventh, said oligonucleotide probe 1 has a targeting sequence A which includes a long part α and a short part α', said oligonucleotide probe 1' has a targeting sequence A' which is shorter than said sequence A of said oligonucleotide probe 1, said oligonucleotide probe 2 has a targeting sequence C which includes a long part γ and a short part γ', and a protecting sequence B, said oligonucleotide probe 2' has a targeting sequence C' which is longer than said targeting sequence C of said oligonucleotide probe 2 and a protecting sequence B';

in the eighth, said oligonucleotide probe 1 has a targeting sequence A, said oligonucleotide probe 1' has a targeting sequence A' which includes a long part α and a short part α', and is longer than said sequence A of said oligonucleotide probe 1, said oligonucleotide probe 2 has a targeting sequence C which includes a long part γ and a short part γ', and a protecting sequence B, said oligonucleotide probe 2' has a targeting sequence C' which is shorter than said targeting sequence C of said oligonucleotide probe 2 and a protecting sequence B';

in the ninth, said oligonucleotide probe 1 has a targeting sequence A, said oligonucleotide probe 1' has a targeting sequence A' which equals in length to said sequence A of said oligonucleotide probe 1, said oligonucleotide probe 2 has a targeting sequence C and a protecting sequence B, said oligonucleotide probe 2' has a targeting sequence C' which equals in length to said targeting sequence C of said oligonucleotide probe 2 and a protecting sequence B';

in the tenth, said oligonucleotide probe 1 has a targeting sequence A which includes a long part α and a short part α', said oligonucleotide probe 1' has a targeting sequence A' which is shorter than said targeting sequence A of said oligonucleotide probe 1 and a protecting sequence B, said oligonucleotide probe 2 has a targeting sequence C and a protecting sequence B', said oligonucleotide probe 2' has a targeting sequence C' which includes a long part γ and a short part γ', and is longer than said targeting sequence C of said oligonucleotide probe 2;

in the eleventh, said oligonucleotide probe 1 has a targeting sequence A, said oligonucleotide probe 1' has a targeting sequence A' which includes a long part α and a short part α', and is longer than said targeting sequence A of said oligonucleotide probe 1 and a protecting sequence B, said oligonucleotide probe 2 has a targeting sequence C which includes a long part γ and a short part γ', and a protecting sequence B', said oligonucleotide probe 2' has a targeting sequence C' which is shorter than said targeting sequence C of said oligonucleotide probe 2; and in the twelfth, said oligonucleotide probe 1 has a targeting sequence A, said oligonucleotide probe 1' has a targeting sequence A' which equals in length to said targeting sequence A of said oligonucleotide probe 1 and a protecting sequence B, said oligonucleotide probe 2 has a targeting sequence C and a protecting sequence B', said oligonucleotide probe 2' has a targeting sequence C' which equals in length to said targeting sequence C of said oligonucleotide probe 2.

5. A process as in claim 3, wherein said oligonucleotide probes 1, 1', 2, 2' are selected from twelve alternative groups of which:

in the first, said oligonucleotide probe 1 has a targeting sequence A which includes a long part α and a short part α', and a protecting sequence B, said oligonucleotide probe 1' has a targeting sequence A' which is shorter than said targeting sequence A of said oligonucleotide probe 1, said oligonucleotide probe 2 has a targeting sequence C, said oligonucleotide probe 2' has a targeting sequence C' which includes a long part γ and a short part γ', and is longer than said targeting sequence C of said oligonucleotide probe 2 and a protecting sequence B';

in the second, said oligonucleotide probe 1 has a targeting sequence A and a protecting sequence B, said oligonucleotide probe 1' has a targeting sequence A' which includes a long part α and a short part α', and is longer than said targeting sequence A of said oligonucleotide probe 1, said oligonucleotide probe 2 has a targeting sequence C which includes a long part γ and a short part γ', said oligonucleotide probe 2' has a targeting sequence C' which is shorter than said targeting sequence C of said oligonucleotide probe 2 and a protecting sequence B';

in the third, said oligonucleotide probe 1 has a targeting sequence A and a protecting sequence B, said oligonucleotide probe 1' has a targeting sequence A' which equals in length to said targeting sequence A of said oligonucleotide probe 1, said oligonucleotide probe 2 has a targeting sequence C, said oligonucleotide probe 2' has a targeting sequence C' which equals in length to said targeting sequence C of said oligonucleotide probe 2 and a protecting sequence B';

in the fourth, said oligonucleotide probe 1 has a targeting sequence A which includes a long part α and a short part α', and a protecting sequence B; said oligonucleotide probe 1' has a targeting sequence A' which is shorter than said targeting sequence A of said oligonucleotide probe 1 and a protecting sequence B', said oligonucleotide probe 2 has a targeting sequence C, said oligonucleotide probe 2' has a targeting sequence C' which includes a long part γ and a short part γ', and is longer than said targeting sequence C of said oligonucleotide probe 2;

in the fifth, said oligonucleotide probe 1 has a targeting sequence A and a protecting sequence B, said oligonucleotide probe 1' has a targeting sequence A' which includes a long part α and a short part α', and is longer than said targeting sequence A of said oligonucleotide probe 1 and a protecting sequence B', said oligonucleotide probe 2 has a targeting sequence C which includes a long part γ and a short part γ', said oligonucleotide probe 2' has a targeting sequence C' which is shorter than said targeting sequence C of said oligonucleotide probe 2;

in the sixth, said oligonucleotide probe 1 has a targeting sequence A and a protecting sequence B, said oligonucleotide probe 1' has a targeting sequence A' which equals in length to said targeting sequence A of said oligonucleotide probe 1 and a protecting sequence B', said oligonucleotide probe 2 has a targeting sequence C, said oligonucleotide probe 2' has a targeting sequence C' which equals in length to said targeting sequence C of said oligonucleotide probe 2;

in the seventh, said oligonucleotide probe 1 has a targeting sequence A which includes a long part α and a short part α', said oligonucleotide probe 1' has a targeting sequence A' which is shorter than said sequence A of said oligonucleotide probe 1, said oligonucleotide probe 2 has a targeting sequence C which includes a long part γ and a short part γ', and a protecting sequence B, said oligonucleotide probe 2' has a targeting sequence C' which is longer than said targeting sequence C of said oligonucleotide probe 2 and a protecting sequence B';

in the eighth, said oligonucleotide probe 1 has a targeting sequence A, said oligonucleotide probe 1' has a targeting sequence A' which includes a long part α and a short part α', and is longer than said sequence A of said oligonucleotide probe 1, said oligonucleotide probe 2 has a targeting sequence C which includes a long part γ and a short part γ', and a protecting sequence B, said oligonucleotide probe 2' has a targeting sequence C' which is shorter than said targeting sequence C of said oligonucleotide probe 2 and a protecting sequence B';

in the ninth, said oligonucleotide probe 1 has a targeting sequence A, said oligonucleotide probe 1' has a targeting sequence A' which equals in length to said sequence A of said oligonucleotide probe 1, said oligonucleotide probe 2 has a targeting sequence C and a protecting sequence B, said oligonucleotide probe 2' has a targeting sequence C' which equals in length to said targeting sequence C of said oligonucleotide probe 2 and a protecting sequence B';

in the tenth, said oligonucleotide probe 1 has a targeting sequence A which includes a long part α and a short part α', said oligonucleotide probe 1' has a targeting sequence A' which is shorter than said targeting sequence A of said oligonucleotide probe 1 and a protecting sequence B, said oligonucleotide probe 2 has a targeting sequence C and a protecting sequence B', said oligonucleotide probe 2' has a targeting sequence C' which includes a long part γ and a short part γ', and is longer than said targeting sequence C of said oligonucleotide probe 2;

in the eleventh, said oligonucleotide probe 1 has a targeting sequence A, said oligonucleotide probe 1' has a targeting sequence A' which includes a long part α and a short part α', and is longer than said targeting sequence A of said oligonucleotide probe 1 and a protecting sequence B, said oligonucleotide probe 2 has a targeting sequence C which includes a long part γ and a short part γ', and a protecting sequence B', said oligonucleotide probe 2' has a targeting sequence C' which is shorter than said targeting sequence C of said oligonucleotide probe 2; and in the twelfth, said oligonucleotide probe 1 has a targeting sequence A, said oligonucleotide probe 1' has a targeting sequence A' which equals in length to said targeting sequence A of said oligonucleotide probe 1 and a protecting sequence B, said oligonucleotide probe 2 has a targeting sequence C and a protecting sequence B', said oligonucleotide probe 2' has a targeting sequence C' which equals in length to said targeting sequence C of said oligonucleotide probe 2 and wherein said oligonucleotide probes 3, 3', 4, 4' are selected from twelve alternative groups of which:

in the first, said oligonucleotide probe 3 has a targeting sequence A which includes a long part $\alpha$ and a short part $\alpha'$, and a protecting sequence D, said oligonucleotide probe 3' has a targeting sequence A' which is shorter than said targeting sequence A of said oligonucleotide probe 3, said oligonucleotide probe 4 has a targeting sequence C, said oligonucleotide probe 4' has a targeting sequence C' which includes a long part $\gamma$ and a short part $\gamma'$, and is longer than said targeting sequence C of said oligonucleotide probe 4 and a protecting sequence D';

in the second, said oligonucleotide probe 3 has a targeting sequence A and a protecting sequence D, said oligonucleotide probe 3' has a targeting sequence A' which includes a long part $\alpha$ and a short part $\alpha'$, and is longer than said targeting sequence A of said oligonucleotide probe 3, said oligonucleotide probe 4 has a targeting sequence C which includes a long part $\gamma$ and a short part $\gamma'$, said oligonucleotide probe 4' has a targeting sequence C' which is shorter than said targeting sequence C of said oligonucleotide probe 4 and a protecting sequence D';

in the third, said oligonucleotide probe 3 has a targeting sequence A and a protecting sequence D, said oligonucleotide probe 3' has a targeting sequence A' which equals in length to said targeting sequence A of said oligonucleotide probe 3, said oligonucleotide probe 4 has a targeting sequence C, said oligonucleotide probe 4' has a targeting sequence C' which equals in length to said targeting sequence C of said oligonucleotide probe 4 and a protecting sequence D';

in the fourth, said oligonucleotide probe 3 has a targeting sequence A which includes a long part $\alpha$ and a short part $\alpha'$, and a protecting sequence D, said oligonucleotide probe 3' has a targeting sequence A' which is shorter than said targeting sequence A of said oligonucleotide probe 3 and a protecting sequence D', said oligonucleotide probe 4 has a targeting sequence C, said oligonucleotide probe 4' has a targeting sequence C' which includes a long part $\gamma$ and a short part $\gamma'$, and is longer than said targeting sequence C of said oligonucleotide probe 4;

in the fifth, said oligonucleotide probe 3 has a targeting sequence A and a protecting sequence D, said oligonucleotide probe 3' has a targeting sequence A' which includes a long part $\alpha$ and a short part $\alpha'$, and is longer than said targeting sequence A of said oligonucleotide probe 3 and a protecting sequence D', said oligonucleotide probe 4 has a targeting sequence C which includes a long part $\gamma$ and a short part $\gamma'$, said oligonucleotide probe 4' has a targeting sequence C' which is shorter than said targeting sequence C of said oligonucleotide probe 4;

in the sixth, said oligonucleotide probe 3 has a targeting sequence A and a protecting sequence D, said oligonucleotide probe 3' has a targeting sequence A' which equals in length to said targeting sequence A of said oligonucleotide probe 3 and a protecting sequence D', said oligonucleotide probe 4 has a targeting sequence C, said oligonucleotide probe 4' has a targeting sequence C' which equals in length to said targeting sequence C of said oligonucleotide probe 4;

in the seventh, said oligonucleotide probe 3 has a targeting sequence A which includes a long part $\alpha$ and a short part $\alpha'$, said oligonucleotide probe 3' has a targeting sequence A' which is shorter than said sequence A of said oligonucleotide probe 3, said oligonucleotide probe 4 has a targeting sequence C which includes a long part $\gamma$ and a short part $\gamma'$, and a protecting sequence D, said oligonucleotide probe 4' has a targeting sequence C' which is longer than said targeting sequence C of said oligonucleotide probe 4 and a protecting sequence D';

in the eighth, said oligonucleotide probe 3 has a targeting sequence A, said oligonucleotide probe 3' has a targeting sequence A' which includes a long part $\alpha$ and a short part $\alpha'$, and is longer than said sequence A of said oligonucleotide probe 3, said oligonucleotide probe 4 has a targeting sequence C which includes a long part $\gamma$ and a short part $\gamma'$, and a protecting sequence D, said oligonucleotide probe 4' has a targeting sequence C' which is shorter than said targeting sequence C of said oligonucleotide probe 4 and a protecting sequence D';

in the ninth, said oligonucleotide probe 3 has a targeting sequence A, said oligonucleotide probe 3' has a targeting sequence A' which equals in length to said sequence A of said oligonucleotide probe 3, said oligonucleotide probe 4 has a targeting sequence C and a protecting sequence D, said oligonucleotide probe 4' has a targeting sequence C' which equals in length to said targeting sequence C of said oligonucleotide probe 4 and a protecting sequence D';

in the tenth, said oligonucleotide probe 3 has a targeting sequence A which includes a long part $\alpha$ and a short part $\alpha'$, said oligonucleotide probe 3' has a targeting sequence A' which is shorter than said targeting sequence A of said oligonucleotide probe 3 and a protecting sequence D, said oligonucleotide probe 4 has a targeting sequence C and a protecting sequence D', said oligonucleotide probe 4' has a targeting sequence C' which includes a long part $\gamma$ and a short part $\gamma'$, and is longer than said targeting sequence C of said oligonucleotide probe 4;

in the eleventh, said oligonucleotide probe 3 has a targeting sequence A, said oligonucleotide probe 3' has a targeting sequence A' which includes a long part $\alpha$ and a short part $\alpha'$, and is longer than said targeting sequence A of said oligonucleotide probe 3 and a protecting sequence D, said oligonucleotide probe 4 has a targeting sequence C which includes a long part $\gamma$ and a short part $\gamma'$, and a protecting sequence D', said oligonucleotide probe 4' has a targeting sequence C' which is shorter than said targeting sequence C of said oligonucleotide probe 4; and in the twelfth, said oligonucleotide probe 3 has a targeting sequence A, said oligonucleotide probe 3' has a targeting sequence A' which equals in length to said targeting sequence A of said oligonucleotide probe 3 and a protecting sequence D, said oligonucleotide probe 4 has a targeting sequence C and a protecting sequence D', said oligonucleotide probe 4' has a targeting sequence C' which equals in length to said targeting sequence C of said oligonucleotide probe 4.

6. A process as in any of claims 3, 4 and 5, wherein the number of nucleotides contained in the $\alpha'$ and $\gamma'$ parts is selected from the group of numbers consisting of five, four, three, two, one and zero nucleotides.

7. A process as in any of claims 2, 3, 4 and 5, wherein said chemical functionality group X1 is an electrophile and said chemical functionality group Y1 is a nucleophile.

8. A process as in any of claims 1, 2, 3, 4 and 5, wherein said chemical functionality group X1 is a nucleophile and said chemical functionality group Y1 is an electrophile.

9. A process as in any of claims 1, 2, 3, 4 and 5, wherein said chemical functionality group X2 is an electrophile and said chemical functionality group Y2 is a nucleophile.

10. A process as in any of claims 1, 2, 3, 4 and 5, wherein said chemical functionality group X2 is a nucleophile and said chemical functionality group Y2 is an electrophile.

11. A process as in any of claims 3 and 5, wherein said chemical functionality group X3 is an electrophile and said chemical functionality group Y3 is a nucleophile.

12. A process as in any of claims 3 and 5, wherein said chemical functionality group X3 is a nucleophile and said chemical functionality group Y3 is an electrophile.

13. A process as in any of claims 3 and 5, wherein said chemical functionality group X4 is an electrophile and said chemical functionality group Y4 is a nucleophile.

14. A process as in any of claims 3 and 5, wherein said chemical functionality group X4 is a nucleophile and said chemical functionality group Y4 is an electrophile.

15. A process as in any of claims 1, 2, 3, 4 and 5, wherein said chemical functionality group X1, X2, Y1 or Y2 replaces a hydroxyl group located at a C-2' position of a ribose ring of a nucleotide in said oligonucleotide probes 1, 1', 2 or 2', respectively.

16. A process as in any of claims 1, 2, 3, 4 and 5, wherein each of said chemical functionality groups X1, X2, Y1 and Y2 replaces a hydrogen in a hydroxyl group located at a C-2' position of a ribose ring of a nucleotide in said oligonucleotide probes 1, 1', 2 and 2', respectively.

17. A process as in any of claims 1, 2, 3, 4 and 5, wherein each of said chemical functionality groups X1, X2, Y1 and Y2 replaces a hydrogen in an amino group located at a C-6 position of an adenine or cytidine residue in said oligonucleotide probes 1, 1', 2 and 2', respectively.

18. A process as in any of claims 1, 2, 3, 4 and 5, wherein each of said chemical functionality groups X1, X2, Y1 and Y2 replaces a hydrogen located at a C-8 position of an adenine or guanine residue in said oligonucleotide probes 1, 2, 1' and 2', respectively.

19. A process as in any of claims 1, 2, 3, 4 and 5, wherein each of said chemical functionality groups X2, X2, Y1 and Y2 replaces a hydrogen from a methyl group located at a C-5 position of a thymidine residue in said oligonucleotide probes 1, 1', 2 and 2', respectively.

20. A process as in any of claims 3 and 5, wherein each of said chemical functionality groups X3, X4, Y3 and Y4 replaces a hydroxyl group located at a C-2' position of a ribose ring of a nucleotide in said oligonucleotide probes 3, 3', 4 and 4', respectively.

21. A process as in any of claims 3 and 5, wherein each of said chemical functionality groups X3, X4, Y3 and Y4 replaces a hydrogen in a hydroxyl group located at a C-2' position of a ribose ring of a nucleotide in said oligonucleotide probes 3, 3', 4 and 4', respectively.

22. A process as in any of claims 3 and 5, wherein each of said chemical functionality groups X3, X4, Y3 and Y4 replaces a hydrogen in an amino group located at a C-6 position of an adenine or cytidine residue in said oligonucleotide probes 3, 3', 4 and 4', respectively.

23. A process as in any of claims 3 and 5, wherein each of said chemical functionality groups X3, X4, Y3 and Y4 replaces a hydrogen located at a C-8 position of an adenine or guanine residue in said oligonucleotide probes 3, 3', 4 and 4', respectively.

24. A process as in any of claims 3 and 5, wherein each of said chemical functionality groups X3, X4, Y3 and Y4 replaces a hydrogen from a methyl group located at a C-5 position of a thymidine residue in oligonucleotide probes 3, 3', 4 and 4', respectively.

25. A process as in any of claims 1, 2, 3, 4 and 5, wherein said protecting sequences B and B' are complementary to sequences in an oligonucleotide probe of which said sequences B and B' are a part of in a palindrome manner, and protect said chemical functionality groups X1 and X2 from interacting with said chemical functionality groups Y1 and Y2.

26. A process as in any of claims 1, 2, 3, 4 and 5, wherein each of said chemical functionality groups X1, X2, Y1 and Y2 in said oligonucleotide probes 1, 2, 1' and 2', respectively, is protected by additional oligonucleotides 1.1, 2.1, 1.1' and 2.1', respectively.

27. A process as in any of claims 3 and 5, wherein said protecting sequences D and D' are complementary to sequences in an oligonucleotide probe of which said sequences D and D' are part of in a palindrome manners and therefore protect said chemical functionality groups X3 and X4 from interacting with said chemical functionality groups Y3 and Y4.

28. A process as in any of claims 1, 2, 3, 4 and 5, wherein each of said chemical functionality groups X3, X4, Y3 and Y4 in oligonucleotide probes 3, 4, 3'or 4', respectively, is protected by additional oligonucleotides 3.1, 4.1, 3.1' and 4.1', respectively.

29. A process as in any of claims 1, 2, 3, 4 and 5, wherein the reaction between said chemical functionality groups X1 and Y1 and between X2 and Y2 is a substitution of a nucleophile for an electrophilic leaving group.

30. A process as in any of claims 1, 2, 3, 4 and 5, wherein the reaction between said chemical functionality groups X1 and Y1 and between X2 and Y2 is a Michael addition reaction.

31. A process as in any of claims 1, 2, 3, 4 and 5, wherein the reaction between said chemical functionality groups X1 and Y1 and between X2 and Y2 is a Diels-Alder reaction.

32. A process as in any of claims 1, 2, 3, 4 and 5, wherein the reaction between said chemical functionality groups X1 and Y1 and between X2 and Y2 is an addition of a thiol group to the double bond of a maleimido moiety.

33. A process as in any of claims 1, 2, 3, 4 and 5, wherein the reaction between said chemical functionality groups X1 and Y1 and between X2 and Y2 is a photochemical reaction.

34. A process as in any of claims 1, 2, 3, 4 and 5, wherein the reaction between said chemical functionality groups X1 and Y1 and between X2 and Y2 is a photocyclodimerization reaction.

35. A process as in any of claims 3 and 5, wherein the reaction between said chemical functionality groups X3 and Y3 and between X4 and Y4 is a substitution of a nucleophile for an electrophilic leaving group.

36. A process as in any of claims 3 and 5, wherein the reaction between chemical said functionality groups X3 and Y3 and between X4 and Y4 is a Michael addition reaction.

37. A process as in any of claims 3 and 5, wherein the reaction between said chemical functionality groups X3 and Y3 and between X4 and Y4 is a Diels-Alder reaction.

38. A process as in any of claims 3 and 5, wherein the reaction between said chemical functionality groups X3 and Y3 and between X4 and Y4 is an addition of a thiol group to the double bond of a maleimido moiety.

39. A process as in any of claims 3 and 5, wherein the reaction between said chemical functionality groups X3 and Y3 and between X4 and Y4 is a photochemical reaction.

40. A process as in any of claims 3 and 5, wherein the reaction between said chemical functionality groups X3 and Y3 and between X4 and Y4 is a photocyclodimerization reaction.

41. A process as in any of claims 1, 2, 3, 4 and 5, wherein the oligonucleotide pairs are present at a molar excess in the range of $10^5$ to $10^{15}$ pairs per nucleic acid target sequence or target complementary sequence.

42. A process as in any of claims 1, 2, 3, 4 and 5, wherein said oligonucleotide probes are substantially complementary to the target sequences.

43. A process as in any of claims 1, 2, 3, 4 and 5, wherein said oligonucleotide probes are fully complementary to the target sequences.

44. A process as in any of claims 1, 2, 3, 4 and 5, wherein the target sequence is selected from the group consisting of deoxyribonucleic acid, ribonucleic acid, and a copolymer of deoxyribonucleic acid and ribonucleic acid.

45. A process as in any of claims 1, 2, 3, 4 and 5, wherein the oligonucleotide probes include nucleotides selected from the group consisting of deoxyribonucleotides, ribonucleotides, protein nucleic acids and their analogs.

46. A process as in any of claims 1, 2, 3, 4 and 5, wherein the nucleic acid of interest is a polymerase chain reaction product.

47. A process as in any of claims 1, 2, 3, 4 and 5, wherein the nucleic acid of interest is a ligase chain reaction product.

48. A process as in any of claims 1, 2, 3, 4 and 5, wherein the nucleic acid of interest is a chemical amplification reaction product.

49. A process as in any of claims 1, 2, 3, 4 and 5, wherein said denaturation is accomplished by selecting a method from a group of methods consisting of heating, alkali treatment and enzymatic treatment.

50. A process as in any of claims 1, 2, 3, 4 and 5, wherein said detection of said joined oligonucleotide products is accomplished by labeling one or more of said oligonucleotide probes in a label selected from a group of labels consisting of radioactive labels, enzymes, chromophores, flourophores, luminophores, atoms and molecules detectable by electron microscopy and metal ions detectable by their magnetic properties.

51. A process as in claim 50, wherein said detection of said joined oligonucleotide products is accomplished with a capture assay.

52. A process as in any of claims 1, 2, 3, 4 and 5, wherein said detection of said joined oligonucleotide products is accomplished by size separation.

53. A process as in any of claims 1, 2, 3, 4 and 5, wherein said detection of said joined oligonucleotide products is accomplished by selecting said chemical functionality groups such that said chemical functionality groups form a detectable compound when a chemical bond is formed between them.

54. A process as in claim 53, wherein said detectable compound is detected via a detection method selected from a group of methods consisting of colorimetic methods fluorimetric methods and luminometric methods.

55. A process as in claim 53, wherein said detectable compound is detected via an antibody.

56. A process as in any of claims 1, 2, 3, 4 and 5, wherein said detection of said joined oligonucleotide products is affected by presence of single stranded protecting sequences B and B'.

57. A process as in any of claims 3 and 5, wherein said detection of said joined oligonucleotide products is based on presence of single stranded protecting sequences D and D'.

58. A process as in claim 56, wherein at least one of said single stranded protecting sequences B and B' serve as a first detection oligonucleotide probe, to which attached is a first proximity energy transfer label, and to at least one second detection oligonucleotide probe B.1 and B'.1, which are complementary to said protecting sequences B and B', respectively, attached is a second proximity energy transfer label in an arrangement permitting energy transfer when said first detection oligonucleotide probe is hybridized to said second detection oligonucleotide probe.

59. A process as in claim 56, wherein to at least one location of at least one of said single stranded protecting sequences B and B' attached is a label moiety that is released from said joined oligonucleotide products by the activity of a single stranded specific nuclease, and to at least one location of at least one of said oligonucleotide probes attached is a separation moiety which can bind to a counterpart separation moiety attached to a solid support.

60. A process as in claim 59, wherein said single stranded specific nuclease is selected from a group of single stranded specific nucleases consisting of Exonuclease 7 from *E. Coli.*, S1 nuclease from *Aspergillus oryzae* and Mung been nuclease from *Phaseolus aureus*.

61. A process as in claim 59, wherein said label moiety is released from said joined oligonucleotide products by a chemical process which specifically degrades single-stranded sequences.

62. A process for amplifying and detecting, in a sample containing a nucleic acid of interest, a nucleic acid molecule including a wild type target sequence, a mutant target sequence, a wild-type target complementary sequence or a mutant target complementary sequence, in a single or double stranded form, the process comprising the steps of the process of claim 5 being performed in at least one vessel, using a reagent which includes:

(a) at least two oligonucleotide probe pairs, at least one is conjugated to a first separation moiety, and at least one is conjugated to a label moiety;

(b) a single-strand specific nuclease;

(c) a solid support to which attached is a second corresponding affinity separation moiety; and (d) two or more detection oligonucleotide probes conjugated to a proximity labeling moiety.

63. A process of determining the genotype of an individual comprising the steps of the process of claim 5 being performed in at least one using a reagent which includes:

(a) at least two oligonucleotide probe pairs, at least one is conjugated to a first separation moiety, and at least one is conjugated to a label moiety;

(b) a single-strand specific nuclease;

(c) a solid support to which attached is a second corresponding affinity separation moiety; and (d) two or more detection oligonucleotide probes conjugated to a proximity labeling moiety.

64. A process of determining the identity a nucleotide base in a specific position in an allele comprising the steps of the process of claim 5.

65. A process of determining the presence of a target sequence in a sample containing a nucleic acid of interest comprising the steps of the process of claim 4.

* * * * *

SEQUENCE LISTING ( 1 ) GENERAL INFORMATION:

( i i i ) NUMBER OF SEQUENCES:16

( 2 ) INFORMATION FOR SEQ ID NO:1:

( i ) SEQUENCE CHARACTERISTICS:
        ( A ) LENGTH:54
        ( B ) TYPE:nucleic acid
        ( C ) STRANDEDNESS:single
        ( D ) TOPOLOGY:linear ( x i ) SEQUENCE DESCRIPTION: SEQ ID NO:1:

AGACCTGTTA ATGGGCACAC TAGGAATTGT GTGCCCATC TGTTCTCAGA AACC     54

( 2 ) INFORMATION FOR SEQ ID NO:2:

( i ) SEQUENCE CHARACTERISTICS:
        ( A ) LENGTH:34

```
            ( B ) TYPE: nucleic acid
            ( C ) STRANDEDNESS: single
            ( D ) TOPOLOGY: linear ( x i ) SEQUENCE DESCRIPTION: SEQ ID NO:2:

GGGTAGGAUT CCTAGTGTGC CCATTAACA GGTCT                                      3 4

( 2 ) INFORMATION FOR SEQ ID NO:3:

( i ) SEQUENCE CHARACTERISTICS:
            ( A ) LENGTH: 29
            ( B ) TYPE: nucleic acid
            ( C ) STRANDEDNESS: single
            ( D ) TOPOLOGY: linear ( x i ) SEQUENCE DESCRIPTION: SEQ ID NO:3:

GGTTTCTGAG AACAGATGGG GCACACAAU                                            2 9

( 2 ) INFORMATION FOR SEQ ID NO:4:

( i ) SEQUENCE CHARACTERISTICS:
            ( A ) LENGTH: 34
            ( B ) TYPE: nucleic acid
            ( C ) STRANDEDNESS: single
            ( D ) TOPOLOGY: linear ( x i ) SEQUENCE DESCRIPTION: SEQ ID NO:4:

AGACCTGTTA ATGGGCACAC TAGGAAUCCT ACCC                                      3 4

( 2 ) INFORMATION FOR SEQ ID NO:5:

( i ) SEQUENCE CHARACTERISTICS:
            ( A ) LENGTH: 27
            ( B ) TYPE: nucleic acid
            ( C ) STRANDEDNESS: single
            ( D ) TOPOLOGY: linear ( x i ) SEQUENCE DESCRIPTION: SEQ ID NO:5:

UGTGTGCCCC ATCTGTTCTC AGAAACC                                              2 7

( 2 ) INFORMATION FOR SEQ ID NO:6:

( i ) SEQUENCE CHARACTERISTICS:
            ( A ) LENGTH: 58
            ( B ) TYPE: nucleic acid
            ( C ) STRANDEDNESS: single
            ( D ) TOPOLOGY: linear ( x i ) SEQUENCE DESCRIPTION: SEQ ID NO:6:

TACATGTGTA ACAGTTCCTG CATGGGCGGC ATGAACCGGA GGCCCATCCT CACCATCA            5 8

( 2 ) INFORMATION FOR SEQ ID NO:7:

( i ) SEQUENCE CHARACTERISTICS:
            ( A ) LENGTH: 58
            ( B ) TYPE: nucleic acid
            ( C ) STRANDEDNESS: single
            ( D ) TOPOLOGY: linear ( x i ) SEQUENCE DESCRIPTION: SEQ ID NO:7:

TACATGTGTA ACAGTTCCTG CATGGGCAGC ATGAACCGGA GGCCCATCCT CACCATCA            5 8

( 2 ) INFORMATION FOR SEQ ID NO:8:

( i ) SEQUENCE CHARACTERISTICS:
            ( A ) LENGTH: 40
            ( B ) TYPE: nucleic acid
            ( C ) STRANDEDNESS: single
```

(D) TOPOLOGY:linear (xi) SEQUENCE DESCRIPTION: SEQ ID NO:8:

CTACTAAGGC CCGCCCATGC AGGAACTGTT ACACAATGTA 40

(2) INFORMATION FOR SEQ ID NO:9:

(i) SEQUENCE CHARACTERISTICS:
(A) LENGTH:29
(B) TYPE:nucleic acid
(C) STRANDEDNESS:single
(D) TOPOLOGY:linear (xi) SEQUENCE DESCRIPTION: SEQ ID NO:9:

TGATGGTGAG GATGGGCCTC CGGTTCATG 29

(2) INFORMATION FOR SEQ ID NO:10:

(i) SEQUENCE CHARACTERISTICS:
(A) LENGTH:39
(B) TYPE:nucleic acid
(C) STRANDEDNESS:single
(D) TOPOLOGY:linear (xi) SEQUENCE DESCRIPTION: SEQ ID NO:10:

TACATGTGTA ACAGTTCCTG CATGGGCGGG CCTTAGTAG 39

(2) INFORMATION FOR SEQ ID NO:11:

(i) SEQUENCE CHARACTERISTICS:
(A) LENGTH:29
(B) TYPE:nucleic acid
(C) STRANDEDNESS:single
(D) TOPOLOGY:linear (xi) SEQUENCE DESCRIPTION: SEQ ID NO:11:

CATGAACCGG AGGCCCATCC TCACCATCA 29

(2) INFORMATION FOR SEQ ID NO:12:

(i) SEQUENCE CHARACTERISTICS:
(A) LENGTH:10
(B) TYPE:nucleic acid
(C) STRANDEDNESS:single
(D) TOPOLOGY:linear (xi) SEQUENCE DESCRIPTION: SEQ ID NO:12:

GCCTTAGTAG 10

(2) INFORMATION FOR SEQ ID NO:13:

(i) SEQUENCE CHARACTERISTICS:
(A) LENGTH:39
(B) TYPE:nucleic acid
(C) STRANDEDNESS:single
(D) TOPOLOGY:linear (xi) SEQUENCE DESCRIPTION: SEQ ID NO:13:

GCAATAGCTA TCGCCCATGC AGGAACTGTT ACACATGTA 39

(2) INFORMATION FOR SEQ ID NO:14:

(i) SEQUENCE CHARACTERISTICS:
(A) LENGTH:29
(B) TYPE:nucleic acid
(C) STRANDEDNESS:single
(D) TOPOLOGY:linear ( x i ) SEQUENCE DESCRIPTION: SEQ ID NO:14:

TGATGGTGAG GATGGGCCTC CGGTTCATG                2 9

( 2 ) INFORMATION FOR SEQ ID NO:15:

( i ) SEQUENCE CHARACTERISTICS:
      ( A ) LENGTH:39
      ( B ) TYPE:nucleic acid
      ( C ) STRANDEDNESS:single
      ( D ) TOPOLOGY:linear ( x i ) SEQUENCE DESCRIPTION: SEQ ID NO:15:

TACATGTGTA ACAGTTCCTG CATGGGCAGT AGCTATTGC           3 9

( 2 ) INFORMATION FOR SEQ ID NO:16:

( i ) SEQUENCE CHARACTERISTICS:
      ( A ) LENGTH:29
      ( B ) TYPE:nucleic acid
      ( C ) STRANDEDNESS:single
      ( D ) TOPOLOGY:linear ( x i ) SEQUENCE DESCRIPTION: SEQ ID NO:16:

CATGAACCGG AGGCCCATCC TCACCATCA                2 9